United States Patent [19]
Matalon et al.

[11] Patent Number: 5,679,635
[45] Date of Patent: Oct. 21, 1997

[54] ASPARTOACYLASE GENE, PROTEIN, AND METHODS OF SCREENING FOR MUTATONS ASSOCIATED WITH CANAVAN DISEASE

[75] Inventors: Reuben Matalon, Coral Gables; Rajinder Kaul, Miami; Guang Ping Gao, Miami; Kuppareddi Balamurugan, Miami; Kimberlee Michals-Matalon, Coral Gables, all of Fla.

[73] Assignee: Miami Children's Hospital Research Institute, Inc., Miami, Fla.

[21] Appl. No.: 302,449

[22] Filed: Sep. 9, 1994

Related U.S. Application Data

[63] Continuation of PCT/US94/07430, Jul. 5, 1994, which is a continuation-in-part of Ser. No. 128,020, Sep. 29, 1993.

[51] Int. Cl.$^6$ .............................. C12Q 1/68; C12P 19/34; C07H 21/02; C07H 21/04
[52] U.S. Cl. .................... 435/6; 435/91.2; 435/69.1; 435/240.4; 435/252.3; 435/254.2; 435/172.3; 435/91.4; 536/24.1; 536/3.1; 536/24.3; 536/24.33
[58] Field of Search .................. 435/6, 91.2, 69.1, 435/91.1, 240.4, 252.3, 254.2, 172.3, 91.4; 536/23.1, 24.3, 24.33, 24.1

[56] References Cited

PUBLICATIONS

Rothwell et al, Understanding Genetics; A Molecular Approach (Wiley–Liss) 1993, pp. 264–269.

*Primary Examiner*—W. Gary Jones
*Assistant Examiner*—Dianne Rees
*Attorney, Agent, or Firm*—Millen, White, Zelano & Branigan, P.C.

[57] ABSTRACT

Canavan disease, an autosomal recessive leukodystrophy, is caused by deficiency of aspartoacylase and accumulation of N-acetylaspartic acid in brain. Human aspartoacylase (ASP) cDNA spanning 1,435 bp has been cloned and expressed in *E. coli*. A base change, a854>c, has been found in 85% of the 34 Canavan alleles tested so far, which results in a missense glu285>ala mutation that is predicted to be part of the catalytic domain of aspartoacylase. Several additional mutations have also been identified. The invention therefore provides nucleic acid sequences, genes, polypeptides, antibodies, vectors containing the gene, host cells transformed with vectors containing the gene, animal models for the disease, methods for expressing the polypeptide, genetic screening methods and kits, diagnostic methods and kits, methods of treating Canavan disease and methods of genetic therapy for the disease.

44 Claims, 20 Drawing Sheets

```
                TTGTAACAGA AAATTAAAAT ATACTCCACT CAAGGGAATT CTGTACTTTG CCCTTTTGGT   -99
     AAAGTCTCAT TTACATTTCT AAACCTTTCT TAAGAAAATC GAATTCCTT  TGATCTCTCT             -39
                                                                       C  H  I
  1  TCTGAATTGC AGAAATCAGA TAAAAACTAC TTGGTGAA ATG ACT TCT TGT CAC ATT          18
                                          -1   M   T   S   C   H   I
                                                                           G
  7  GCT GAA GAA CAT ATA CAA AAG GTT GCT ATC TTT GGA GGA ACC CAT GGG            66
      A   E   E   H   I   Q   K   V   A   I   F   G   G   T   H   G
 23  AAT GAG CTA ACC GGA GTA TTT CTG GTT AAG CAT TGG CTA GAG AAT GGC           114
      N   E   L   T   G   V   F   L   V   K   H   W   L   E   N   G
 39  GCT GAG ATT CAG AGA ACA GGG CTG GAG GTA AAA CCA TTT ATT ACT AAC           162
      A   E   I   Q   R   T   G   L   E   V   K   P   F   I   T   N
 55  CCC AGA GCA GTG AAG AAG TGT ACC AGA TAT ATT GAC TGT GAC CTG AAT           210
      P   R   A   V   K   K   C   T   R   Y   I   D   C   D   L   N
 71  CGC ATT TTT GAC CTT GAA AAT CTT GGC AAA AAA ATG AGT GAA GAT TTG           258
      R   I   F   D   L   E   N   L   G   K   K   M   S   E   D   L
 87  CCA TAT GAA GTG AGA AGG GCT CAA GAT ATA CAT ATT TTT GGT CCA               306
      P   Y   E   V   R   R   A   Q   D   I   H   L   F   G   P
                                                                N*  T
103  AAA GAC AGT AAC ATG GGG GAA GAT TCC TAT CTT GAG CTT CAC AAC ACC           354
      K   D   S   N   M   G   E   D   S   Y   L   E   L   H   N   T
                                                               N   N
119  ACC TCT AAC ATG TGC ACT CTT ATT TAC ATT AAG ACT TCT CTG GCT CCA CTA       402
      T   S   N   M   C   T   L   I   Y   I   K   T   S   L   A   P   L
                                                                           T
135  TTT TTA ATT CAG ATG TTT CAT TAC ATT GAG CAT CCT TCC CTC AAA TAT GCG ACC   450
      F   L   I   Q   M   F   H   Y   I   E   H   P   S   L   K   Y   A
151                                                                            498
      P   C   Y   V   Y   L   I   A   K   Y   P   V   G   I   E   V   G
167
      T   R   S   I                                                     Q
```

FIG.1A

|     | | | | | | | | | | | | | | | | |
|---|---|---|---|---|---|---|---|---|---|---|---|---|---|---|---|---|
|     | ACT | CGT | TCC | ATA | GCC | AAG | TAT | CCT | GTG | GGT | ATA | GAA | GTT | GGT | CCT | CAG 546 |
| 183 | P | Q | G | V | L | R | A | D | I | L | D | Q | M | R | K | M |
|     | CCT | CAA | GGG | GTT | CTG | AGA | GAT | GCT | TTG | CAT | CAT | TTC | AAT | CAA | ATG | AGA AAA ATG 594 |
| 199 | I | K | H | A | L | D | F | I | H | H | F | N | Q | M | E | G | K | E |
|     | ATT | AAA | CAT | GCT | CTT | GAT | TTT | ATA | CAT | CAT | TTC | AAT | GAA | GGA | AAA | GAA 642 |
| 215 | F | P | P | C | A | I | E | V | Y | K | I | I | E | K | V | D |
|     | TTT | CCT | CCC | TGC | GCC | ATT | GAG | GTC | TAT | AAA | ATT | ATA | GAG | AAA | GTT | GAT 690 |
| 231 | Y | P | R | D | E | N | G | E | I | A | A | I | H | P | N |
|     | TAC | CCC | CGG | GAT | GAA | AAT | GGA | GAA | ATT | GCT | GCT | ATC | CAT | CCT | AAT 738 |
| 247 | L | Q | D | Q | D | W | K | P | L | H | P | G | D | P | M | F |
|     | CTG | CAG | GAT | CAA | GAC | TGG | AAA | CCA | CTG | CAT | CCT | GGG | GAT | CCC | ATG | TTT 786 |
| 263 | L | T | L | D | G | K | T | I | P | L | G | G | D | C | T | V |
|     | TTA | ACT | CTT | GAT | GGG | AAG | ACG | ATC | CCA | CTG | GGC | GGA | GAC | TGT | ACC | GTG 834 |
| 279 | Y | P | V | F | V | N | E | A | A | Y | Y | E | K | E | A |
|     | TAC | CCC | GTG | TTT | GTG | AAT | GAG | GCC | GCA | TAT | TAC | GAA | AAG | GAA | GCT 882 |
| 295 | F | A | K | T | T | K | L | T | L | N | A | K | S | I | R | C |
|     | TTT | GCA | AAG | ACA | ACT | AAA | CTA | ACG | CTC | AAT | GCA | AAA | AGT | ATT | CGC | TGC 930 |
| 311 | C | L | H | . |

TGT TTA CAT TAG AA ATCACTTCCA GCTTACATCT TACACGGTGT CTTACAAATT 984
CTGCTAGTCT GTAAGCTCCT TAAGAGTAGG GTTGTGCCTT ATTCAACTGC ATACATAGCT 1044
CCTAGCACAG TGCCTTATTC GGTAGGCATC TAAGCAAATT TCTTAAATTA ATTAATATAT 1104
CTTTAAAGAT ATCATATTTT ATGTATGTAG CTTATTCAAA GAAGTGTTTC CTATTCTAT 1164
ATAGTTTATT ATACATGATA CTTGGGTAGC TCAACATTCT TAATAAACAG CCTTTGTATT 1224
CAGAATATAA AATTGAAATA GATATATATA AAGTTAAAAA AAAAAAAAAA AAA 1277

FIG. 1B

```
                   10v       20v       30v       40v       50v
HLASP      MTSCHIAEEHIQKVAIFGGTHGNELTGVFLVKHWLENGAEIQRTGLEVKPF
           MTSCH:AE:.I:KVAIFGGTHGNELTGVFLVKHWLEN::EIQRTGLEVKPF
BASPCDNA   MTSCHVAEDPIKKVAIFGGTHGNELTGVFLVKHWLENSTEIQRTGLEVKPF
                   10^       20^       30^       40^       50^
                   60v       70v       80v       90v       100v
HLASP      ITNPRAVKKCTRYIDCDLNRIFDLENLGKKMSEDLPYEVRRAQEINHLFGP
           ITNPRAVKKCTRYIDCDLNR:FD ENLGKK.SEDLPYEVRRAQEINHLFGP
BASPCDNA   ITNPRAVKKCTRYIDCDLNRVFDPENLGKKKSEDLPYEVRRAQEINHLFGP
                   60^       70^       80^       90^       100^
                   110v      120v      130v      140v      150v
HLASP      KDSEDSYDIIFDLHN*TTSNMGCTLILEDSRNNFLIQMFHYIKTSLAPLPCY
           KDSEDSYDIIFDLHN*TTSNMGCTLILEDSRN:FLIQMFHYIKTSLAPLPCY
BASPCDNA   KDSEDSYDIIFDLHN*TTSNMGCTLILEDSRNDFLIQMFHYIKTSLAPLPCY
                   110^      120^      130^      140^      150^
                   160v      170v      180v      190v      200v
HLASP      VYLIEHPSLKYATTRSIAKYPVGIEVGPQPQGVLRADILDQMRKMIKHALD
           VYLIEHPSLKYATTRSIAKYPVGIEVGPQPQGVLRADILDQMRKMI:HALD
BASPCDNA   VYLIEHPSLKYATTRSIAKYPVGIEVGPQPQGVLRADILDQMRKMIQHALD
                   160^      170^      180^      190^      200^
                   210v      220v      230v      240v      250v
HLASP      FIHHFNEGKEFPPCAIEVYKIIEKVDYPRDENGEIAAIIHPNLQDQDWKPL
           FIH:FNEGKEFPPCAIEVYKI: KVDYPR:E:GEI:AIIHP:LQDQDWKPL
BASPCDNA   FIHNFNEGKEFPPCAIEVYKIMRKVDYPRNESGEISAIIHPKLQDQDWKPL
                   210^      220^      230^      240^      250^
                   260v      270v      280v      290v      300v
HLASP      HPGDPMFLTLDGKTIPLGGDCTVYPVFVNEAAYYEKKEAFAKTTKLTLNAK
           HP.DP:FLTLDGKTIPLGGD TVYPVFVNEAAYYEKKEAFAKTTKLTLNA:
BASPCDNA   HPEDPVFLTLDGKTIPLGGDQTVYPVFVNEAAYYEKKEAFAKTTKLTLNAN
                   260^      270^      280^      290^      300^
                   310v
HLASP      SIRCCLH
           SIR..LH
BASPCDNA   SIRSSLH
                   310^
```

FIG. 2

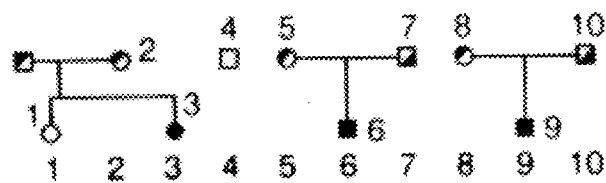

← WT
← MUT
← WT
← MUT

← 239 bp
← 125 bp
← 114 bp

```
            EAM                             M       E   M           N DSNDSBB
            ASA                             B       C   N           L STCSESS
            MPE                             O       5   L           A AYOACAA
            1E3                             2       7   1           4 11111JJ
             /                                                       /////
ATGACTTCTTGTCACATTGCTGAAGAACATATACAAAAGGTTGCTATCTTTGGAGGAACC
----.----+----.----+----.----+----.----+----.----+----.----+   60
TACTGAAGAACAGTGTAACGACTTCTTGTATATGTTTTCCAACGATAGAAACCTCCTTGG m   t   s   c   h   i   a   e   e   h   i   q   k   v   a   i   f   g   g   t
↑— START SITE

----.----+----.----+----.----+----.----+----.----+----.----+----.----+

N       A   BBH             TSM✓    RM      H HHD   TH
            L       L   SCP             RPS     MA      I HAD   FN
            A       U   AAA             UOE     AE      N AEE   IF
            3       1   W72             911     11      P 121   11
             /       /  //               ↓/              /       /    /
CATGGGAATGAGCTAACCGGAGTATTTCTGGTTAAGCATTGGCTAGAGAATGGCGCTGAG
----.----+----.----+----.----+----.----+----.----+----.----+   120
GTACCCTTACTCGATTGGCCTCATAAAGACCAATTCGTAACCGATCTCTTACCGCGACTC h   g   n   e   l   t   g   v   f   l   v   k   h   w   l   e   n   g   a   e

----.----+----.----+----.----+----.----+----.----+----.----+----.----+

M                               B
                        N                               P
                        L                               M
                        1                               1

ATTCAGAGAACAGGGCTGGAGGTAAAACCATTTATTACTAACCCCAGAGCAGTGAAGAAG
----.----+----.----+----.----+----.----+----.----+----.----+   180
TAAGTCTCTTGTCCCGACCTCCATTTTGGTAAATAATGATTGGGGTCTCGTCACTTCTTC i   q   r   t   g   l   e   v   k   p   f   i   t   n   p   r   a   v   k   k

```
CR    M              M          TH
SS    B              A          FN
PA    O              E          IF
61    2              3          11
                                /
TGTACCAGATATATTGACTGTGACCTGAATCGCATTTTTGACCTTGAAAATCTTGGCAAA
----.----+----.----+----.----+----.----+----.----+----.----+    240
ACATGGTCTATATAACTGACACTGGACTTAGCGTAAAAACTGGAACTTTTAGAACCGTTT c  t  r  y  i  d  c  d  l  n  r  i  f  d  l  e  n  l  g  k

----.----+----.----+----.----+----.----+----.----+----.----+

NM                      BN
                 DB                      AS
                 EO                      NP
                 12                      22
                  /
AAAATGTCAGAAGATTTGCCATATGAAGTGAGAAGGGCTCAAGAAATAAATCATTTATTT
----.----+----.----+----.----+----.----+----.----+----.----+    300
TTTTACAGTCTTCTAAACGGTATACTTCACTCTTCCCGAGTTCTTTATTTAGTAAATAAA k  m  s  e  d  l  p  y  e  v  r  r  a  q  e  i  n  h  l  f

----.----+----.----+----.----+----.----+----.----+----.----+

A              TH          M                               S
 V              FN          B                               P
 A              IF          O                               O
 2              11          2                               1
                 /
GGTCCAAAAGACAGTGAAGATTCCTATGACATTATTTTTGACCTTCACAACACCACCTCT
----.----+----.----+----.----+----.----+----.----+----.----+    360
CCAGGTTTTCTGTCACTTCTAAGGATACTGTAATAAAAACTGGAAGTGTTGTGGTGGAGA g  p  k  d  s  e  d  s  y  d  i  i  f  d  l  h  n  t  t  s

```
      MN  A    HBN  M            TH  E   AS              ✓
      NL  P    GSS  N            FN  C   PC              TM
      LA  L    IIP  L            IF  R   YR              RS
      13  1    AH2  1            11  2   11              UE
                                                         91
       /      //                  /      /                ↓
  AACATGGGTGCACTCTTATTCTTGAGGATTCCAGGAATAACTTTTTAATTCAGATGTTT
  ----.----+----.----+----.----+----.----+----.----+----.----+  420
  TTGTACCCCACGTGAGAATAAGAACTCCTAAGGTCCTTATTGAAAAATTAAGTCTACAAA
   n  m  g  c  t  l  i  l  e  d  s  r  n  n  f  l  i  q  m  f

----.----+----.----+----.----+----.----+----.----+----.----+

✓
       TM                  N              M  F            E
       RS                  L              A  O            C
       UE                  A              E  K            O
       91                  4              2  1            B
        ↓
  CATTACATTAAGACTTCTCTGGCTCCACTACCCTGCTACGTTTATCTGATTGAGCATCCT
  ----.----+----.----+----.----+----.----+----.----+----.----+  480
  GTAATGTAATTCTGAAGAGACCGAGGTGATGGGACGATGCAAATAGACTAACTCGTAGGA
   h  y  i  k  t  s  l  a  p  l  p  c  y  v  y  l  i  e  h  p

----.----+----.----+----.----+----.----+----.----+----.----+

S         M                                               A
       F         N                                               V
       A         L                                               A
       N         1                                               2

TCCCTCAAATATGCGACCACTCGTTCCATAGCCAAGTATCCTGTGGGTATAGAAGTTGGT
  ----.----+----.----+----.----+----.----+----.----+----.----+  540
  AGGGAGTTTATACGCTGGTGAGCAAGGTATCGGTTCATAGGACACCCATATCTTCAACCA
   s  l  k  y │a  t  t  r  s  i  a  k  y  p  v  g  i  e  v  g

```
D              M    M  D       A      E      BMDD                     TM ✓
D              N    N  D       L      C      IBPP                     RS
E              L    L  E       U      R      NONN                     UE
1              1    1  1       1      V      1121                     91
                                             /                          ↓
     CCTCAGCCTCAAGGGGTTCTGAGAGCTGATATCTTGGATCAAATGAGAAAAATGATTAAA
     ----.----+----.----+----.----+----.----+----.----+----.----+      600
     GGAGTCGGAGTTCCCCAAGACTCTCGACTATAGAACCTAGTTTACTCTTTTTACTAATTT p  q  p  q  g  v  l  r  a  d  i  l  d  q  m  r  k  m  i  k

----.----+----.----+----.----+----.----+----.----+----.----+

NN                                              HMHM
            SL                                              INHN
            PA                                              NLAL
            H3                                              P111
            /                                               /
     CATGCTCTTGATTTTATACATCATTTCAATGAAGGAAAAGAATTTCCTCCCTGCGCCATT
     ----.----+----.----+----.----+----.----+----.----+----.----+      660
     GTACGAGAACTAAAATATGTAGTAAAGTTACTTCCTTTTCTTAAAGGAGGGACGCGGTAA h  a  l  d  f  i  h  h  f  n  e  g  k  e  f  p  p  c  a  i

----.----+----.----+----.----+----.----+----.----+----.----+

E                        BSBNXSASSBBHNSB    FF  F   IF
       C                        SESCMMVCESSPCCB    OO  O   TN
       P                        ACAIAAARCAAAIRV    KK  K   AU
       1                        J1J1111111JJ2111   11  1   1H
                           ↓    / /////////// /               /
     GAGGTCTATAAAATTATAGAGAAAGTTGATTACCCCCGGGATGAAAATGGAGAAATTGCT
     ----.----+----.----+----.----+----.----+----.----+----.----+      720
     CTCCAGATATTTTAATATCTCTTTCAACTAATGGGGGCCCTACTTTTACCTCTTTAACGA e  v  y  k  i  i  e  k  v  d  y  p  r  d  e  n  g  e  i  a
                                                              ┌────────┐
                                                              │c693>a  │
     ----.----+----.----+----.----+----.----+----.----+----.--│Y231>X  │
                                                              └────────┘
```

FIG. 7(d)

```
          S     PBMDD      F              ESASBBSBXBNMDDB
          F     SIBPP      O              CEPCSSFIHALBPPI
          C     TNONN      K              RCYRAAANOMAONNN
          1     11121      1              2111JJN12141211
          /                                 ///  ////////
          GCTATCATCCATCCTAATCTGCAGGATCAAGACTGGAAACCACTGCATCCTGGGGATCCC
          ----.----+----.----+----.----+----.----+----.----+----+   780
          CGATAGTAGGTAGGATTAGACGTCCTAGTTCTGACCTTTGGTGACGTAGGACCCCTAGGG a    i    i    h    p    n    l    q    d    q    d    w    k    p    l    h    p    g    d    p

----.----+----.----+----.----+----.----+----.----+----.----+
                    ✓                    ↓
          N         TM          B        MDBBBDBMA  BBAB       CR          CR
          L         RS          B        BPBSPPIBL  SSCS       SS          SS
          A         UE          V        ONSCUNNOW  ILIM       PA          PA
          3         91          2        121911122  Y112       61          61
          /                     /  ////             ///
          ATGTTTTTAACTCTTGATGGGAAGACGATCCCACTGGGCGGAGACTGTACCGTGTACCCC
          ----.----+----.----+----.----+----.---+----.----+----.----+   840
          TACAAAAATTGAGAACTACCCTTCTGCTAGGGTGACCCGCCTCTGACATGGCACATGGGG
                                                 ↵
          m    f    l    t    l    d    g    k    t    i    p    l    g    g    d    c    t    v    y    p

----.----+----.----+----.----+----.----+----.----+----.----+
          SM        HIFA                  H       A
          PN        ATNC                  I       L
          OL        EAUI                  N       U
          11        31H1                  3       1
          /         *  //                         *
          GTGTTTGTGAATGAGGCCGCATATTACGAAAAGAAAGAAGCTTTTGCAAAGACAACTAAA
          ----.----+----.----+----.----+----.----+----.----+----.----+   900
          CACAAACACTTACTCCGGCGTATAATGCTTTTCTTTCTTCGAAAACGTTTCTGTTGATTT v    f    v    n    e    a    a    y    y    e    k    k    e    a    f    a    k    t    t    k
                                                                                                    ┌─────┐
                                                                                                    │a854>c│
          ----.----+----.----+----.----+----.----+----.----+----.----+                              │E285>A│
                                                                                                    └─────┘
```

FIG. 7(e)

```
    S              B              HIF     E                                A
    P              B              NTN     C                                L
    O              V              FAU     1                                U
    1              1              31H     5                                1        ┌─────────┐
                   *                /                                               │ c914>a  │
CTAACGCTCAATGCAAAAAGTATTCGCTGCTGTTTACATTAGAAATCACTTCCAGCTTAC                        │ A305>E  │
----.----+----.----+----.----+----.----+----.----+----.----+  960                   └─────────┘
GATTGCGAGTTACGTTTTTCATAAGCGACGACAAATGTAATCTTTAGTGAAGGTCGAATG l  t  l  n  a  k  s  i  r  c  c  l  h  .  k  s  l  p  a  y

----.----+----.----+----.----+----.----+----.----+----.----+
                                                      ✓
                          RM              A       ATM
                          MA              L       FRS
                          AE              U       LUE
                          11              1       291
                            /                       /
ATCTTACACGGTGTCTTACAAATTCTGCTAGTCTGTAAGCTCCTTAAGAGTAGGGTTGTG
----.----+----.----+----.----+----.----+----.----+----.----+  1020
TAGAATGTGCCACAGAATGTTTAAGACGATCAGACATTCGAGGAATTCTCATCCCAACAC i  l  h  g  v  l  q  i  l  l  v  c  k  l  l  k  s  r  v  v

----.----+----.----+----.----+----.----+----.----+----.----+

B    A    RM                   H         D         S
             S    L    MA                   N         D         F
             P    U    AE                   F         E         A
             W    1    11                   3         1         N
                        /
CCTTATTCAACTGCATACATAGCTCCTAGCACAGTGCCTTATTCGGTAGGCATCTAAGCA
----.----+----.----+----.----+----.----+----.----+----.----+  1080
GGAATAAGTTGACGTATGTATCGAGGATCGTGTCACGGAATAAGCCATCCGTAGATTCGT p  y  s  t  a  y  i  a  p  s  t  v  p  y  s  v  g  i  .  a

```
           √      √    √                √
           TM    ATM  PATM             TDM       E                        A
           RS    SRS  ASRS             RRS       C                        L
           UE    EUE  CEUE             UAE       R                        U
           91    191  1191             911       V                        1
           /      //   ///              /
AATTTCTTAAATTAATTAATATATCTTTAAAGATATCATATTTTATGTATGTAGCTTATT
----.----+----.----+----.----+----.----+----.----+----.----+    1140
TTAAAGAATTTAATTAATTATATAGAAATTTCTATAGTATAAAATACATACATCGAATAA n  f  l  n  .  l  i  y  l  .  r  y  h  i  l  c  m  .  l  i

----.----+----.----+----.----+----.----+----.----+----.----+

X                                  N              A
              M                                  L              L
              N                                  A              U
              1                                  3              1

CAAAGAAGTGTTTCCTATTTCTATATAGTTTATTATACATGATACTTGGGTAGCTCAACA
----.----+----.----+----.----+----.----+----.----+----.----+    1200
GTTTCTTCACAAAGGATAAAGATATATCAAATAATATGTACTATGAACCCATCGAGTTGT q  r  s  v  s  y  f  y  i  v  y  y  t  .  y  l  g  s  s  t

----.----+----.----+----.----+----.----+----.----+----.----+

√                                                     √
           TM                                                    TM
           RS                                                    RS
           UE                                                    UE
           91                                                    91
           /                                                     /
TTCTTAATAAACAGCCTTTGTATTCAGAATATAAAATTGAAATAGATATATATAAAGTTA
----.----+----.----+----.----+----.----+----.----+----.----+    1260
AAGAATTATTTGTCGGAAACATAAGTCTTATATTTTAACTTTATCTATATATATTTCAAT f  l  i  n  s  l  c  i  q  n  i  k  l  k  .  i  y  i  k  l

----.----+----.----+----.----+----.----+----.----+----.----+

AAAAAAAAAAAAAAAAAA
----.----+----.--     1277
TTTTTTTTTTTTTTTTTT k  k  k  k  k  k

```
                        v-21                    v-1
      TCTTCTGAAT TGCAGAAATC AGATAAAAAC TACTTGGTGA v19
    A ATG ACT TCT TGT CAC ATT GCT GAA GAA CAT ATA CAA
      Met Thr Ser Cys His Ile Ala Glu Glu His Ile Gln
              ^3          ^6          ^9          ^12 v39                        v59
      AAG GTT GCT ATC TTT GGA GGA ACC CAT GGG AAT GAG
      Lys Val Ala Ile Phe Gly Gly Thr His Gly Asn Glu
              ^15         ^18         ^21         ^24 v79                         v99
      CTA ACC GGA GTA TTT CTG GTT AAG CAT TGG CTA GAG
      Leu Thr Gly Val Phe Leu Val Lys His Trp Leu Glu
              ^27         ^30         ^33         ^36 v119                       v139
      AAT GGC GCT GAG ATT CAG AGA ACA GGG CTG GAG GTA
      Asn Gly Ala Glu Ile Gln Arg Thr Gly Leu Glu Val
              ^39         ^42         ^45         ^48 v159
      AAA CCA TTT ATT ACT AAC CCC AGA GCA GTG AAG AAG
      Lys Pro Phe Ile Thr Asn Pro Arg Ala Val Lys Lys
              ^51         ^54         ^57         ^60 v199
      TGT ACC AGA TAT ATT GAC TGT GAC CTG AAT CGC ATT
      Cys Thr Arg Tyr Ile Asp Cys Asp Leu Asn Arg Ile
              ^63         ^66         ^69         ^72 v219                       v239
      TTT GAC CTT GAA AAC CTT GG GTAAGACTATGCTTTGTAT
      Phe Asp Leu Glu Asn Leu Gly
              ^75         ^78 v259                   v279
      TGTATATGTATTGGATGTTCTGTGAAAGTGGTAGGTGTGT
```

FIG. 8

```
           v-42         v-32         v-22         v-12
      TATTATCTCA  GGCACAGATG  TTGTTCATCT  TTTTCTTTCT v-2              v8              v18
      GGTTATAACATG  C AAA AAA ATG TCA GAA GAT TTG CCA TAT
                      Lys Lys Met Ser Glu Asp Leu Pro Tyr
                     ^80 v28           v38           v48           v58
      GAA GTG AGA AGG GCT CAA GAA ATA AAT CAT TTA TTT
      Glu Val Arg Arg Ala Gln Glu Ile Asn His Leu Phe v68           v78           v88           v98
      GGT CCA AAA GAC AGT GAA GAT TCC TAT GAC ATT ATT
      Gly Pro Lys Asp Ser Glu Asp Ser Tyr Asp Ile Ile v108          v118          v128
      TTT GAC CTT CAC AAC ACC ACC TCT AAC ATG GGG TGC
      Phe Asp Leu His Asn Thr Thr Ser Asn Met Gly Cys v138          v148          v158          v168
      ACT CTT ATT CTT GAG GAT TCC AGG AAT AAC TTT TTA
      Thr Leu Ile Leu Glu Asp Ser Arg Asn Asn Phe Leu v178          v188          v198
      ATT CAG ATG TTT CAT TAC ATT AAG GTAATGTT
      Ile Gln Met Phe His Tyr Ile Lys
                                     ^144 v208         v218         v228
      AATGTTATTA  ATTTATAAGT  CAGCAAAGGA CTTG
```

FIG. 9

```
            v-37           v-27            v-17           v-7
     AACATACGGG TTTTTACCCA AGAAAGACGT TTTTGATTTT v3              v13            v23
     TTTCAG ACT TCT CTG GCT CCA CTA CCC TGC TAC GTT
            Thr Ser Leu Ala Pro Leu Pro Cys Tyr Val
                     ^3           ^6           ^9 v33             v43            v53             v63
     TAT CTG ATT GAG CAT CCT TCC CTC AAA TAT GCG ACC
     Tyr Leu Ile Glu His Pro Ser Leu Lys Tyr Ala Thr
     ^12             ^15            ^18             ^21 v73             v83            v93
     ACT CGT TCC ATA GCC AAG TAT CCT GTG G    GTAA
     Thr Arg Ser Ile Ala Lys Tyr Pro Val
     ^24             ^27            ^30 v103            v113           v123            v133
     GTCATAGTTC CCACTGTCAT AAGTCAATAA AATATGTCCT v143            v153
     AGGTGAAACT CAGACA
```

FIG. 10

```
              v-30          v-20          v-10
        TACTTATATA AATGTGACTAT TCTGTGGTTC TGTACGTAG   G v10           v20           v30
    T ATA GAA GTT GGT CCT CAG CCT CAA GGG GTT CTG AGA
      Ile Glu Val Gly Pro Gln Pro Gln Gly Val Leu Arg
      ^177 v40           v50           v60           v70
    GCT GAT ATC TTG GAT CAA ATG AGA AAA ATG ATT AAA
    Ala Asp Ile Leu Asp Gln Met Arg Lys Met Ile Lys v80           v90          v100
    CAT GCT CTT GAT TTT ATA CAT CAT TTC AAT GAA G    GTAAG
    His Ala Leu Asp Phe Ile His His Phe Asn Glu
                                                ^211 v120         v130         v140         v150
        TAA TAATGAAGGT AACGTTATCA AACTTAACCA CCAAACATTT v160         v170         v180
        AAATAAGAAT TGGAACGTGG GTCAGA
```

FIG. 11

```
        v-38           v-28           v-18           v-8
GGAGAGATCT TTTTAGTTGG CATTGATACA TATTGTTTT v2             v12            v22
GTCATAG GA AAA GAA TTT CCT CCC TGC GCC ATT GAG
        Gly Lys Glu Phe Pro Pro Cys Ala Ile Glu
        ^212 v32            v42            v52            v62
GTC TAT AAA ATT ATA GAG AAA GTT GAT TAC CCC CGG
Val Tyr Lys Ile Ile Glu Lys Val Asp Tyr Pro Arg v72            v82            v92
GAT GAA AAT GGA GAA ATT GCT GCT ATC ATC CAT CCT
Asp Glu Asn Gly Glu Ile Ala Ala Ile Ile His Pro v102           v112           v122           v132
AAT CTG CAG GTAA CATTTGTTCT TTCTTTAAAA TGTTGAAAAT
Asn Leu Gln
        ^248 v152           v162           v172           v182
AATAATGCTG TACCTTTGAA TAGAAGTTTA TAGCTCATAC

AGGA
```

FIG. 12

```
                v-65           v-55           v-45           v-35
         GTCTAGAGTC   TGAGATAAAT   TTTTAGAGGA   GAAAAACCAA v-25           v-15           v-5            v5
         ATATAATATA   TTTATTTTGA   TTGTTTCCTG   AGAG GAT CAA GAC
                                                     Asp Gln Asp
                                                     ^249
```

```
              v15             v25             v35
       TGG AAA CCA CTG CAT CCT GGG GAT CCC ATG TTT TTA
       Trp Lys Pro Leu His Pro Gly Asp Pro Met Phe Leu v45             v55             v65             v75
       ACT CTT GAT GGG AAG ACG ATC CCA CTG GGC GGA GAC
       Thr Leu Asp Gly Lys Thr Ile Pro Leu Gly Gly Asp v85             v95             v105
       TGT ACC GTG TAC CCC GTG TTT GTG AAT GAG GCC GCA
       Cys Thr Val Tyr Pro Val Phe Val Asn Glu Ala Ala v125            v135            v145
       TAT TAC GAA AAG AAA GAA GCT TTT GCA AAG ACA ACT
       Tyr Tyr Glu Lys Lys Glu Ala Phe Ala Lys Thr Thr v155            v165            v175            v185
       AAA CTA ACG CTC AAT GCA AAA AGT ATT CGC TGC TGT
       Lys Leu Thr Leu Asn Ala Lys Ser Ile Arg Cys Cys v195            v205            v215
       TTA CAT TAG AAATCA CTTCCAGCTT ACATCTTACA
       Leu His ter
               ^313
```

```
     v225         v235         v245         v255
     CGGTGTCTTA   CAAATTCTGC   TAGTCTGTAA   GCTCCTTAAG v265
     AGTAGGGTT
```

FIG.13

ASPARTOACYLASE GENE, PROTEIN, AND METHODS OF SCREENING FOR MUTATONS ASSOCIATED WITH CANAVAN DISEASE

This application is a continuation of PCT/US94/07430, filed Jul. 5, 1994, which was a continuation-in-part of U.S. Ser. No. 08/128,020, filed Sep. 29, 1993.

BACKGROUND OF THE INVENTION

Canavan disease (CD), or spongy degeneration of brain, is an autosomal recessive leukodystrophy associated with mental retardation, megalencephaly, hypotonia and death, usually in the first decade of life. Brain histology in CD is characterized by spongy degeneration of white matter with astrocytic swelling and elongated mitochondria[1-5]. Canavan disease is more prevalent in Jewish people of Ashkenazi origin[3-5]. Matalon et al. (1988) described aspartoacylase deficiency as the basic biochemical defect in CD[6]. Since the initial report, 145 patients have been diagnosed with CD at a single center, suggesting that CD is more prevalent than previously thought[10-12]. Aspartoacylase deficiency in CD has also been reported by other investigators[13,14].

The deficiency of aspartoacylase in CD leads to excessive excretion of NAA in urine and its accumulation in brain[6, 9-11]. Aspartoacylase in brain has been localized to white matter associated with myelin tracks[16]. How aspartoacylase and the hydrolysis of NAA are involved in keeping white matter intact is not clear. It is also not understood how the deficiency of aspartoacylase leads to the pathogenesis seen in CD.

Aspartoacylase has been purified and characterized from bovine brain and from other bovine and human sources[16]. Biochemical and immunochemical studies suggest that aspartoacylase has been conserved during evolution. Aspartoacylase activity has been found in a variety of mammalian tissues, including kidney, brain white matter, adrenal glands, lung, liver and cultured skin fibroblasts. Brain grey matter and blood constituents do not have any detectable aspartoacylase activity (Kaul et al., unpublished studies).

Aspartoacylase specifically hydrolyses N-acetyl-L-aspartic acid (NAA) to aspartate and acetate[7,8]. Stereospecificity of aspartoacylase towards L-analog of NAA has been well documented. The D-analog of NAA acts as a weak inhibitor of NAA hydrolysis by aspartoacylase. Studies have suggested that the carbon backbone of NAA is involved in interaction with the substrate binding site of aspartoacylase; and that the substitutions at α and β carboxyl groups of aspartate moiety do not have any effect on hydrolysis of NAA by aspartoacylase[16].

The diagnosis of CD is now routinely made by quantitation of NAA in urine and estimation of aspartoacylase activity in cultured skin fibroblast[12]. The level of aspartoacylase activity found in direct chorionic villi cells or in cultured chorionic villi cells and amniocytes is about 2 orders of magnitude lower than that found in normal cultured skin fibroblasts. Due to the low aspartoacylase activity in chorionic villi cells and amniocytes, the prenatal diagnosis of CD using aspartoacylase assay is not satisfactory[15].

Due to the devastating nature of this genetic disease, there is an urgent need for better diagnostic methods for early detection of the disease, both pre- and postnatally, and screening methods to detect genetic carriers of the disease to allow informed genetic counseling for prospective parents. Additionally, there is a critical need for an effective treatment, and even more preferably, a cure for the underlying biochemical defect.

SUMMARY OF THE INVENTION

The present invention discloses the isolation and expression of human ASP cDNA, and thus provides the gene and protein encoded by the gene. In particular, the invention provides an isolated nucleic acid molecule comprising:

(a) a nucleic acid sequence encoding a human aspartoacylase polypeptide;

(b) a nucleic acid sequence complementary to nucleic acid sequence (a); or (c) a nucleic acid sequence at least 16 nucleotides in length capable of hybridizing, under stringent hybridization conditions, with one of said nucleic acid molecules (a) or (b).

More particularly, the invention provides a nucleic acid molecule described in (a), above, comprising:

(i) a DNA molecule having the DNA sequence of FIG. 1 from DNA position +1 to +891;

(ii) a DNA molecule encoding a normal human aspartoacylase polypeptide having the amino acid sequence of FIG. 1 from amino acid position +1 to +313;

(iii) a DNA molecule having a sequence of a fragment of the DNA sequence of FIG. 1, or a sequence complementary thereto, and including at least 16 sequential nucleotides;

(iv) a DNA molecule having a sequence of a fragment of the DNA sequence of FIG. 1 and including at least 16 sequential nucleotides, and which encodes a fragment of the amino acid sequence of FIG. 1; or (v) a DNA molecule encoding an epitope of the amino acid sequence of FIG. 1 between positions +1 to +313, and encoded by at least 18 sequential nucleotides.

In addition, the invention provides allelic or mutant versions of the above DNA molecules (i)-(v) wherein they are modified in at least one nucleotide position as compared with the sequence of FIG. 1, corresponding to the sequence of a naturally-occurring allele of human aspartoacylase having an altered biological activity.

In another aspect, the invention provides an isolated normal aspartoacylase polypeptide capable of hydrolyzing N-acetyl-aspartic acid to aspartate and acetate. In particular, the invention provides a normal aspartoacylase polypeptide having the amino acid sequence of FIG. 1 from amino acid position +1 to +313 as well as a mutant aspartoacylase polypeptide having either an altered ability of hydrolyze N-acetyl-aspartic acid to aspartate and acetate or incapable of hydrolyzing N-acetyl-aspartic acid to aspartate and acetate.

In another aspect of the invention, in view of the identification of a base change in the human ASP encoded aspartoacylase, which base change is present in 85% of Canavan alleles, the invention provides a means of identifying DNA sequences containing the mutation. Therefore, the invention additionally provides a means of diagnosing the disease in patients, and identifying carriers of the genetic defect. This aspect of the invention includes methods for screening a potential Canavan disease carrier or patient for the presence of an identified mutation and/or a different mutation in an aspartoacylase gene; for example:

hybridization assays, comprising (a) isolating genomic DNA from said potential Canavan disease carrier or patient, (b) hybridizing a DNA probe onto said isolated genomic DNA, said DNA probe spanning said mutation in said aspartoacylase gene, wherein said DNA probe is capable of detecting said mutation, (c) treating said genomic DNA to determine the presence or absence of said DNA probe and thereby indicating the presence or absence of said aspartoacylase mutation;

restriction fragment length polymorphism assays, comprising (a) isolating genomic DNA from said potential Canavan disease carrier or patient, (b) determining the presence or absence of a restriction endonuclease site in the gene, the presence or absence of which thereby indicates the presence or absence of said aspartoacylase mutation;

PCR assays, comprising (a) isolating genomic DNA from said potential Canavan disease carrier or patient, (b) determining the mobility of heteroduplex PCR products in polyacrylamide gels, the mobility of which thereby indicates the presence or absence of said aspartoacylase mutation; and immunoassays, comprising (a) providing a biological sample of the subject to be screened; and (b) submitting the sample to an assay for detecting in the biological sample the presence of a normal aspartoacylase gene, a mutant aspartoacylase gene, normal aspartoacylase polypeptide, mutant aspartoacylase polypeptide, or mixtures thereof.

In the above methods of screening (assays), either the presence of the normal or mutant aspartoacylase polypeptide or nucleic acid coding for said polypeptide can be detected. For each of the assays, kits are provided for carrying out the methods of the invention. These kits include nucleic acids, polypeptides and antibodies of the present invention, including fragments such as nucleic acid probes, oligopeptide epitopes and antibody fragments such as F(ab')$_2$ fragments.

In related aspects of the invention, genetic constructs and methods for making the nucleic acids, polypeptides and antibodies of the invention are provided, including cloning vectors, host cells transformed with cloning vectors and hybridomas; pharmaceutical preparations containing normal polypeptides for administering to patients to provide therapy to replace the mutant polypeptide; nucleic acid constructs suitable for administering to patients to provide a (preferably permanent) genetic therapy; methods for making the nucleic acids, polypeptides and antibodies of the present invention, including fragments such as nucleic acid probes, oligopeptide epitopes and antibody fragments such as F(ab')$_2$ fragments; and animals transformed with normal and mutant aspartoacylase genes to provide animal models for study of CD and related genetic diseases.

It will be appreciated by a skilled worker in the art that the identification of the genetic defect in a genetic disease, coupled with the provision of the DNA sequences of both normal and disease-causing alleles, provides the full scope of diagnostic and therapeutic aspects of such an invention as can be envisaged using current technology.

BRIEF DESCRIPTION OF THE DRAWINGS

Various other objects, features and attendant advantages of the present invention will be more fully appreciated as the same becomes better understood when considered in conjunction with the accompanying drawings, wherein:

FIG. 1 depicts the nucleotide (SEQ ID NO:1) and predicted amino acid (SEQ ID NO:2) sequence of human ASP encoded transcript and protein. The cDNA is 1,435 bp and the initiator "atg" marks base 1 of coding sequence. The polyadenylation signal sequences are shaded. Also shown are the 18 base poly(A) tail. Amino acid sequence predicted from the human ASP cDNA is depicted as single letter code and initiator amino acid residue M is residue 1. There are several in frame termination codons present in human ASP cDNA upstream of the initiator atg codon. The potential N-glycosylation site is shown in bold type and marked by an asterisk (*). The numbers on left show amino acid residues while those on right are nucleotide base position.

FIG. 2 depicts the alignment of human (HLASP) (SEQ ID NO:2) and bovine (BASPCDN) (SEQ ID NO:4) ASP encoded protein sequence using the AALIGN program (Gap penalty 4, Deletion penalty 12, PAMfile STANDARD.PAM) in Lasergene software package from DNAstar (Madison, Wis.). The human and bovine aspartoacylase amino acid sequences share 92.3% identity in 313 aa overlap. Consensus amino acid sequence (SEQ ID NO:3) motifs predicted to be involved in catalytic center of aspartoacylase are shown as shaded areas. The potential N-glycosylation site is marked by an asterisk (*), and phosphorylation sites are highlighted as shadows.

FIG. 7 is a restriction map of the structural gene sequences of ASP.

FIG. 8 is the DNA and amino acid sequence (SEQ ID NO:63) of human ASP (also called ASPA) Exon 1 and its boundaries. The bases in italics are the 5' untranslated sequence, which are part of the cDNA sequence. The redlined (▓) bases are the intron 1 sequences, starting with the splice donor site. The sequence spans the region amplified for detecting mutations in Exon 1 and its boundaries.

FIG. 9 is the DNA and amino acid sequence (SEQ ID NO:64) of human ASP (also called ASPA) Exon 2 and its boundaries. The redlined (▓) bases are parts of the intron 1 and 2 sequences around Exon 2. The sequence spans the region amplified for detecting mutations in Exon 2 and its boundaries.

FIG. 10 is the DNA and amino acid sequence (SEQ ID NO:65) of human ASP (also called ASPA) Exon 3 and its boundaries. The redlined (▓) bases are parts of the intron 2 and 3 sequences around Exon 3. The sequence spans the region amplified for detecting mutations in Exon 3 and its boundaries.

FIG. 11 is the DNA and amino acid sequence (SEQ ID NO:66) of human ASP (also called ASPA) Exon 4 and its boundaries. The redlined (▓) bases are parts of the intron 3 and 4 sequences around Exon 4. The sequence spans the region amplified for detecting mutations in Exon 4 and its boundaries.

FIG. 12 is the DNA and amino acid sequence (SEQ ID NO:67) of human ASP (also called ASPA) Exon 5 and its boundaries. The redlined (▓) bases are parts of the intron 4 and 5 sequences around Exon 5. The sequence spans the region amplified for detecting mutations in Exon 5 and its boundaries.

FIG. 13 is the DNA and amino acid sequence (SEQ ID NO:68) of human ASP (also called ASPA) Exon 6 and its boundaries. The redlined (▓) bases are parts of the intron 5 and 6 sequences around Exon 6. The sequence spans the region amplified for detecting mutations in Exon 6 and its boundaries.

GENERAL DISCUSSION

Figure 3:
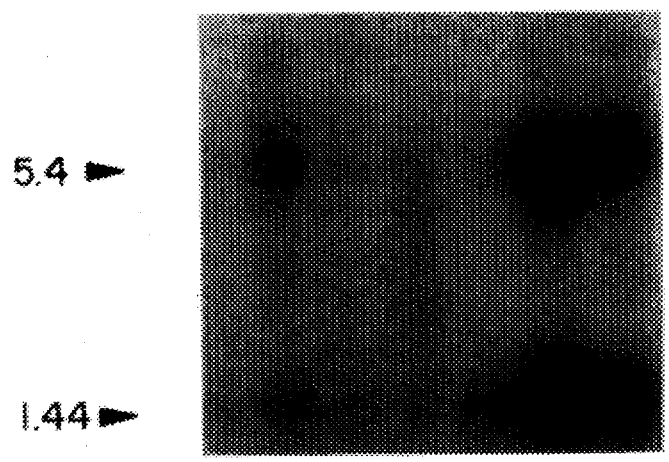
FIG. 3 depicts an autoradiogram of Northern blot analysis of poly(A)$^+$ RNA isolated from various human tissues. Two µg of poly(A)$^+$ RNA from each tissue were fractionated on agarose gel and blotted on nylon membrane and blots were hybridized to human cDNA under stringent conditions. The human poly(A)$^+$ RNAs are from; 1: heart, 2: brain, 3: placenta 4: lung, 5: liver, 6: skeletal muscle and 7: kidney.

The discovery of aspartoacylase deficiency and N-acetylaspartic aciduria has for the first time offered a definite diagnosis for CD without the need for brain biopsy (for review, see Matalon et al., 1993)[12]. The spongy degeneration of white matter in CD strongly suggests that hydrolysis of NAA by aspartoacylase plays a significant role in the maintenance of intact white matter.

Canavan disease is the only known genetic disorder which is caused by a defect in the metabolism of a small metabolite, NAA, synthesized exclusively in the brain[22,23] in a cell specific manner[24–26]. Since the initial discovery of NAA in brain[27], its biological role has remained unknown[28–32]. The stable level of NAA in brain has made it a useful marker in $^1$H NMR spectroscopy of brain (for review, see Birken and Oldendorf, 1989)[33]. Significantly reduced levels of NAA have been reported in non-CD focal or generalized demyelinating disorders[34], Huntington disease[35], HIV-seropositive individuals[36], acute stroke[37], myodystrophic mice[38] and mouse model of scrapie[39]. While such decrease in NAA level has been proposed as a measure of neuronal loss, it is not specific for any particular pathology. The accumulation of NAA, and dystrophy of white matter, in brain of patients with CD is highly specific and the elevated NAA level has been demonstrated both by biochemical and as well as $^1$H NMR spectroscopy of brain[9,10,16,34].

Aspartoacylase is present in a variety of tissues, and in most of the tissues tested, (Kaul et al., unpublished studies). Northern blot analysis has confirmed the expression of human ASP in the tissues tested so far. However, the enzyme seems to have a unique role in maintaining a homeostatic balance of NAA level, particularly in the white matter of brain. The disturbance of this equilibrium, as seen in CD, somehow leads to spongy degeneration of the white matter. The pathology seen in CD is apparently co-localized to the regions of brain that express aspartoacylase activity[16]. The grey matter, despite several fold increased levels of NAA[16], is spared of any significant pathological changes in CD. Without wishing to be bound by theory, it is believe that the critical role of NAA in brain function and biology is manifested through the action of aspartoacylase.

Since the pathology in CD is observed only in brain, it is suggested that aspartoacylase in tissues other than brain acts as scavenger of NAA from body fluids. The relative abundance of two human ASP transcripts is apparently regulated in a tissue dependent manner. The choice of polyadenylation site, and/or alternative splicing of pre-mRNA, as reason for the two transcripts is plausible. The polyadenylation signal or/and alternative splicing may provide an additional mode of regulating gene expression[20].

Hydrolysis of NAA by aspartoacylase is highly specific. N-Acetyl derivatives of amino acids other than aspartic acid are not hydrolyzed by aspartoacylase. In contrast, NAA is not hydrolyzed by aminoacylase I, an enzyme that hydrolyzes N-acetyl derivatives of all other amino acid, including N-acetyl-L-glutamic acid[7,8].

Human ASP encoded transcript and protein apparently do not share any homology with the human aminoacylase I cDNA[21]. Human and bovine aspartoacylase have sequences that have homology to the catalytic domain sequence motifs reported in esterases and other related hydrolytic enzymes[19]. The invariable amino acid residues histidine (H) and glutamic acid (E) involved in catalysis by esterases are present in the consensus sequence motifs GGTHGNE (SEQ ID NO:10) and VNEAAYY (SEQ ID NO:11) in aspartoacylase. The inhibition of aspartoacylase activity by diisopropyl fluorophosphate, (Kaul, unpublished data), further suggests that a serine (S) amino acid residue is involved at the active site. It is therefore proposed that aspartoacylase has an esterase-like activity and that its catalytic domain involves a triad of S, H and E amino acid residues. The E285 amino acid residue in wild type aspartoacylase is indeed part of the VXEXXXY (SEQ ID NO:12) sequence motif involved in catalysis by esterases, and is conserved in bovine aspartoacylase. The substitution of the amino acid residue E with A residue should lead to the inactivation of aspartoacylase, as is observed in CD in patients with E285>A mutation.

The mutation data is based on a sample of 17 unrelated pedigrees of Ashkenazi Jewish descent. Since a854>c base change in ASP has not been observed in any of the 168 normal chromosomes analyzed, it supports the conclusion that this base change is indeed a mutation causing CD. The apparently predominant nature of a854>c point mutation, detected in 85% of the Canavan alleles, further suggests a founder effect of this mutation in the Jewish population. Such a predominant mutation can facilitate the study of epidemiology of CD in the population at risk. Mutation analysis can also be used for reliable screening for carriers of the genetic defect, as well as prenatal diagnosis.

In addition, other mutations in the ASP gene have been identified which are also associated with Canavan disease:

One is a c693>a mutation, which results in the codon change TAC>TAA, which results in a translation error of Y231>X; thus, this mutation causes premature termination of the polypeptide chain at the location where a tyrosine residue is supposed to be. This is a "nonsense" mutation.

Another allele which has been identified is a c914>a change, which results in the codon change GCA>GAA, which in turn results in the missense mutation A305>E, substituting a glutamic acid for an alanine residue.

Other alleles which have been identified include the following:

t47>c (I16>T)
c342>a (D114>E)
g368>a (G23>E)
433 -2(A>G) IVS2
t454>c (C152>Y)
g455>a (C152>Y)
c502>t (R168>C)
c541>a (P181>T)
876 del agaa (4 bp deletion)
t928>g (C310>G)

Thus, several mutations have been identified which are involved in Canavan disease, including a missense mutation which has been localized in the predicted catalytic domain of aspartoacylase, indicating the underlying genetic defect in the disease in the majority of patients. Therefore, the present invention also provides methods of treating and curing Canavan disease, comprising administering therapeutically effective amounts of a biologically active protein or a biologically active fragment thereof, or drugs which overcome the biological deficit caused by the genetic defect (the pharmacological approach), or administering therapeutically effective amounts of a nucleotide sequence coding for a biologically active protein or a biologically active fragment thereof, which nucleic acid allows the production of a biologically effective aspartoacylase protein in the affected cells (the genetic therapy approach).

In the disclosure which follows, it will be appreciated by the skilled worker that implementing the various utilities disclosed herein, as well as others, which can be derived from the provision of the DNA sequence for aspartoacylase of present invention, e.g., screening of carriers, diagnosis of disease and therapeutic applications, including polypeptide and gene therapies, are routinely achievable in view of the guidance of this disclosure, as well in view of conventional knowledge. Thus, the numerous routine protocols for conducting these various applications are also well known. Thus, for example, various other genes which are implicated in genetic defects are disclosed in the prior art, as are examples of various utilities for these other genes, and the genes, polypeptides, antibodies, etc., of the present invention, can be prepared analogously; similarly, the methods of the present invention can be conducted analogously.

Definitions

As used herein, "aspartoacylase" means the polypeptide coded for by the ASP gene, e.g., in humans. This definition thus includes the protein as isolated from human or animal sources, as produced by recombinant organisms and as chemically or enzymatically synthesized according to techniques routine in the art. This definition is understood to include the various polymorphic forms of the polypeptide wherein amino acid substitutions in the non-critical or variable regions of the sequence do not affect the essential functioning of the polypeptide or its secondary or tertiary structure. This definition includes the polypeptide which, in its normal condition, is present in non-Canavan disease patients or carriers and wherein it performs its normal functions.

As used herein, "mutant aspartoacylase" or "allelic variant of aspartoacylase" or "Canavan aspartoacylase" means the polypeptide coded for by an ASP gene which is highly analogous to aspartoacylase in terms of primary, secondary and tertiary structure, but wherein one or more amino acid substitutions, and/or deletions and/or insertions result in impairment of its essential function, so that organisms whose brain white matter cells express mutant aspartoacylase rather than normal aspartoacylase demonstrate one or more symptoms of Canavan disease.

As used herein, "Canavan disease" or "CD" refers to the genetic disease autosomal recessive leukodystrophy, defined above.

As used herein, "CD carrier" means a person in apparent health whose chromosomes contain a mutant ASP gene that may be transmitted to that person's offspring.

As used herein, "CD patient" means a person who carries a mutant ASP gene on both chromosomes on which the gene is carried, such that they exhibit the clinical symptoms of Canavan disease.

As used herein, "ASP gene" refers to the gene whose mutant forms are associated with Canavan disease. This definition is understood to include the various sequence polymorphisms that exist, wherein nucleotide substitutions in the gene sequence do not affect the essential function of the gene product. This term primarily relates to an isolated coding sequence, but can also include some or all of the flanking regulatory elements and/or any introns.

As used herein, "stringent hybridization conditions" are defined in accordance with what a skilled worker would understand such conditions to mean, depending on the nucleic acids being hybridized. Thus, stringent hybridization conditions for DNA-DNA hybrids are different from those for DNA-RNA heteroduplexes, and conditions for short (e.g., less than 200 and especially under 100 nucleotides in length) oligonucleotides are generally different than those for long sequences ($\geq 200$ nucleotides). Suitable conditions meeting the requirement of stringency are described in Reference 45. For example, for short oligonucleotide sequences, stringent conditions generally include hybridization at temperatures 5°–10° C. below the $T_m$ for the specific sequence.

As used herein, "an aspartoacylase having altered biological activity" means an aspartoacylase polypeptide having a biological activity which, when expressed in vivo, results in phenotypic effects or symptoms of Canavan disease.

As used herein, "complementary" means a nucleic acid molecule has a sequence which complements a reference template sequence, whereby the two sequences can specifically hybridize. Preferably, the term refers to exact complementarity, e.g., as is found between the two strands of a nucleotide sequence in a naturally-occurring gene.

It will be understood by those of skill in the art that allelic or other sequence variations in the DNA and amino acid sequences of the ASP gene and its product aspartoacylase are included in the present invention. For example, allelic variants which result in aspartoacylase polypeptides having the identical amino acid sequence to the normal or most prevalent variant due to degeneracy of the genetic code are included. Further, allelic variants which result in aspartoacylase having essentially insignificant changes in the non-critical or variable regions of the polypeptide, e.g., not in regions of the polypeptide involved in the biological activity of the polypeptide such as is seen in Canavan disease, are also considered to be equivalents included in the scope of this invention. Such variants include those resulting in amino acid substitutions, e.g., as shown in Table 1, which provide a polypeptide having essentially the same function as the normal polypeptide. In each individual case, the equivalency can be determined by measuring the biological activity of the polypeptide in comparison with the normal polypeptide, e.g., according to the assay described in Reference 16. In contrast, it is more likely that sequence variations which occur inside the consensus sequences described below for esterase catalytic sites, which variations result in amino acid sequences not fitting the consensus sequence, will in turn result in a polypeptide with altered biological activity.

TABLE 1

Generally Equivalent Substitution of Amino Acids in a Polypeptide

| Original Amino Acid | Equivalent Amino Acid |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile Leu |

In general, the functions or the immunological identity may be significantly changed if substituents are selected which are less conservative than the amino acids shown in Table 1. Such significant changes can be achieved by substitutions with amino acids which differ more in their structure and in the functional groups. Significant changes are those having an effect on the three-dimensional structure, e.g., wherein the pleated sheet structure or the helical structure is affected. Also, interactions of the charged and the hydrophobic chains can be affected.

Mutations are defined by the homology of two polypeptides which are compared. The term "homology" comprises similar amino acids (for example, Table 1) and gaps in the sequences of the amino acids (homology=similarity). The polypeptides according to the invention have an amino acid sequence which has a homology of at least 80%, preferably 90%, more preferably 95% and most preferably 98% of the amino acid sequence of FIG. 1.

As previously mentioned, the invention also comprises modifications of the DNA or cDNA. These modified sequences hybridize under stringent conditions with the DNA, which codes the protein according to the invention. The cDNA or DNA has a nucleotide sequence, which has a homology of at least 70%, preferably 80%, more preferably 90% and most preferably 95% with the cDNA or DNA sequence according to the FIG. 1. The homology can be measured by hybridization, as it is described in R. Knippers, Molekulare Genetik (Molecular Genetics), 1982, Third Edition, Georg Thieme Verlag Stuttgart, New York.

The invention also includes polypeptides having post-translational modifications, which are to be understood to mean changes which occur during or after translation. These include glycosylation, formation of disulfide bridges, and chemical modifications of the amino acids, for example, sulfation.

Glycosylation is a basic function of the endoplasmic reticulum and/or the Golgi apparatus. The sequence and the branching of the oligosaccharides are formed in the endoplasmic reticulum and changed in the Golgi apparatus. The oligosaccharides can be N-linked oligosaccharides (asparagine-linked) or O-linked oligosaccharides (serine-, threonine- or hydroxylysine-linked). The form of glycosylation is dependent on the host cell type and on the type from which the corresponding cell type is derived. The extent and the type of glycosylation can be affected by substances, for example as described in European publication EP 0 222 313. The variation of glycosylation can change the function of the protein.

Proteins often form covalent bonds within the chains. These disulfide bridges are produced between two cysteines, whereby the protein is specifically pleated. Disulfide bridges stabilize the three-dimensional structure of the proteins.

Methods for Isolating, Cloning and Expressing the ASP Gene

The methods used to isolate, clone and express the ASP gene disclosed in FIG. 1 are outlined in Examples 1–6, below. However, it is evident to a skilled worker that, given the DNA sequence provided herein, many other means of isolating this gene and other related sequences, e.g., from other humans, including those having allelic variations of the sequence of FIG. 1, e.g., from other libraries, including cDNA libraries from other human tissues as well as genomic libraries, from other species, including those from existing cDNA and genomic libraries as well as those which are commercially available or can be routinely constructed, e.g., according to methods well known in the art, e.g., according to the methods outlined in Sambrook et al.[45], are additionally made available. For example, probes synthesized in accordance with the DNA sequence in FIG. 1 can be used to screen libraries constructed from the DNA isolated from other individuals or other species to find corresponding genes. In particular, given the conserved nature of the gene determined by sequence comparison with the bovine ASP gene, the almost ubiquitous presence of aspartoacylase in many tissue types tested thus far and the ubiquitous presence of NAA in other mammals, it is likely that many other animals contain an equivalent gene.

In general terms, the production of a recombinant form of aspartoacylase can be effected by a wide variety of procedures well known to those of ordinary skill in the art. In particular, the recombinant polypeptide can be produced following the procedures outlined in U.S. Pat. No. 5,227,292 for the neurofibromatosis type 1 gene and protein, especially from column 6, line 12 to column 8, line 2 and references cited therein (the disclosures of which are incorporated by reference herein), except that the procedures are conducted starting with a DNA encoding and aspartoacylase gene instead of an NF1 gene. Suitable promoters, control sequences, vectors, host cells, etc. are routinely determinable, e.g., as disclosed in WO 91/02796, directed to analogous methods for isolation, cloning and expressing the gene for cystic fibrosis, in particular, e.g., from page 95, line 28 to page 100, line 29 and the references cited therein. In particular it is noted that both normal and mutant polypeptides can be produced.

Thus, in view of the disclosure herein of the sequence for the aspartoacylase gene and suitable probes for the gene, aspartoacylase genes can be isolated from any suitable source and routinely be cloned into a suitable cloning vector, and ultimately into an expression vector, i.e., a replicable vector suitable for transforming a host cell and containing the aspartoacylase DNA sequence in operable linkage with suitable control sequences whereby the DNA sequence can be expressed. (Definitions of the terms used in this section, e.g., "operable linkage", "control sequences", etc., have their usual meanings, e.g., as described in U.S. Pat. No. 5,227,292, as well as in WO 93/06244.) The vector is then used to transform a suitable host cell and the host cell is cultured under suitable conditions to effect expression of the DNA sequence into the corresponding polypeptide. The expressed polypeptide is then isolated according to standard techniques well known in the art.

Methods for Isolating the Aspartoacylase Polypeptide

A method for isolating aspartoacylase from bovine brain is outlined in Reference 16, which isolation procedure is fully applicable to other aspartoacylase polypeptides from other tissues in which it is expressed. However, it is evident to a skilled worker, given the ability to produce the cloned aspartoacylase polypeptides in recombinant expression systems of the present invention, that purification from such expression systems can be performed analogously to other purifications from such sources, given the physicochemical properties of the polypeptide, e.g., properties which are revealed by its sequence as disclosed by the present invention, and the teaching of, e.g., Reference 16, as well as utilizing routine experimentation for optimization of results, e.g., yields and activity, from a particular source. For example, WO 91/02796 discloses methods for selecting purification techniques based upon the properties of the polypeptide. Other such techniques are well known in the art. For final purification of the polypeptide, many standard techniques can be utilized, e.g., ion exchange chromatography, gel permeation chromatography, adsorption chromatography or isoelectric focusing., immunoaffinity chromatography (see the discussion regarding preparation of antibodies to aspartoacylase), preparative polyacrylamide gel electrophoresis, and high performance liquid chromatography (HPLC).

The homogeneity of the thus-produced aspartoacylase can be determined using standard protein analytical techniques. See, e.g., Sambrook et al.[45]

Preparation of Antibodies to Aspartoacylase

The present invention also provides antibodies which selectively bind to epitopes of aspartoacylase. These antibodies can be produced according to well known techniques in the art, including immunization of suitable antibody-producing animals with whole aspartoacylase polypeptides (including the mutant forms of aspartoacylase) or immunologically-effective fragments thereof, e.g., epitopes, to provide polyclonal antibodies to the polypeptide. Preferably, the antibodies are high affinity antibodies, e.g., having affinities, i.e., dissociation constants, of $10^{-6}$, more preferably $10^{-7}$, $10^{-8}$, $10^{-9}$ or higher. In addition, according to well known techniques such as, e.g., Kohler and Milstein[49], monoclonal antibodies to epitopes of aspartoacylase can also be produced. Still further, antibody fragments, such as F(ab')$_2$ fragments, can be produced and used according to well known methods.

These antibodies or antibody fragments can be used for a variety of purposes. For example, they can be used to purify aspartoacylase from solutions, e.g., fractionated cell supernatants or media containing secreted aspartoacylase from host cells containing the clones gene in an expressible, secreted form. Additionally, the antibodies, or fragments thereof, can be used in a wide variety of immunological assays for the detection of aspartoacylase and its mutants. Thus, these antibodies can be used in the immunoassay-based screening and diagnostic methods of the present invention.

Treatment by Administration of Functional ASP Protein or Fragments Thereof

In a pharmacological approach, treatment of Canavan disease can be performed by replacing the defective aspartoacylase polypeptide with normal polypeptide, by modulating the function of the defective polypeptide or by modifying another step in the pathway in which aspartoacylase participates in order to correct the physiological abnormality.

To be able to replace the defective polypeptide, reasonably large amounts of pure aspartoacylase must be available. Pure aspartoacylase can be obtained as described above from cultured cell systems, e.g., containing cloned and expressed ASP gene. Delivery of the polypeptide to the affected white matter requires its packaging and administration by means which allows the intact polypeptide to cross the blood-brain barrier, e.g., by disrupting the barrier, thereby allowing the polypeptide to pass through it, e.g., according to the methods outlined in U.S. Pat. No. 4,866,042 and references cited therein, or by encapsulating the polypeptide in, e.g., liposomes, whereby the barrier can be crossed without disruption, e.g., according to the methods outlined in WO 91/04014 and references cited therein. Other techniques known in the art for delivery to the affected situs can also be used.

Suitable amounts of polypeptide and regimens of administration, including routes and frequency of administration, for treatment of Canavan disease can be routinely determined by the skilled practitioner. For example, an effective dosage for treatment of a patient who has been diagnosed with Canavan disease will be 0.1 to 100 U/kg, more preferably 0.5 to 60 U/kg, still more preferably 1 to 20 U/kg, most preferably 2 to 10 U/kg of body weight/day, or twice weekly, and which will be optimized for the individual patient, e.g., in analogy with administration of glucocerebrosidase for treatment of Gaucher disease. Optimization of dosage can be determined by monitoring clinical symptoms, as well as measuring the levels of NAA in various body tissues. For example, NMR spectroscopy of the brain can be used to monitor NAA levels in vivo. Effective dosages are those which substantially alleviate the clinical manifestations of Canavan disease.

The aspartoacylase polypeptide can be formulated in conventional ways standard in the art for administration of protein substances. Administration by injection with a pharmaceutically acceptable carrier or excipient, either alone or in combination with another agent, is preferred. Suitable formulations include solutions or suspensions emulsions or solid compositions for reconstitution into injectables. Acceptable pharmaceutical carriers are those which dissolve the aspartoacylase polypeptide or hold it in suspension and which are not toxic to the extent of permanently harming the patient. Those skilled in the art will know, or be able to ascertain with no more than routine experimentation, particular suitable pharmaceutical carriers for this composition. See, for example, the protocols disclosed in U.S. Pat. No. 5,227,292 (see, e.g., column 12, line 1–68).

Treatment by Genetic Therapy

In a preferred therapeutic aspect of the present invention, patients suffering from Canavan disease are provided with a permanent source of normal aspartoacylase polypeptide, i.e., by way of provision of a normal ASP gene, at the appropriate site(s) in the body to partially, substantially or totally relieve the deleterious effects of the genetic defect in the mutant ASP gene. Such somatic gene therapy has been shown to be effective for a number of genes involved in genetic defects. For example, adenosine deaminase deficiency disease has been cured by administration of a normal gene for the defective enzyme. Similarly, the gene coding for aspartoacylase is provided to patients in need of such treatment, i.e., patients suffering from Canavan disease, whereby the deleterious effects of the defective mutant gene are relieved.

Various options are available for effecting genetic therapy, including but not limited to somatic gene therapy at the affected site, e.g., administering a therapeutically effective dosage of the gene to tissues and/or cells in which the gene is needed to prevent disease; whole body somatic therapy, whereby most if not all tissues and/or cells in the body receive a therapeutically effective dosage of the gene, whether or not the disease is manifested in that tissue or cell; and germ line gene therapy, wherein the genetic defect is cured in the reproductive cells of the carrier or patient, whereby that person will only transmit normal and not defective alleles to his or her children.

The preferred gene therapy method for Canavan disease will vary with the patient or carrier to be treated, and can be determined using no more than routine experimentation by the skilled practitioner. In particular, guidance a gene therapy techniques and considerations are disclosed in the series Human Gene Therapy[50]. Introduction of the DNA coding for the normal aspartoacylase into cells in need of this treatment can be through the use of retroviral vectors, non-retroviral vectors such as adenoviral vectors, vaccinia virus herpesvirus, or animal virus vectors such as Moloney murine leukemia virus and SV40 virus. Protocols for such gene therapy are disclosed in WO 91/02796 (page 106, line 15-page 108, line 9). Particular protocols can be optimized as needed.

The methods of delivery of the genetic therapeutic material to a particular location, e.g, the white matter of the brain, are also disclosed in the various references cited herein, and in particular in U.S. Pat. No. 4,866,042 and references cited therein, and in WO 91/04014 and references cited therein.

Other Treatments

Other treatment regimes can also be facilitated by the present invention. For example, drug therapy providing modulation of the defective aspartoacylase can be developed by using screening methods made possible by the present invention. Cultured cell systems expressing the defective aspartoacylase polypeptide can be used to screen drugs for their effectiveness in vitro for improving the performance of the defective polypeptide. Alternatively, drugs can be designed based upon the disclosed structure of the polypeptide to compensate for the defective structure of the mutant polypeptide. Still further, drugs could be developed which modulate the stability or production of the defective polypeptide in order to compensate for the decreased activity of the mutant polypeptide. These alternatives are discussed in detail in WO 91/02796 with respect to the cystic fibrosis polypeptide, which discussion is fully applicable herein to the aspartoacylase polypeptide.

In addition, the present invention facilitates the development of therapies based on modulation of the amounts of substrate and/or end products of the reaction catalyzed by aspartoacylase. For example, acetate and/or aspartic acid and/or their further metabolites may be administered to compensate for the lack of production of these products, including their further metabolic products, e.g., analogously to the administration of L-DOPA to compensate for the deficiency of tyrosine hydroxylase in Parkinsonism. Alternatively, if the clinical symptoms are caused by excessive buildup of NAA, compounds can be administered to bind, e.g, chelate, NAA, or to competitively inhibit its binding at sites where such binding is causing the clinical symptoms, e.g., analogously to administration of dopamine antagonists in the treatment of amphetamine and drug abuse.

Production of Probes and Primers

Various aspects of the present invention require the use of nucleotide probes and primers which hybridize with nucleic acid sequences of the aspartoacylase gene. Given the sequence of that gene provided herein, it is routine for such molecules to be prepared. See, e.g., the manufacturer's instructions which accompany various commercial PCR amplification equipment and kits (e.g., those of Perkin Elmer Cetus), or nucleic acid synthesizers (e.g., those of Applied Biosystems, Inc., Foster City, Calif.).

Design and selection of suitable probes and primers is routine for the skilled worker. For example, suitable probes for detecting a given mutation include the nucleotide sequence at the mutation site and encompass a sufficient number of nucleotides to provide a means of differentiating a normal from a mutant allele. Suitable probes include those complementary to either the coding or noncoding strand of the DNA. Similarly, suitable PCR primers are complementary to sequences flanking the mutation site. Production of these primers and probes can be carried out in accordance with any one of the many routine methods, e.g., as disclosed in Sambrook et al.[45], and those disclosed in WO 93/06244 for assays for Goucher disease.

In general, suitable probes and primers will comprise, at a minimum, an oligomer at least 16 nucleotides in length, since, as disclosed in Reference 45 (page 11.7), calculations for mammalian genomes indicate that for an oligonucleotide 16 nucleotides in length, there is only one chance in ten that a typical cDNA library (complexity≈$10^7$ nucleotides) will fortuitously contain a sequence that exactly matches the sequence of the nucleotide. Therefore, suitable probes and primers corresponding to epitopes are generally 18 nucleotides long, which is the next larger oligonucleotide fully encoding an amino acid sequence (i.e., 6 amino acids in length).

Methods of Pre- and Postnatal Diagnosis and Carrier Screening

By use of nucleotide and polypeptide sequences provided by the present invention, safe, effective and accurate testing procedures are also made available to identify carriers of mutant alleles of aspartoacylase, as well as pre- and postnatal diagnosis of fetuses and live born patients carrying either one or two mutant alleles. This affords potential parents the opportunity to make reproductive decisions prior to pregnancy, as well as afterwards, e.g., if chorionic villi sampling or amniocentesis is performed early in pregnancy. Thus, prospective parents who know that they are both carriers may wish to determine if their fetus will have the disease, and may wish to terminate such a pregnancy, or to provide the physician with the opportunity to begin treatment as soon as possible, including prenatally. In the case where such screening has not been performed, and therefore the carrier status of the patient is not known, and where Canavan disease is part of the differential diagnosis, the present invention also provides a method for making the diagnosis genetically, without resort to brain biopsy.

Many versions of conventional genetic screening tests are known in the art. Several are disclosed in detail in WO 91/02796 for cystic fibrosis, in U.S. Pat. No. 5,217,865 for Tay-Sachs disease, in U.S. Pat. No. 5,227,292 for neurofibromatosis and in WO 93/06244 for Goucher disease. Thus, in accordance with the state of the art regarding assays for such genetic disorders, several types of assays are conventionally prepared using the nucleotides, polypeptides and antibodies of the present invention. For example:

Genetic screening: Biological samples containing nucleic acids can be evaluated using a variety of nucleic acid-specific techniques:

1. Direct sequencing: The DNA from an individual can be cloned, whereby both alleles are cloned. They can then be evaluated for differences in their nucleic acid sequence from normal alleles by direct sequencing of the individual's aspartoacylase gene.

2. Heteroduplex analysis: RNA transcripts can be made from a standard cloned gene, either the normal or mutant gene, and then hybridized with DNA from the individual and the resulting heteroduplex treated with RNase A and run on a denaturing gel to detect the location of any mismatches.

3. Restriction Fragment Length Polymorphism (RFLP): Restriction enzymes can be used which provide a characteristic pattern of restriction fragments, wherein a restriction site is either missing or an additional restriction site is introduced in the mutant allele. Thus, DNA from an individual and from control DNA sequences are isolated and subjected to cleavage by restriction enzymes which are known to provide restriction fragments which differentiate between normal and mutant alleles, and the restriction patterns are identified. While this assay is very simple, it is limited by the requirement that the mutation being tested for is known in advance.

4. Single Strand Conformation Polymorphism (SSCP): This is a rapid and sensitive assay for nucleotide alterations, including point mutations. See Reference 42. DNA segments 100–400 bp in length are amplified by PCR, heat denatured and electorphoresed on high resolution, non-denaturing acrylamide gels. Under these conditions, each single-stranded DNA fragment assumes a secondary structure determined in part by its nucleotide sequence. Even single base changes can significantly affect the electrophoretic mobility of the PCR product.

5. Polymerase Chain Reaction (PCR): This powerful technique can be used to test very small amounts of DNA from an individual, by amplifying DNA sequences in the region flanking the portion of the aspartoacylase gene known to be involved in a given mutation. Sequencing or other analysis of the amplified sequences is thereby simplified.

Polypeptide screening:

1. Enzymatic activity: Biological samples from the individual to be tested e.g., taken from tissues in which detectable levels of aspartoacylase are normally produced, are assayed for the presence of aspartoacylase. It is noted that brain samples are not required, even though the effects of the mutant gene are most profound in white matter. The presence or absence of an enzymatically effective aspartoacylase can then be detected according to the assay outlined in Reference 16.

2. Immunoassay: Antibodies can be produced which are specific for either or both normal or mutant aspartoacylase, according to methods outlined above. Biological samples from the individual to be tested are then assayed, e.g., taken from tissues in which detectable levels of aspartoacylase are normally produced. It is noted that brain samples are not required, even though the effects of the mutant gene are most profound in white matter. A variety of immunoassays can then be performed on the samples, using a variety of detection methods, to detect the presence or absence of the mutant gene product.

Details of protocols for performing these screening techniques are well known in the art, and are exemplified in WO 91/02796 and references cited therein, as well as U.S. Pat. No. 5,217,865, which details analogous techniques for screening for Tay-Sachs disease, which, coincidentally, is a genetic disease also present in the Ashkenazi Jewish population. Therefore, assay methods and kits are also provided which can be used to simultaneously screen for these two, as well as other, genetic diseases.

Animal Models for Canavan Disease

The creation of a mouse or other animal model for Canavan disease is crucial to a full understanding of the disease and to test possible therapies (for a review of creating animal models, see Erickson[51]). Currently, no animal model of Canavan disease exists. The evolutionary conservation of the aspartoacylase gene as demonstrated by the sequence homology with the bovine gene indicates that an orthologous gene is likely to exist in the mouse, which can be identified using human or bovine aspartoacylase sequences as probes. Thereby, generation of a specific mutation analogous to the Canavan allele can be effected to reproduce the disease phenotype, as well as other mutations, including complete inactivation of the mouse gene, in order to study the biochemistry, molecular biology and physiology of the polypeptide.

For making such animal models, the various methods disclosed in WO 91/02796 can be adapted for the aspartoacylase gene with only routine experimentation.

Thus, in addition to providing materials for screening, treatments and diagnoses, the present invention provides materials which are useful as research tools, e.g., in order to further investigate basic questions regarding the role of aspartoacylase in Canavan disease, as well as other genetic disease caused by, e.g., mutations in enzymes, in particular esterases, as well as the role of NAA hydrolysis by aspartoacylase in the disease and lead to better management of patients with CD.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, if any, are hereby incorporated by reference; the attached appendices are a part of this specification, and references cited therein are also hereby incorporated by reference.

EXAMPLES

Part I: Materials and Methods

Example 1

Materials, Reagents and Bacterial Strains

The materials and reagents used in the study were: Immobilon PVDF transfer membrane (Millipore, Bedford, Mass.); restriction enzymes (IBI, New Haven, Conn.; New England Biolabs, Beverly, Mass., Promega, Madison, Wis. and Boehringer Mannheim, Indianapolis, Ind.); Gene Amp RNA PCR kit and AmpliTaq PCR kit for amplification of DNA (Perkin-Elmer Cetus, Norwalk, Conn.); Random primed DNA labeling kit (Boehringer Mannheim, Indianapolis, Ind.); α-[$^{32}$P]-dNTP's, 3000 Ci/mMole (NEN/ Dupont, Wilmington, Del.); RNAzolB kit for preparation of cytoplasmic RNA from cultured cells (Biotecx, Houston, Tex.); Biodyne Nylon membranes for Southern and Northern blots (Pall Biosupport, East Hills, N.Y.); nitrocellulose membranes for screening libraries (Schleicher & Schuell, Keene, N.H.); and Taq Dye primer and Taq dye-terminator cycle sequencing kits for fluorescent labeled automated DNA sequencing (Applied Biosystems, Foster City, Calif.). λUni-Zap (host strain XL1 Blue) human lung cDNA library and pBS(+) and pBluescript SK⁻ phagemid vectors were from Stratagene (La Jolla, Calif.); λgt11 (host strain Y1090) human kidney and bovine lung cDNA libraries; λEMBL-3A Sp6/T7 (host strain LE 392) bovine genomic library; and poly(A)⁺ RNA were from Clontech (Palo Alto, Calif.).

Example 2

Determination of the Amino Acid Sequence of Bovine Aspartoacylase Peptides

The amino terminal sequence of bovine brain aspartoacylase could not be obtained due to the autolysis of purified protein during storage. Purified aspartoacylase was digested with cyanogen bromide[40] and peptides were fractionated on a 16×100 mm Mono Q column (FPLC system, Pharmacia LKB). Peptides were eluted with a 0–30% linear gradient of 1M sodium chloride in buffer A (25 mM Tris.Cl pH 7.2 and 0.1% sodium azide), at a flow rate of 2 ml/min. The amino acid sequences of four peptides determined at a protein sequencing facility (Yale University, New Haven, Conn.) were as follows:

CN8.1: LENSTEIQRT GLEVKPFITNPRAVKK (SEQ ID NO:13);
CN8.2: KPLIPXDPVFLTLDGKTISLGGDQTX- YPXFXNEAAYY (SEQ ID NO:14);
CN30: XKVDYPRNESGEISAIIHPKLQDQ (SEQ ID NO:15); and
CN41: XXXALDFIXNFXEXKE (SEQ ID NO:16).

Example 3

Preparation of Oligonucleotides; Reverse Transcription; PCR Amplification; DNA Probes Oligonucleotides were synthesized by phosphoramidite chemistry on a 380B DNA Synthesizer (Applied Biosystems, Foster City, Calif.). First strand cDNA was synthesized by reverse transcription of 20 ng of Poly(A)⁺ RNA or 4 μg of cytoplasmic RNA with either oligo(dt)$_n$ or a gene-specific primer under standard conditions suggested by the manufacturer. DNA amplification[41] was carried out in DNA Thermal cycler Model 9600 (Perkin-Elmer Cetus, Norwalk, Conn.). Specific DNA sequences were amplified in 100 μl volumes with 20 ng of cloned or 500 ng of genomic DNA template according to the standard conditions suggested by the manufacturer. The PCR conditions were: 1 cycle of denaturation at 94° C. for 3 min, annealing for 30 sec at temperatures ($T_m$–4° C.) that were primer-dependent and extension at 72° C. for 1 min; followed by 27 cycles of denaturation at 94° C. for 30 sec, annealing for 30 sec and extension at 72° C. for 30 sec. The last step was extension at 72° C. for 7 min. The tubes were chilled to 4° C. until further analysis. For SSCP[42] and restriction digestion analysis of mutant alleles, PCR was carried out similarly except that 1 μCi of α-[$^{32}$P] dCTP was included in the PCR reaction mixture.

Small DNA fragments of less than 200 bp were labeled with $^{32}$P by PCR amplification of the desired DNA sequences using α-[$^{32}$P] dNTP's. DNA fragments bigger than 200 bp were labeled by the random primer method[43] following the conditions suggested by the manufacturer. The specific activities of probes were 3–5×10$^8$ cpm/μg DNA.

Example 4

Isolation of cDNA Clone, and Determination and Analysis of the Nucleotide Sequence The first strand bovine cDNA was synthesized by reverse transcription (RT) of bovine kidney poly(A)⁺ RNA with oligo(dt)$_{20}$. The bovine aspartoacylase-specific coding sequences were amplified by polymerase chain reaction (PCR) using first strand cDNA as the template and CN30 peptide-based primers CD5 (AAA/GGTIGAC/TTAC/T CCIIGIAA;) (SEQ ID NO:17) and
CD8 (TGA/GTCC/TTGIAIC/TTTIGGA/G TG) (SEQ ID NO:18).

The cDNA fragment thus amplified was 69 bp long, which is the size expected from the CN30 peptide. The ORF of this fragment predicted the amino acid sequence of CN30 peptide. The 69 bp fragment was used as a probe to screen λgt11 bovine lung cDNA library. One cDNA clone, λABL2, was isolated. The insert in λABL2 had a single 839 bp long ORF. The amino acid sequence predicted by the ORF of λABL2 insert contained the CN8.1, CN8.2, CN30, and CN41 peptide sequences described earlier. However, the cDNA clone was truncated at the 5' and 3' termini. The sequences downstream of the 3' termini of λABL2 insert were cloned by RT-PCR amplification of bovine kidney poly(A)⁺ RNA using oligo(dt)$_{20}$ and the bovine aspartoacylase cDNA specific primer

CD48-1 (CCGTGTACCCAGTGTT) (SEQ ID NO:19).

A unique 770 bp fragment was amplified that overlapped with the 3' sequence of λABL2 insert. The insert from λABL2 was used to screen bovine liver genomic library cloned in λEMBL3A vector according to the standard conditions[44,45]. Limited nucleotide sequence of genomic clones identified the missing 5' coding and non-coding sequences of bovine aspartoacylase cDNA.

Bovine cDNA (data not presented), was next used for isolation of human ASP cDNA clones. Human cDNA libraries were screened and the isolated clones analyzed by the methods described earlier or according to the standard protocols[44,45]. The human lung aspartoacylase cDNA was rescued from λUni-Zap human lung cDNA clone by co-transfection with helper phage R408 into XL-1 Blue strain of E. coli according to the protocol suggested by the manufacturer. The rescued recombinant pHLASP was transfected into E. coli (XLI Blue strain). Large scale recombinant phagemid DNA were purified on cesium chloride gradients[45].

The nucleotide sequence of double stranded plasmid and amplified DNA fragments was determined by the dideoxy chain termination method[46]. M13 universal/reverse and T3/T7 primers, or dideoxy NTP's, tagged with fluorescent dyes, were used for sequencing both strands of DNA fragments on an automated 373A DNA sequencer (Applied Biosystems, Foster City, Calif.). Fluorescent DNA sequencing was carried out with DNA sequencing kits and used according to the protocols suggested by the manufacturer.

Sequences were analyzed with Lasergene software package for DNA analysis from DNAstar (Madison, Wis.).

Example 5

Analysis of RNA

Cytoplasmic RNA was prepared from cultured cell lines[47] using a RNAZOL B kit for isolation of RNA (Biotecx, Houston, Tex.). Two to three μg of poly(A)⁺ RNA and 4.5 μg of RNA markers (Promega) were denatured with formamide. The denatured RNA was fractionated on a 1% agarose gel in formaldehyde containing buffer. The RNA was transferred overnight onto a nylon membrane. The blots were baked in a vacuum oven at 80° C. for 90 min, hybridized, and then washed under stringent conditions and autoradiographed[45].

Example 6

Expression of Aspartoacylase by Human Asp cDNA Clone pHLASP

The E. coli (XLI Blue strain) transformed with recombinant pHLASP or wild type pBluescript SK⁻ phagemid were grown overnight in 15 ml of Luria broth containing glucose (0.1%) and ampicillin (50 μg/ml) in the absence or presence of 20 mM IPTG. The bacteria were harvested; treated with 500 μL of 0.05 mg/ml lysozyme in 25 mM Tris.Cl pH 8.0, 10 mM EDTA and 50 mM glucose for 10 min at ambient temperature. The treated bacteria were diluted with ice cold 1.5 ml of 50 mM Tris.Cl, pH 8.0, 0.01% β-mercaptoethanol and 0.01% sodium azide and sonicated by three 10 sec bursts in ice cold conditions. The protein concentration in the bacterial sonicates was determined[48]. Aspartoacylase assays were carried out in duplicate with 450 μg protein of bacterial sonicate under standard incubation conditions described elsewhere[16]. Controls lacking substrate or enzyme during the incubation were run simultaneously to account for background absorption in each assay. One mU of enzyme activity is defined as 1 nanomole of aspartate released/min of incubation time.

Example 7

Mutation Analysis

Cytoplasmic RNA (4 μg) from cultured fibroblast of normal controls, probands and their family members was reverse transcribed with

HKRT1 (AACCCTACTCTTAAGGAC) (SEQ ID NO:5).

Aspartoacylase specific coding sequences were amplified by PCR with

HASP9 (CTTCTGAATTGCAGAAATCA) (SEQ ID NO:20) and
HASPC7 (GTAAGACACCGTGTAAGATG) (SEQ ID NO:21)

primers. The full length coding sequence thus amplified was used as template to amplify 200 to 300 bp overlapping cDNA fragments and nucleotide sequence was determined. For a854>c point mutation analysis, a 312 bp fragment was amplified with HASP14F (F→CCGGGATGAAAATGGAGAA) (SEQ ID NO:6) and
HASPC7R (R→ACCGTGTAAGATGTAAGC) (SEQ ID NO:7)

primers. The prefix F and R in these oligos stand for M13 universal and reverse primer tags, that allowed determination of nucleotide sequence using fluorescent tagged M13 primers.

For SSCP and restriction digestion analysis, the 237 bp cDNA fragment with a854>c mutation was amplified in presence of α-[³²P] dCTP using HASPG5 (AGGATCAAGACTGGAAACC) (SEQ ID NO:8) and
HASPC7 (GTAAGACACCGTGT AAGATG) (SEQ ID NO:21)

primers. The analysis for SSCP in the 237 bp amplified cDNA fragments was carried out in 40 cm long, 5% polyacrylamide gels in 1×TBE and 5% glycerol[42]. Electrophoresis was carried out at 7.5 Watts at ambient temperature for 16–18 h, and the gel was autoradiographed. The a854>c mutation was also analyzed by restriction digestion of 237 bp cDNA fragment with Eag I or Not I. Following electrophoresis of the digest on native 5% polyacrylamide gels in 1× TAE, the gel was autoradiographed.

Part II: Results

Example 8

Isolation and Characterization of Human ASP cDNA

Human aspartoacylase specific coding sequences were amplified by RT-PCR of human kidney poly(A)⁺ RNA using oligo (dt)¹⁶ for first strand cDNA synthesis followed by PCR using bovine cDNA-based primers CD56I (GGGIATAIACIGTTICTGGIATCICCICC) (SEQ ID NO:22) and
CD59I (CCIAICGIGCIGTIAAAIGAAAIGTG) (SEQ ID NO:23) (data not shown).

A specific 676 bp cDNA fragment was amplified and found to have 90% identity to the corresponding region of the bovine ASP cDNA. The 676 bp partial human cDNA was used as probe to screen human lung λUni-Zap and human kidney λgt11 cDNA libraries. This resulted in the isolation of several overlapping clones. Three of the clones with largest insert of 1.45 kb, also had identical terminal sequences. One of these, λgt11 HK5-1 was isolated from human kidney library and two clones λUni-Zap HL 1 and two were isolated from the human lung library. The recombinant pHLASP was excised from λUni-Zap HL1 clone. The nucleotide and the predicted amino acid sequence of pHLASP is shown in FIG. 1.

The human ASP cDNA is 1,435 bp with 158 bp 5' and 316 bp 3' untranslated sequence. The isolated cDNA has 18 bases long poly(A) tail. A polyadenylation signal "aataaa" is found 48 bases upstream from the poly(A) addition site. Another consensus polyadenylation signal sequence "tataaa" is present 23 bases upstream from the poly(A) addition site.

The position of "tataaa" is within the suggested location of 10–30 bases upstream from the poly(A) addition site[17,18]. Human and bovine ASP encoded transcripts and proteins do not match any known sequences in the databases.

The open reading frame (ORF) in human ASP cDNA predicted 313 amino acid long protein that is 92% identical to bovine ASP encoded protein (see FIG. 2). The molecular weight is estimated to be 36 kD. The predicted protein sequence has potentially one "N" glycosylation and 7 phosphorylation sites. The amino acid sequence motifs GGTH-GNE (SEQ ID NO:10), DCTV (SEQ ID NO:24) and VNEAAYY (SEQ ID NO:11) identified in both proteins, are similar to the consensus sequences GXXHG/AXE/D (SEQ ID NO:25), DXXF/V (SEQ ID NO:26) and VXEXXXY (SEQ ID NO:27) involved in the catalysis by esterases[19].

Example 9

Tissue Distribution and Size of Aspartoacylase Transcripts

Human poly(A)+ RNA, 2 μg each from various tissues, were analyzed by Northern blot analysis (FIG. 3). The poly(A)+ RNA from human liver gave a single band of 1.44 kb, whereas that from other human tissues tested gave two bands of 1.44 and 5.4 kb. The 1.44 kb faster moving band was similar in size to the 1.435 kbp human ASP cDNA. It appears that human brain expresses a relatively higher proportion of the larger transcript, as compared to relative amounts of the two transcripts in each of the tissues analyzed. The intensity of signals for both bands was highest in human skeletal muscles, followed by kidney and brain.

Example 10

Expression of Aspartoacylase Activity in Human Lung cDNA

Figure 4:
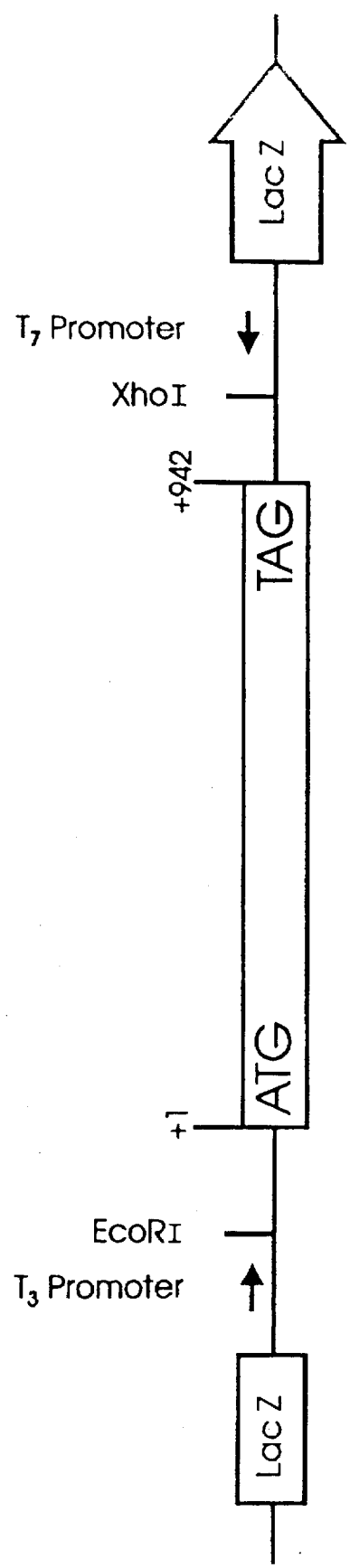
FIG. 4 depicts a schematic representation of pHLASP cloned in pBluescript SK$^-$. The human ASP cDNA was cloned between Eco RI and Xho I sites in 5'→3' direction and the transcription was driven by LACZ promoter. The initiator "atg" and terminator "tag" codons are shown. Other vector regions are not represented in the schematics. The figure is not drawn to scale.

The orientation of human ASP cDNA (pHLASP) cloned in pBluescript SK⁻ phagemid vector is shown in FIG. 4. The cDNA was cloned as an Eco RI and Xho I insert in pBluescript SK⁻ phagemid in 5'→3' direction. The transcription of human ASP cDNA, driven by LACZ promoter, was studied in the absence and presence of the LACZ inducer isopropylthio-β-D-galactoside (IPTG) in $E.$ $coli$ (XL1 Blue strain). The mean aspartoacylase activity expressed by the pHLASP construct was 0.111, (range 0.044–0.175), mU/mg protein in the absence of IPTG. The activity increased 4-fold to 0.436 (range 0.223–0.622) mU/mg protein when cultures were grown in the presence of 20 mM IPTG. The level of activity expressed by pHLASP was more than 2 orders of magnitude higher than the mean residual activity of 0.019 (range 0.000–0.043) mU/mg protein observed with wild type pBluescript SK⁻ in the presence of IPTG. These results demonstrate that human ASP cDNA codes for aspartoacylase.

Example 11

Determination of a Missense Mutation in Human ASP cDNA from Patients with CD

Figure 5A:
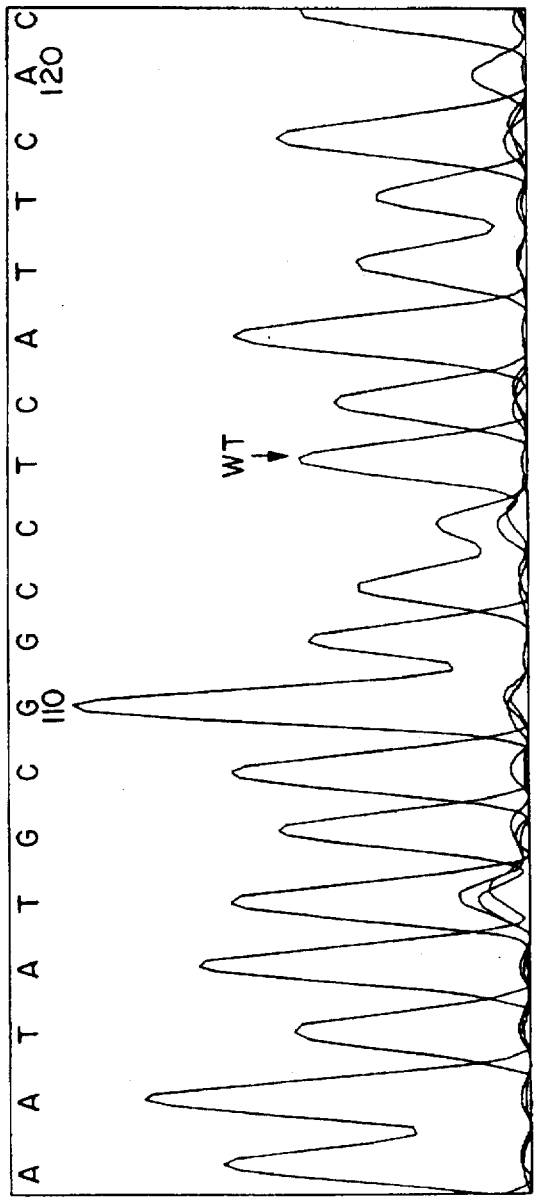
FIG. 5 depicts the nucleotide sequence of 312 bp cDNA fragment in the region of a854>c mutation from normal controls (WT, Panel A) and a patient with CD (MUT, Panel B). Reverse transcription of cytoplasmic RNA with HKRT1 (AACCCTACTCTTAAGGAC) (SEQ ID NO:5) primer was followed by amplification with HASP14F (F→CCGGGATGAAAATGGAGAA) (SEQ ID NO:6) and HASPC7R (R→ACCGTGTAAGATGTAAGC) (SEQ ID NO:7) primers. The prefix F and R in these oligos stand for M13 universal and reverse primer tags. Fluorescent di-deoxy sequencing of both strands were carried out with M13 universal and reverse primers. The patient with CD (MUT) was homozygous for a854>c point mutation and the base involved is shown by a down arrow (↓). The mutation would result in E285>A missense mutation at the amino acid level.
Figure 5B:
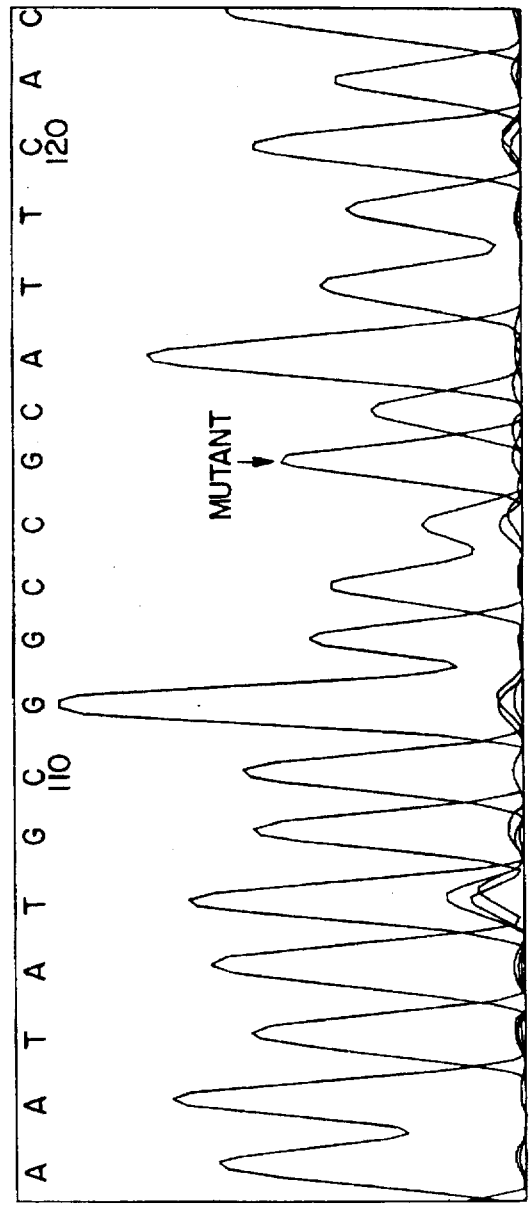

The ASP encoded transcripts were analyzed from family members of 17 unrelated pedigrees of Ashkenazi Jewish background. Representative nucleotide sequence data for mutation analysis is shown in FIG. 5. A base change a854>c was identified in patients with CD. Both parents of a854>c homozygous patients were carriers for this mutation. Normal controls and non-carrier sibling of patients with CD did not have the a854>c base change in their ASP encoded transcript. The a854>c base change would alter the E285 codon in aspartoacylase and result in E285>A missense mutation.

Figure 6A:
FIG. 6 depicts the single strand conformation polymorphism (Panel A) and Eag I restriction endonuclease digestion (Panel B) of 237 bp cDNA fragment amplified by RT-PCR of cytoplasmic RNA from normal controls, and Canavan probands and their family members. After initial reverse transcription of cytoplasmic RNA with HKRT1 (AACCCTACTCTTAAGGAC) (SEQ ID NO:5) primer the 237 bp cDNA fragment was amplified using HASPG5 (AGGATCAAGACTGGAAACC) (SEQ ID NO:8) and HASPC7 (GTAAGACACCGTGTAAGA TG) (SEQ ID NO:9) primers. Representative SSCP and restriction digestion analysis of a854>c point-mutation in 3 families is shown and the pedigrees are drawn at the top. One of the normal controls (Lane 4) and the non-carrier sibling of a patient with CD (Lane 1) are also shown.
Figure 6B:
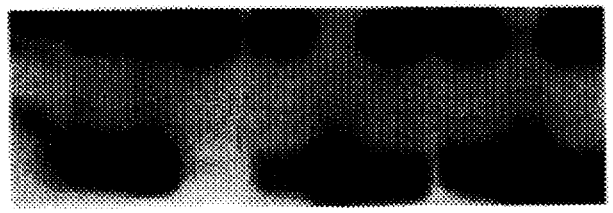

The a854>c base change creates recognition sequences for Eag I and Not I restriction endonuclease in the mutant allele. The mutation was analyzed in an amplified 237 bp cDNA fragment for single strand conformation polymorphism (SSCP) and by digestion with restriction endonuclease Eag I. Typical mutation analysis profile from three representative pedigrees are shown in FIG. 6. Individuals homozygous, heterozygous or non-carriers for a854>c mutation could be differentiated by SSCP analysis (see FIG. 6, Panel A). Following digestion of the 237 bp fragment with Eag I (FIG. 6, Panel B), probands homozygous for the a854>c point mutation produced two restriction fragments of 125 and 112 bp; obligate carriers and heterozygotes had an undigested 237 bp fragment and two restriction fragments of 125 and 112 bp, while normal controls and non-carriers for a854>c point mutation had only the 237 bp fragment. The a854>c base mutation was observed in 85% (29 out of 34) of the Canavan alleles and is inherited as a Mendelian recessive trait. Of the 17 probands, 12 were found to be homozygous and 5 were heterozygous for this mutation. In the 5 compound heterozygote patients with CD, the mutation on a second Canavan allele was further investigated. The a854>c base change was not observed in any of 84 normal individuals analyzed so far.

In addition, the following primers can be used as disclosed to detect the presence or absence of the missense mutation:

| Primer | Sequence | Direction | Use |
| --- | --- | --- | --- |
| 6A | 5'GTCTAGAGTCTGACATAAATT 3' | Sense | PCR/digestion |
| RT1 | 5'AACCCTACTCTTAAGGAGC 3' | Antisense | PCR/digestion |
| C7 | 5'TTTGTAAGACACCGTGTAAGA 3' | Antisense | PCR/digestion |
| C7R | 5'CAGGAAACAGCTATGACCCACCG TGTAAGATGTAAGC 3' | Antisense | Sequencing/digestion |
| RT1R | 5'CAGGAAACAGCTATGACCCAACCC TACTCTTAAGGAGC 3' | Antisense | Sequencing/digestion |
| 6AF | 5'TGTAAAACGACGGCCAGTGTCTAG AGTCTGACATAAATT 3' | Sense | PCR/digestion |

-continued

| PCR Primers | Product size | EagI/NotI digestion | |
|---|---|---|---|
| 854A > C (Glu285 > Ala) mutation | | | |
| 6A/RT1 | 347 bp | Wild type: | No site |
| | | Mutant: | 184 and 163 bp |
| 6A/C7 | 312 bp | Wild type: | No site |
| | | Mutant: | 184 and 128 bp |
| G5/C22 | 194 bp | Wild type: | No site |
| | | Mutant: | 112 and 82 bp |

Example 12

Additional Mutations Identified

In addition to the major a854>c mutation present in about 85% of the Canavan patients and carriers of Ashkenaszi Jewish descent, several other mutations were identified using similar analyses.

In each case, genomic DNA was prepared from cultured skin fibroblast cell lines or from lymphocytes, according to methods described in Kaul et al., 1994. In certain instances, "Guthrie" blood spots were used for mutation analysis. Genomic DNA (500 ng) or "Guthrie" blood spots were used for PCR amplification of ASP-specific coding and exon/intron boundary sequences, as described in Kaul et al., 1993. The muations were characterized by (a) determination of the nucleotide sequence by using dideoxy chain termination chemistry (Sanger et al., 1997), (b) analyses of SSCP (Orita et al., 1989), and (c) restriction-endonuclease digestion, as described in Kaul et al., 1993. Mutations that did not result in a gain or loss of a restriction-endonuclease site were analyzed by PCR-directed site-specifi mutagenesis (PSDM). A primer with mismatch at a unique position in its sequence was synthesized. After PCR amplification, the mismatch in the PCR primer created a unique recognition sequence for a restriction endonuclease, either in mutant or wild-type (WT) alleles. The mutant and WT alleles could thus be differentiated by restriction digestion of the PCR-amplified products.

t47>c (I16>T)

This mutation results in a codon change which causes a translation error in exon 1, wherein an Ile residue is replaced by a Thr residue.

c342>a (D114>E)

This mutation results in a codon change which causes a translation error in exon 2, wherein an Asp residue is replaced by a Glu residue.

g368>a (G23>E)

This mutation results in a codon change which causes a translation error in exon 2, wherein an Gly residue is replaced by a Glu residue.

433 -2(A>G) IVS2

This mutation, which occurs in the splice-acceptor site in intron 2, leads to skipping of exon 3, accompanied by a frameshift, and thus produces abberant aspartoacylase. It accounts for 1.1% of the mutations of Jewish probands.

t454>c (C152>Y)

This mutation results in a codon change which causes a translation error in exon 3, wherein a Cys residue is replaced by a Tyr residue.

g455>a (C152>Y)

This mutation also results in a codon change which causes a translation error in exon 3, wherein a Cys residue is replaced by a Tyr residue.

c502>t (R168>C)

This mutation results in a codon change which causes a translation error in exon 3, wherein an Arg residue is replaced by a Cys residue.

c541>a (P181>T)

This mutation results in a codon change which causes a translation error in exon 4, wherein a Pro residue is replaced by a Thr residue.

c693>a (Y231>ter)

The c693>a mutation results in the codon change TAC>TAA, which results in a translation error in exon 5 of Y231>X; thus, this mutation causes premature termination of the polypeptide chain at the location where a tyrosine residue is supposed to be. This is a "nonsense" mutation. This mutation constitutes 14.8% of the mutations in the probands of Jewish descent.

a854>c (E285>A)

This mutation results in a codon change which causes a translation error in exon 6, wherein a Glu residue is replaced by an Ala residue.

876 del agaa (4 bp deletion)

This mutation results in a 4 bp deletion in exon 6 which results in a frameshift mutation and thus changes the amino acid sequence of aspartoacylase beyond this point. The deletion also results in premature termination of the protein product.

c914>a (A305>E)

Another allele which has been identified is a c914>a change, which results in the codon change GCA>GAA, which in turn results in the missense mutation A305>E in exon 6, substituting a Glu residue for an Ala residue. This mutation is the major mutation present in 20 non-Jewish probands of European descent studied, and consitituted 60% of the 40 mutant chromosomes.

t928>g (C310>G)

This mutation results in a codon change which causes a translation error in exon 6, wherein a Cys residue is replaced by a Gly residue.

Example 13

Additional Amplification, Sequencing and Mutation Analysis of the Aspartoacylase Gene Using Various Primer Sequences A wide array of primer sequences have been generated to simplify and improve the sequence and mutation analysis of the aspartoacylase gene. In particular, these primers have been developed to improve the detection of mutations by RFLP. These include analytical methods for each of the mutations discussed above. These primers and mutations are presented in the context of the exon in which they appear, since one primer may be useful in detecting more than one mutation.

TABLE 2

Mutation Analysis by Exons

Exon 1 coding and its boundary sequence amplification, sequencing and mutation analysis

| Primer | Sequence | Direction | Use |
| --- | --- | --- | --- |
| 9 (nt 119–139 of SEQ ID NO:1) | 5'CTTCTGAATTGCAGAAATCAG 3' | Sense | PCR |
| 1B (SEQ ID NO:28) | 5'CCACTTTCACACAACATCC 3' | Antisense | PCR |
| 9f (SEQ ID NO:29) | 5'TGTAAAACGACGGCCAGTTCTGA ATTGCAGAAATCAGATA 3' | Sense | Sequencing |
| 1BR (SEQ ID NO:30) | 5'CAGGAAACAGCTATGACCCCACTT TCACACAACATCC 3' | Antisense | Sequencing |

47T > C (Ile16 > Thr) mutation

| | | | |
| --- | --- | --- | --- |
| PCR primers: | I16TKpnA/C16 | | |
| Product size: | 154 bp | | |
| KpnI digestion: | Wild type allele: No site | | |
| | Mutant allele: 129 and 25 bp fragments | | |
| I16TKpnA (SEQ ID NO:31) | 5'AAGAACATATACAAAAGGTTG*TA3' | Sense | PCR/KpnI digestion |
| C16 (SEQ ID NO:32) | 5'TCTTCACTGCTCTGGGGTT 3' | Antisense | PCR/KpnI digestion |

*: C > G mismatch for PCR directed site specific mutagenesis (PDSM).

Exon 2 coding and boundary sequence amplification, sequencing and mutation analysis

| Primer | Sequence | Direction | Use |
| --- | --- | --- | --- |
| 2A (SEQ ID NO:33) | 5'TATTATCTCAGGCACAGATG 3' | Sense | PCR |
| 2B (SEQ ID NO:34) | 5'CAAGTCCTTTGCTGACTTAT 3' | Antisense | PCR |
| 2AF (SEQ ID NO:35) | 5'TGTAAAAGGACGGCCAGTATCTC AGGCACAGATGTTG 3' | Sense | Sequencing |
| 2BR (SEQ ID NO:36) | 5'CAGGAAACAGCTATGACCGTCCT TTGCTGACTTATAAA 3' | Antisense | Sequencing |

342C > A (Asp114 > Glu) mutation

| | | | |
| --- | --- | --- | --- |
| CR primers: | 2B/D114EBst | | |
| Product size: | 156 bp | | |
| BstB1 digestion: | Wild type: No site | | |
| | Mutant: 136 and 20 bp | | |
| D114EBst (SEQ ID NO:37) | 5'GATTCCTATGACATTATTTTC*GA 3' | Sense | PCR/digestion |

*: T > C mismatch for PCR directed site specific mutagenesis

368G > A (Gly123 > Glu) mutation

| | | | |
| --- | --- | --- | --- |
| PCR primers: | 2B/G123ETaq | | |
| Product size: | 129 bp | | |
| TaqI digestion: | Wild type: No site | | |
| | Mutant: 109 and 20 bp | | |
| G123ETaq (SEQ ID NO:38) | 5'CACAACACCACCTCTAACATC*G 3' | Sense | PCR/TaqI digestion |

*: G > C mismatch for PCR directed site specific mutagenesis

Exon 3 coding and its boundary sequence amplification, sequencing and mutation analysis

| Primer | Sequence | Direction | Use |
| --- | --- | --- | --- |
| 3A (SEQ ID NO:39) | 5'AACATACGGTTTTTACCTAAG 3' | Sense | PCR |
| 3B (SEQ ID NO:40) | 5'TCTCTGAGTTTCAGCTAGG 3' | Antisense | PCR |
| 3AF (SEQ ID NO:41) | 5'TGTAAAACGACGGCCAGTCATAC GGTTTTTACCTAAGAA 3' | Sense | Sequencing |
| 3BR (SEQ ID NO:42) | 5'CAGGAAACAGCTATGACCCTGCG TTTCAGCTAGGACA 3' | Antisense | Sequencing |

454T > C (Cys152 >Tyr) mutation

| | | | |
| --- | --- | --- | --- |
| PCR primers: | 3A/C152RHPA2 | | |
| Product size: | 89 bp | | |
| HpaII digestion: | Wild type: | No site | |
| | Mutant: | 68 and 21 bp | |
| C152RHpa2 (SEQ ID NO:43) | 5'GCTCAATCAGATAAACGTAC*C 3' | Antisense | PCR/digestion |

*: G > C mismatch for PCR directed site specific mutagenesis

455G > A (Cys152 > Tyr) mutation

| | | | |
| --- | --- | --- | --- |
| PCR primers: | R168CTaq/C152YRsaI | | |
| Product size: | 87 bp | | |
| RsaI digestion: | Wild type: No site | | |
| | Mutant: 67 and 20 bp | | |
| C152YRsaI (SEQ ID NO:44) | 5'TTCTCTGGCTCCACTACCG*T 3' | Sense | PCR/digestion |

*: G > C mismatch for PCR directed site specific mutagenesis

502C > T (Arg168 > Cys) mutation

| | |
| --- | --- |
| PCR primers: | R168CTaq/C152YRsaI |
| Product size: | 87 bp |

TABLE 2-continued

Mutation Analysis by Exons

TaqI digestion:     Wild type:     69 and 18 bp
                 Mutant:     No site R168CTaqI (SEQ ID NO:45)     5'AGGATACTTGGCTATGGAT*C 3'     Antisense     PCR/digestion

*: A > T mismatch for PCR directed site specific mutagenesis

433 -2(A > G) IVS2 mutation

PCR primers:     3B/IVS2AHpa2
Product size:     179 bp
HpaII digestion: Wild type:     No site
                     Mutant:     156 and 23 bp IVS2AHpa2 (SEQ ID NO:46)     5'GAAAGACGTTTTTGATTTTTTC*C 3'     Sense     PCR/digestion

*: T > C mismatch for PCR directed site specific mutagenesis

Exon 4 coding and its boundary sequence amplification, sequencing and mutation analysis

| Primer | Sequence | Direction | Use |
|---|---|---|---|
| 4A (SEQ ID NO:47) | 5'CATACTTATATAAATGTGACTAT 3' | Sense | PCR/digestion |
| 4B (SEQ ID NO:48) | 5'TCTGACCCAGGTTCCAATT 3' | Antisense | PCR/digestion |
| 4AF (SEQ ID NO:49) | 5'TGTAAAACGACGGCCAGTTACTTA TATAAATGTGACTATCT 3' | Sense | Sequencing |
| 4BR (SEQ ID NO:50) | 5'CAGGAAACAGCTATGACCGACCCAG GTTCCAATTGTT 3' | Antisense | Sequencing |

541C > A (Pro181 > Thr) mutation

PCR primers:     4A/4B
Product size:     221 bp
RsaI digestion:     Wild type:     188 and 33 bp
                 Mutant:     168, 33 and 20 bp

Exon 5 coding and its boundary sequence amplification, sequencing and mutation analysis

| Primer | Sequence | Direction | Use |
|---|---|---|---|
| 5A (SEQ ID NO:51) | 5'CCAGAGATGTTTTTAGTTGC 3' | Sense | PCR/MseI digestion |
| 5B (SEQ ID NO:52) | 5'TGCTGTATGAGCTATAAACTT 3' | Antisense | PCR/MseI digestion |
| 5AF (SEQ ID NO:53) | 5'TGTAAAACGACGGCCAGTCCAGAG ATGTTTTTAGTTG 3' | Sense | Sequencing/MseI digestion |
| 5BR (SEQ ID NO:54) | 5'CAGGAAACAGCTATGACCTGCTGT ATGAGCTATAAACTT 3' | Antisense | Sequencing/MseI digestion |

693C > A (Tyr231 > Ter) mutation

PCR primers:     5A/5B
Product size:     235 bp
MseI digestion:     Wild type:     177 and 58 bp
                 Mutant:     104, 73 and 58 bp

Exon 6 coding and its boundary sequence amplification, sequencing and mutation analysis

| Primer | Sequence | Direction | Use |
|---|---|---|---|
| 6A (SEQ ID NO:55) | 5'GTCTAGAGTCTGACATAAATT 3' | Sense | PCR/digestion |
| RT1 (SEQ ID NO:56) | 5'AACCCTACTCTTAAGGAGC 3' | Antisense | PCR/digestion |
| C7 (SEQ ID NO:57) | 5'TTTGTAAGACACCGTGTAAGA 3' | Antisense | PCR/digestion |
| C7R (SEQ ID NO:58) | 5'CAGGAAACAGCTATGACCCACCG TGTAAGATGTAAGC 3' | Antisense | Sequencing/digestion |
| RT1R (SEQ ID NO:59) | 5'CAGGAAACAGCTATGACCCAACCC TACTCTTAAGGAGC 3' | Antisense | Sequencing/digestion |
| 6AF (SEQ ID NO:60) | 5'TGTAAAACGACGGCCAGTGTCTAG AGTCTGACATAAATT 3' | Sense | PCR/digestion |

854A > C (Glu285 > Ala) mutation

| PCR Primers | Product size | EaqI/NotI digestion | |
|---|---|---|---|
| 6A/RT1 | 347 bp | Wild type: | No site |
| | | Mutant: | 184 and 163 bp |
| 6A/C7 | 312 bp | Wild type: | No site |
| | | Mutant: | 184 and 128 bp |
| G5/C22 | 194 bp | Wild type: | No site |
| | | Mutant: | 112 and 82 bp |

876 del agaa (4 bp deletion) mutation

PCR amplification of exon 6 sequences followed by SSCP analysis and sequencing

914C > A (Ala305 > Glu) mutation: Method 1

TABLE 2-continued

Mutation Analysis by Exons

| | | |
|---|---|---|
| PCR primers: | C22/G5 | |
| Product size: | 194 bp | |
| NsiI digestion: | Wild type: | 173 and 21 bp |
| | Mutant: | No site |
| C22 (SEQ ID NO:61) | 5'TAAACAGCAGCGAATACTTTA*T3' | Antisense PCR/digestion |

*: T > A mismatch for PCR directed site specific mutagenesis

914C > A (Ala305 > Glu) mutation: Method 2

| | | |
|---|---|---|
| PCR primers: | 914BsmI/RT1R | |
| Product size: | 153 | |
| BsmI digestion: | Wild type: | 120 and 33 bp |
| | Mutant: | No site |
| PCR primers: | 914BsmI/RT1 | |
| Product size: | 135 | |
| BsmI digestion: | Wild type: | 102 and 33 bp |
| | Mutant: | No site |
| 914BsmI (SEQ ID NO:62) | 5'TTTTGCAAAGACAACTAAACTAACG CTG*AATG3' | Sense PCR/digestion |

*: C > G mismatch for PCR directed site specific mutagenesis.

928T > G (Cys310 > Gly) mutation

| PCR Primers | Product size | BstU I digestion | |
|---|---|---|---|
| 6A/RT1 | 347 bp | Wild type: | No site |
| | | Mutant: | 256 and 91 bp |
| 6A/C7 | 312 bp | Wild type: | No site |
| | | Mutant: | 256 and 56 bp |
| G5/C22 | 194 bp | Wild type: | No site |
| | | Mutant: | 183 and 11 bp |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

GENERAL REFERENCES

1. Globus, J. H. & Strauss, I. Progressive degenerative subcortical encephalopathy (Schilder's disease). Arch. Neurol. Psychiat. 20:1190–1228 (1928).

2. Canavan, M. M. Schilder's encephalitis periaxialis diffusa. Arch. Neurol. Psychiat. 25:299–308 (1931).

3. van Bogaert, L. & Bertrand, I. Sur une idiotie familiale avec degerescence songlieuse de neuraxe (note preliminaire). Acta. Neurol. Belg. 49:572–587 (1949).

4. Adachi, M., Torii, J., Schneck, L. & Volk, B. W. Electron microscopic and enzyme histochemical studies of the cerebellum in spongy degeneration (van Bogaert and Bertrand type). Acta. Neuropath. 20:22–31 (1972).

5. Adornato, B. T., O'Brien, J. S., Lampert, P. W., Roe, T. F. & Neustein, H. B. Cerebral spongy degeneration of infancy: a biochemical and ultrastructural study of affected twins. Neurology 22:202–210 (1972).

6. Matalon, R., Michals, K., Sebasta, D., Deanching, M., Gashkoff, P. & Casanova, J. Aspartoacylase deficiency and N-acetylaspartic aciduria in patients with Canavan Disease. Am. J. Med. Genet. 29:463–471 (1988).

7. Birnbaum, S. M. Amino acid acylases I and II from hog kidney. Methods Enzymol. 2:115–119 (1955).

8. Birnbaum, S. M., Levinton, L., Kingsley, R. B. & Greenstein, J. P. Specificity of amino acid acylases. J. Biol. Chem. 194:455–462 (1952).

9. Matalon, R., Kaul R., Casanova, J., Michals, K. Johnson A., Rapin, I., Gashkoff, P. & Deanching, M. Aspartoacylase deficiency: the enzyme defect in Canavan Disease. J. Inher. Met. Dis. 12:329–331 (1989).

10. Matalon, R., Kaul, R. & Michals, K. Canavan disease: biochemical and molecular studies. J. Inher. Metab. Dis. (in press).

11. Grodd, W., Krägeloh-Mann, I., Petersen, D., Trefz, F. K. & Harzer, K. In vivo asessment of N-acetylaspartate in brain in spongy degeneration (Canavan disease) by proton spectroscopy. Lancet 336:437–438 (1990).

12. Matalon, R., Kaul, R. & Michals, K. In The Molecular Biology and Genetic Basis of Neurological Disease, (eds Rosenberg, R. N. et al.) 541–546 (Butterworth-Heineman, Boston, 1993).

13. Ozand, P. T., Gascon, G. & Dhalla, M. Aspartoacylase deficiency and canavan disease in Saudi Arabia. Am. J. Med. Genet. 35:266–268 (1990).

14. Michelakakis, H., Giouroukos, S., Divry, P., Katsarou, E., Rolland, M. O. & Skardoutsow A. Canavan Disease: findings in four new cases. J. Inher. Matab. Dis. 14:267–268 (1991).

15. Matalon, R., Michals, K., Gashkoff, P. & Kaul, R. Prenatal diagnosis of Canavan disease. J. Inher. Metab. Dis. 15:392–394 (1992).

16. Kaul, R., Casanova, J., Johnson, A., Tang, P. & Matalon, R. Purification, characterization and localization of aspartoacylase from bovine brain. J. Neurochem. 56:129–135 (1991).

17. Proudfoot N. J. & Brownlee, G. G. 3' Non-coding region sequences in eukaryotic messenger RNA. Nature 263:211–214 (1976).

18. Birnstiel, M. L., Busslinger, M. & Strub, K. Transcription termination and 3' processing: the end is in site!. Cell 41:349–359 (1985).

19. Cygler, M. et al. Relationship between sequence conservation and three-dimentional structure in a large family of esterases, lipases, and related proteins. *Protein Science* 2:366–382 (1993).

20. Lemeur, M. A., Galliot, B. & Gerlinger, P. Termination of the ovalbumin gene transcription. *EMBO J.* 3:2779–2786 (1984).

21. Miller, Y. R., Drabkin, H., Jones, C. & Fisher, J. H. Human aminoacylase-1: cloning, regional assignment to distal chromosome 3p21.1, and identification of a cross-hybridizing sequence on chromosome 18. *Genomics* 8:149–154 (1990).

22. Goldstein, F. B. Biosynthesis of N-acetyl-L-aspartic acid. *J. Biol. Chem.* 234:2702–2706 (1959).

23. Goldstein, F. B. The enzymatic synthesis of N-acetyl-L-aspartic acid by subcellular preparations of rat brain. *J. Biol. Chem.* 244:4257–4260 (1969).

24. Moffett, J. R., Namboodiri, M. A., Cangro, C. B. & Neale, J. H. Immunohistochemical localization of N-acetylaspartate in rat brain. *NeuroReport* 2:131–134 (1991).

25. Urenjak, J., Williams, S. R., Gadian, D. G. & Noble, M. Specific expression of N-acetylaspartate in neurons, oligodendrocyte-type-2 astrocyte progenitors, and immature oligodendrocytes in vitro. *J. Neurochem.* 59:55–61 (1992).

26. Moffett, J. R., Namboodiri, M. A. & Neale, J. H. Enhanced carbodiimide fixation for immunohistochemistry: application to the comparative distributions of N-acetylaspartylglutamate and N-acetylaspartate immunoreactivities in rat brain. *J. Histochem. Cytochem.* 31:559–570 (1993).

27. Tallan, H. H., Moore, S. & Stein, W. H. N-Acetyl-L-aspartic acid in brain. *J. Biol. Chem.* 219:257–264 (1956).

28. Jacobson, K. B. Studies on the role of N-acetylaspartic acid on mammalian brain. *J. Gen. Physiol.* 43:323–333 (1957).

29. McIntosh, J. M. & Cooper, J. R. Studies on the function of N-acetylaspartic acid in the brain. *J. Neurochem.* 12:825–835 (1965).

30. Shigematsu, H. et al. Purification and characterization of the heat stable factors essential for conversion of lignoceric acid to cerebronic acid and glutamic acid: identification of N-acetyl-L-aspartic acid. *J. Neurochem.* 40:814–820 (1983).

31. Cangro, C. B., Namboodiri, M. A. A., Sklae, L. A., Corigliano-Murphy, A. & Neale, J. H. Immunocytochemistry and biosynthesis of N-acetylaspartylglutamate in spinal sensory ganglia. *J. Neurochem.* 49:1579–1588 (1987).

32. Ory-Lavollee, L., Blakely R. D. & Coyle, J. T. Neurochemical and immunocytochemical studies on the distribution of N-acetylaspartylglutamate and N-acetylaspartate in rat spinal cord and some peripheral nervous tissues. *J. Neurochem.* 48:895–899 (1987).

33. Birken, D. L. & Oldendorf, W. H. N-Acetyl-L-aspartic acid: A literature review of a compound prominent in $^1$H-NMR spectroscopic studies on brain. *Neurosci. Behavioral Rev.* 13:23–31 (1989).

34. Grood, W., Krägeloh-Mann, I., Klose, U. & Sauter, R. Metabolic and destructive brain disorders in children: Finding with localized proton MR spectroscopy. *Radiology* 181:173–181 (1991).

35. Dunlop, D. S, McHale, D. M. & Lajtha, A. Decreased brain N-acetylaspartate in Huntington's disease. *Brain Research* 580:44–48 (1992).

36. Meyerhoff, D. J. et al. Reduced brain N-acetylaspartate suggests neuronal loss in cognitively impaired human immunodeficiency virus-seropositive individuals: In vivo $^1$H magnetic resonance spectroscopic imaging. *Neurology* 43:509–515 (1993).

37. Gideon, P. et al. Early time course of N-acetylspartate, creatine and phosphocreatine, and compounds containing choline in the brain after acute stroke-a proton magnetic resonance spectroscopy study. *Stroke* 23:1566–1572 (1992).

38. Marcucci, F., Colombo, L., De Ponte, G. & Mussini, E. Decrease in N-acetyl-L-aspartic acid in brain of myodystrophic mice. *J. Neurochem.* 43:1484–1486 (1984).

39. Bell, J. D. et al. In vivo detection of metabolic changes in a mouse model of scrapie using nuclear magnetic resonance spectroscopy. *J. Gen. Virology* 72:2419–2423 (1991)

40. Kaul, R., Murthy S. N. P., Reddy A. G., Steck, T. L. & Kohler, H. Amino acid sequence of the N-terminal 201 residues of human erythrocyte membrane band 3. *J. Biol. Chem.* 258:7981–7990 (1983).

41. Saiki, R. K. et al. Enzymatic amplification of β-globin genomic sequences and restriction site analysis for diagnosis of sickle cell anemia. *Science* 230:1350–1354 (1985).

42. Orita, M., Suzuki, Y., Sekiya, T. & Hayashi, K. Rapid and sensitive detection of point mutations and DNA polymorphisms using the polymerase chain reaction. *Genomics* 5:874–879 (1989).

43. Feinberg, A. P. & Vogelstein, B. Technique for radio labelling DNA restriction endonuclease fragments to high specific activity. *Anal. Biochem.* 137:266–267 (1984).

44. Kaul, R., Hidebrand, B. Roberts, S. & Jagadeeswaran, P. Isolation and characeterization of human blood coagulation factor X cDNA. *Gene* 41:311–314 (1986).

45. Sambrook, J., Fritsch, E. F. & Maniatis, T. *Molecular Cloning: A laboratory manual* 2nd ed. (Cold Spring Harbour Laboratory, New York, 1989).

46. Sanger, F. S., Nicklen, I. & Coulson, A. R. DNA sequencing with chain terminating inhibitors. *Proc. Natl. Acad. Sci. U.S.A.* 74:5463–5467 (1977).

47. Chomczynski, P. & Sacchi, N. Single step method of RNA isolation by acid guanidinium thiocyanate-phenol-chloroform extraction. *Anal. Biochem.* 162:156 (1987).

48. Lowry, O. H., Rosenbroug, N. J., Farr, A. L. & Randall, R. J. Protein measurement with the folin phenol reagent. *J. Biol. Chem.* 193:265–275 (1951).

49. Kohler and Milstein, *Nature* 256:495 (1975).

50. *Human Gene Therapy*, 1(#1)–4(#4) et seq., (1990–1993), W. French Anderson, M.D., ed., Mary Ann Leibert, Inc., New York City, N.Y.

51. Erickson, *Am. J. Hum. Genet.* 43:582 (1988).

52. Kaul et al., *Genomics* 21:364–370 (1994).

53. Kaul et al., *Am. J. Hum. Genet.* 55:(in press) (1994).

EXEMPLARY REFERENCES DISCLOSING METHODS APPLICABLE TO THE PRESENT INVENTION

1. Cited in WO 92/10564
   Selection and construction of recombinant viral vectors and production of high titers thereof
   1a. Keller et al., *Nature*, 318:149–154 (1985)
   1b. U.S. Pat. No. 4,861,719
   1c. Miller et al., *Cold Spring Harbor Symp. on Quantitative Biology*, Vol. LI, Cold Spring Harbor Laboratory, pp. 1013–1019 (1986)
   1d. Miller et al., *Somat. Cell. Mol. Genet.*, 12:175–183 (1986)

1e. *Proc. Nat'l Acad. Sci. USA*, 80:4709–4713
Preparation of producer cells
  1f. Mann et al., *Cell*, 33:153–159 (1983)
  1g. Miller et al., *Mol. Cell. Biol.*, 6:2895–2902 (1986)
  1h. U.S. Pat. No. 4,861,719
  1i. Hock et al., *Blood*, 74:876–881 (1989)
Selecting target cells and transducing them with recombinant viral vectors
  1j. Palmer et al., *Proc. Nat'l Acad. Sci.*, 84:1055 (1987)
  1k. St. Louis et al., *Proc. Nat'l Acad. Sci.*, 85:3150–54 (1988)
  1l. International Application No. WO 90/01870
  1m. U.S. Pat. No. 4,868,116
2. Cited in U.S. Pat. No. 5,227,292
  Procaryotic and eucaryotic host cells
    2a. Maniatis et al., *Molecular Cloning: A Laboratory Manual*, Cold Spring Harbor Laboratory, Cold Spring Harbor, N.Y. (1982)
    2b. Sambrook et al., *Molecular Cloning: A Laboratory Manual 2nd Ed.*, Cold Spring Harbor Laboratory, Cold Spring Harbor, N.Y. (1989)
    2c. *Meth. Enzymol.*, Vol. 68, 100, 101, 152–155, Academic Press, Orlando (1979, 1983, 1987)
    2d. Pouwels et al., *Cloning Vectors: A Laboratory Manual*, Elsevier, Amsterdam (1987)
    2e. U.S. Pat. No. 4,711,845
    2f. Cruz and Patterson, *Tissue Culture*, Academic Press, Orlando (1973)
    2g. *Meth. Enzymol.*, Vol. 58, Academic Press, Orlando (1979)
    2h. Freshney, *Culture of Animals Cells: A Manual of Basic Technique*, 2nd Ed., Alan R. Liss, New York (1987)
    2i. U.S. Pat. No. 4,399,216
    2j. *Meth. Enzymol.*, Vol. 118, Academic Press, Orlando (1986)
    2k. Gelvin et al., *Plant Molecular Biology Manual*, Kluwer Academic Publishers, Dudrecht (1990)
  Detection of mutations in the gene of interest
    2l. Maniatis et al., *Molecular Cloning: A Laboratory Manual*, Cold Spring Harbor Laboratory, Cold Spring Harbor, N.Y. (1982)
    2m. Sambrook et al., *Molecular Cloning: A Laboratory Manual*, 2nd Ed., Cold Spring Harbor Laboratory, Cold Spring Harbor, N.Y. (1989)
    2n. *Meth. Enzymol.*, Vol. 68, 100, 101, 152–155, Academic Press, Orlando (1979, 1983, 1987)
    2o. Erlich, *PCR Technology*, Stockton Press, New York (1989)
    2p. Innis et al., *PCR Protocols*, Academic Press, San Diego (1980)
    2q. Orita et al., *Proc. Nat'l Acad. Sci. U.S.A.*, 86:2766–2770 (1989)
    2r. Orita et al., *Genomics*, 5:874–879 (1988)
  Immunodiagnosis
    2s. *Meth. Enzymol.*, Vol. 121, Langone, J. J. and Van Vunakis, H., Ed., Academic Press, Orlando (1986)
    2t. Roitt, *Essential Immunology*, 5th Ed., Blackwell Scientific Publications, Boston, pp. 145–175 (1984)
3. Cited in U.S. Pat. No. 5,217,865
  Isolation of cDNA clones
    3a. Prochownik et al., *J. Biol. Chem.*, 258:8389–8394 (1983)
    3b. Hanahan et al., *Gene*, 10:63–67 (1980)
    3c. Okayama et al., *Mol. Cell. Biol.*, 3:280–289 (1983)
  DNA sequence analysis
    3d. Sanger et al., *Proc. Nat'l Acad. Sci. U.S.A.*, 74:5463–5467 (1977)
    3e. Biggin et al., *Proc. Nat'l Acad. Sci. U.S.A.*, 80:3963–3965 (1983)
  Chromosomal localization
    3f. Shows et al., *Somat. Cell Mol. Genet.*, 10:315–318 (1984)
    3g. Shows et al., *Cytogenet. Cell. Genet.*, 21:99–104 (1978)
    3h. Shows et al., *Adv. Hum. Genet.*, 2:341–452 (1983)
4. Cited in WO 93/06244
  Preparation of primers
    4a. Krieg et al., *Nucl. Acids Res.*, 12:7057–70 (1984)
    4b. Studier et al., *J. Mol. Biol.*, 189:113–130 (1986)
    4c. Lizardi et al., *Biotechnology*, 6:1197–1202 (1988)
    4d. Kramer et al., *J. Mol. Biol.*, 89:719–736 (1974)
    4e. Narang et al., *Meth. Enzymol.*, 68:90 (1979)
    4f. U.S. Pat. No. 4,356,270
    4g. U.S. Pat. No. 4,458,066
    4h. U.S. Pat. No. 4,416,988
    4i. U.S. Pat. No. 4,293,652
    4j. Brown et al., *Meth. Enzymol.*, 68:109 (1979)
  PCR
    4k. U.S. Pat. No. 4,889,818
    4l. *PCR Protocols, A Guide to Methods and Applications*, pp. 245–252, Academic Press, Inc., San Diego, Calif. (1990)
    4m. U.S. Pat. No. 4,683,192
    4n. U.S. Pat. No. 4,683,202
    4o. U.S. Pat. No. 4,800,159
    4p. U.S. Pat. No. 4,965,188
    4q. *PCR Technology: Principles and Applications for DNA Amplification*, H. Erlich, ed., Stockton Press, New York (1989)
    4r. *PCT Protocols: A Guide to Methods and Applications*, Innis et al., eds., Academic Press, San Diego, Calif. (1990)
  Nucleic acid sequence analysis
    4s. U.S. Pat. No. 4,374,120
    4t. U.S. Pat. No. 4,569,790
    4u. EP 0 139 675
    4v. WO 87/02708
    4w. U.S. Pat. No. 4,707,404
    4x. EP 0 212 951
    4y. EP 0 087 636
    4z. Southern, *J. Mol. Biol.*, 98:503 (1975)
  Detection of sequences
    4aa. U.S. Pat. No. 4,582,789
    4ab. U.S. Pat. No. 4,617,621
    4ac. U.S. Pat. No. 4,946,773
5. Cited in WO 90/11092
  Methods of gene transfer in vivo
    5a. Nicolau et al., *Proc. Natl. Acad. Sci. USA*, 80:1068–1072 (1983)
    5b. Kaneda et al., *Science*, 243:375–378 (1989)
    5c. Mannino et al., *Biotechniques*, 6:682–690 (1988)
    5d. Benvenisty et al., *Proc. Natl. Acad. Sci. USA*, 83:9551–9555 (1986)
  Regulation of transient gene therapy
    5e. Kozak, *Nucl. Acids Res.*, 15:8125 (1987)
    5f. Drummond et al., *Nucl. Acids Res.*, 13:7375 (1985)
    5g. Meusing et al., *Cell*, 48:691 (1987)
    5h. Hentze et al., *Proc. Natl. Acad. Sci. USA*, 84:6730 (1987)
    5i. Klemenz et al., *EMBO Journal*, 4:2053 (1985)
    5j. Dolph et al., *J. Virol.*, 62:2059 (1988)
    5k. Pelletier et al., *Nature*, 334, 320 (1988)
    5l. Rodd, *Mol. Biol. Med.*, 5:1 (1988)
6. Cited in WO 91/02796
  DNA screening and diagnosis
    6a. Saiki et al., *Science*, 230:1350–1353 (1985
    6b. Saiki et al., *Nature*, 324:163–166 (1986)
    6c. Caskey, *Science*, 236:1223–1228 (1989)

6d. Landegren et al., *Science*, 242:229–237 (1989)
6e. Wallace et al., *Cold Spring Harbour Symp. Quant. Biol.*, 51:257–261 (1986)
6f. Church et al., *Proc. Natl. Acad. Sci. USA*, 81:1991–1995 (1988)
6g. Flavell et al., *Cell*, 15:25 (1987)
6h. Geever et al., *Proc. Natl. Acad. Sci. USA*, 78:5081 (1981)
6i. Myers et al., *Cold Spring Harbour Sym. Quant. Biol.*, 51:275–284 (1986)
6j. Myers et al., *Science*, 230:1242 (1985)
6k. Cotton et al., *Proc. Natl. Acad. Sci. USA*, 85:4397–4401 (1985)
6l. Landegren et al., *Science*, 241:1077 (1988)
6m. Ward et al., *Proc. Natl. Acad. Sci. USA*, 78:6633–6657 (1981)
6n. Gebeyehu et al., *Nucl. Acids Res.*, 15:4513–4534 (1987)
6o. Wrichnik et al., *Nucl. Acids Res.*, 5:529–542 (1987)
6p. Wong et al., *Nature*, 330:384–386 (1987)
6q. Stofletet al., *Science*, 239:491–494 (1988)
6r. Southern, *J. Mol. Biol.*, 98:503 (1975)
6s. Nagamine et al., *Am. J. Hum. Genet.*, 45:337–339 (1989)
6t. Berk et al., *Proc. Natl. Acad. Sci. USA*, 75:1274 (1978)
6u. Saiki et al., *Proc. Natl. Acad. Sci. USA*, 86:6230–6234 (1989)
6v. Chamberlain et al., *Nucl. Acids Res.*, 16:1141–1155 (1988)
6w. Rommens et al., *Am. J. Hum. Genet.*, 43:645 (1988)

Antibody techniques

6x. O'Brien et al., *Euro. Mol. Biol. Organ. J.*, 6:4003 (1987)
6y. Schreiber et al., *J. Biol. Chem.*, 258:846 (1983)
6z. Veillette et al., *Nature*, 338:257 (1989)
6aa. Matthay et al., *Cancer Res.*, 46:4904 (1986)

RFLP

6ab. Beaudet et al., *Am. J. Hum. Genet.*, 44:319–326
6ac. Brock, *Lancet*, 2:941 (1983)

DNA expression

6ad. Nilsson et al., *EMBO J.*, 4:1075–1080 (1985)
6ae. Smith et al., *Gene*, 67:31–40 (1988)
6af. Sprindler et al., *J. Virol.*, 49:132–141 (1984)
6ag. Burke et al., *Science*, 236:806–812 (1987)
6ah. Timberlake et al., *Science*, 244:1313–1317 (1989)
6ai. Gasser et al., *Science*, 244:1293 (1989)
6aj. Pursel et al., *Science*, 244:1281–1288 (1989)
6ak. Mulligan et al., *Proc. Natl. Acad. Sci. USA*, 78:2072–2076 (1981)
6al. Gluzman, *Cell*, 23:175–182 (1981)
6am. Southern et al., *J. Mol. Appln. Genet.*, 1:327–341 (1982)
6an. Mulligan et al., *Proc. Natl. Acad. Sci. USA*, 78:1078–2076 (1981)
6ao. Gorman et al., *Proc. Natl. Acad. Sci. USA*, 79:6777–6781 (1982)
6ap. Summers et al., *Genetically Altered Viruses and the Environment*, Fields et al., eds., Vol. 22, No. 319–328, Cold Spring Harbour Laboratory Press, Cold Spring Harbour, N.Y. (1985)
6aq. Lee et al., *Nature*, 294:228 (1982)
6ar. Sarver et al., *Mol. Cell. Biol.*, 1:486 (1981)
6as. Sugden et al., *Mol. Cell. Biol.*, 5:410 (1985)
6at. Alt et al., *J. Biol. Chem.*, 253:1357 (1978)
6au. Eb, *Virology*, 52:466 (1973)
6av. Brash et al., *Mol. Cell. Biol.*, 7:2013 (1987)
6aw. Neumann et al., *EMBO J.*, 1:841 (1982)
6ax. Felgner et al., *Proc. Natl. Acad. Sci. USA*, 84:7413 (1987)
6ay. McCuthan et al., *J. Natl. Cancer Inst.*, 41:351 (1968)
6az. Mueller et al., *Cell*, 15:579 (1978)
6ba. Schafner, *Proc. Natl. Acad. Sci. USA*, 72:2163
6bb. Klein et al., *Nature*, 327:70 (1987)
6bc. Bernstein et al., *Genetic Engineering*, 7:235 (1985)
6bd. Ahmad et al., *J. Virol.*, 57:267 (1986)
6be. Spaete et al., *Cell*, 30:295 (1982)
6bf. Gluzman, *Cell*, 23:175 (1981)

Therapies

6bg. Al-Aqwatt, *Science* (1989)
6bh. Capsey et al., *Genetically Engineered Human Therapeutic Drugs*, Stockton Press, New York (1988)
6bi. Friedmann, *Science*, 244:1275 (1989)
6bj. Orkin et al., *Prog. Med. Genet.*, 7:130 (1988)
6bk. McLaughlin et al., *J. Virol.*, 62:1963 (1988)
6bl. Moss et al., *Annu. Rev. Immunol.*, 5:305 (1987)
6bm. Rasmussen et al., *Methods Enzymol.*, 139:642 (1987)
6bn. Margolskee et al., *Mol. Cell. Biol.*, 8:2937 (1988)
6bo. Ostro, *Liposomes*, Marcel-Dekker (1987)
6bp. Felger et al., *Proc. Natl. Acad. Sci. USA*, 84:7413 (1987)

Animal models

6bq. Erickson, *Am. J. Hum. Genet.*, 43:582 (1988)
6br. Johnson et al., *Proc. Natl. Acad. Sci. USA*, 78:3138 (1981)
6bs. Popp et al., *J. Mol. Biol.*, 127:141 (1979)
6bt. Whitney et al., *Proc. Natl. Acad. Sci. USA*, 77:1087 (1980)
6bu. McDonald et al., *Pediatr. Res.*, 23:63 (1988)
6bv. Lewis et al., *Proc. Natl. Acad. Sci. USA*, 85:1962 (1988)
6bw. Camper, *Trends in Genetics* (1988)
6bx. Capecchi, *Science*, 244:1288 (1989)
6by. Soriano et al., *Cell*, 46:19 (1986)
6bz. Capecchi, *Trends Genet.*, 5:70 (1989)
6ca. Kim et al., *Nucleic Acids Res.*, 16:8887 (1988)
6cb. Joyner et al., *Nature*, 338:153 (1989)
6cc. Mansour et al., *Nature*, 336:348 (1988)

---

SEQUENCE LISTING ( 1 ) GENERAL INFORMATION:

( i i i ) NUMBER OF SEQUENCES: 68

( 2 ) INFORMATION FOR SEQ ID NO:1:

( i ) SEQUENCE CHARACTERISTICS:
( A ) LENGTH: 1435 base pairs 5,679,635

37    38

-continued ( B ) TYPE: nucleic acid
( C ) STRANDEDNESS: double
( D ) TOPOLOGY: linear ( i x ) FEATURE:
( A ) NAME/KEY: CDS
( B ) LOCATION: 159..1097

( x i ) SEQUENCE DESCRIPTION: SEQ ID NO:1:

```
TTGTAACAGA AAATTAAAAT ATACTCCACT CAAGGGAATT CTGTACTTTG CCCTTTTGGT        60

AAAGTCTCAT TTACATTTCT AAACCTTTCT TAAGAAAATC GAATTTCCTT TGATCTCTCT       120

TCTGAATTGC AGAAATCAGA TAAAAACTAC TTGGTGAA ATG ACT TCT TGT CAC           173
                                         Met Thr Ser Cys His
                                         1                5

ATT GCT GAA GAA CAT ATA CAA AAG GTT GCT ATC TTT GGA GGA ACC CAT        221
Ile Ala Glu Glu His Ile Gln Lys Val Ala Ile Phe Gly Gly Thr His
             10                  15                  20

GGG AAT GAG CTA ACC GGA GTA TTT CTG GTT AAG CAT TGG CTA GAG AAT        269
Gly Asn Glu Leu Thr Gly Val Phe Leu Val Lys His Trp Leu Glu Asn
         25                  30                  35

GGC GCT GAG ATT CAG AGA ACA GGG CTG GAG GTA AAA CCA TTT ATT ACT        317
Gly Ala Glu Ile Gln Arg Thr Gly Leu Glu Val Lys Pro Phe Ile Thr
     40                  45                  50

AAC CCC AGA GCA GTG AAG AAG TGT ACC AGA TAT ATT GAC TGT GAC CTG        365
Asn Pro Arg Ala Val Lys Lys Cys Thr Arg Tyr Ile Asp Cys Asp Leu
 55                  60                  65

AAT CGC ATT TTT GAC CTT GAA AAT CTT GGC AAA AAA ATG TCA GAA GAT        413
Asn Arg Ile Phe Asp Leu Glu Asn Leu Gly Lys Lys Met Ser Glu Asp
 70                  75                  80                  85

TTG CCA TAT GAA GTG AGA AGG GCT CAA GAA ATA AAT CAT TTA TTT GGT        461
Leu Pro Tyr Glu Val Arg Arg Ala Gln Glu Ile Asn His Leu Phe Gly
             90                  95                 100

CCA AAA GAC AGT GAA GAT TCC TAT GAC ATT ATT TTT GAC CTT CAC AAC        509
Pro Lys Asp Ser Glu Asp Ser Tyr Asp Ile Ile Phe Asp Leu His Asn
        105                 110                 115

ACC ACC TCT AAC ATG GGG TGC ACT CTT ATT CTT GAG GAT TCC AGG AAT        557
Thr Thr Ser Asn Met Gly Cys Thr Leu Ile Leu Glu Asp Ser Arg Asn
    120                 125                 130

AAC TTT TTA ATT CAG ATG TTT CAT TAC ATT AAG ACT TCT CTG GCT CCA        605
Asn Phe Leu Ile Gln Met Phe His Tyr Ile Lys Thr Ser Leu Ala Pro
135                 140                 145

CTA CCC TGC TAC GTT TAT CTG ATT GAG CAT CCT TCC CTC AAA TAT GCG        653
Leu Pro Cys Tyr Val Tyr Leu Ile Glu His Pro Ser Leu Lys Tyr Ala
150                 155                 160                 165

ACC ACT CGT TCC ATA GCC AAG TAT CCT GTG GGT ATA GAA GTT GGT CCT        701
Thr Thr Arg Ser Ile Ala Lys Tyr Pro Val Gly Ile Glu Val Gly Pro
            170                 175                 180

CAG CCT CAA GGG GTT CTG AGA GCT GAT ATC TTG GAT CAA ATG AGA AAA        749
Gln Pro Gln Gly Val Leu Arg Ala Asp Ile Leu Asp Gln Met Arg Lys
        185                 190                 195

ATG ATT AAA CAT GCT CTT GAT TTT ATA CAT CAT TTC AAT GAA GGA AAA        797
Met Ile Lys His Ala Leu Asp Phe Ile His His Phe Asn Glu Gly Lys
    200                 205                 210

GAA TTT CCT CCC TGC GCC ATT GAG GTC TAT AAA ATT ATA GAG AAG GTT        845
Glu Phe Pro Pro Cys Ala Ile Glu Val Tyr Lys Ile Ile Glu Lys Val
215                 220                 225

GAT TAC CCC CGG GAT GAA AAT GGA GAA ATT GCT GCT ATC ATC CAT CCT        893
Asp Tyr Pro Arg Asp Glu Asn Gly Glu Ile Ala Ala Ile Ile His Pro
230                 235                 240                 245

AAT CTG CAG GAT CAA GAC TGG AAA CCA CTG CAT CCT GGG GAT CCC ATG        941
Asn Leu Gln Asp Gln Asp Trp Lys Pro Leu His Pro Gly Asp Pro Met
```

|  | 250 | | | | | 255 | | | | | 260 | | | | |
|---|---|---|---|---|---|---|---|---|---|---|---|---|---|---|---|
| TTT | TTA | ACT | CTT | GAT | GGG | AAG | ACG | ATC | CCA | CTG | GGC | GGA | GAC | TGT | ACC | 989 |
| Phe | Leu | Thr | Leu | Asp | Gly | Lys | Thr | Ile | Pro | Leu | Gly | Gly | Asp | Cys | Thr |
| | | 265 | | | | | 270 | | | | | 275 | | | |
| GTG | TAC | CCC | GTG | TTT | GTG | AAT | GAG | GCC | GCA | TAT | TAC | GAA | AAG | AAA | GAA | 1037 |
| Val | Tyr | Pro | Val | Phe | Val | Asn | Glu | Ala | Ala | Tyr | Tyr | Glu | Lys | Lys | Glu |
| | | 280 | | | | 285 | | | | | 290 | | | |
| GCT | TTT | GCA | AAG | ACA | ACT | AAA | CTA | ACG | CTC | AAT | GCA | AAA | AGT | ATT | CGC | 1085 |
| Ala | Phe | Ala | Lys | Thr | Thr | Lys | Leu | Thr | Leu | Asn | Ala | Lys | Ser | Ile | Arg |
| | 295 | | | | 300 | | | | 305 | | | | |
| TGC | TGT | TTA | CAT | TAGAAATCAC | TTCCAGCTTA | CATCTTACAC | GGTGTCTTAC | | | | | | | | | 1137 |
| Cys | Cys | Leu | His |
| 310 |

```
AAATTCTGCT AGTCTGTAAG CTCCTTAAGA GTAGGGTTGT GCCTTATTCA ACTGCATACA    1197

TAGCTCCTAG CACAGTGCCT TATTCGGTAG GCATCAAGC  AAATTTCTTA AATTAATTAA    1257

TATATCTTTA AAGATATCAT ATTTTATGTA TGTAGCTTAT TCAAAGAAGT GTTTCCTATT    1317

TCTATATAGT TTATTATACA TGATACTTGG GTAGCTCAAC ATTCTTAATA AACAGCCTTT    1377

GTATTCAGAA TATAAAATTG AAATAGATAT ATATAAAGTT AAAAAAAAA  AAAAAAA       1435
```

(2) INFORMATION FOR SEQ ID NO:2:

(i) SEQUENCE CHARACTERISTICS:
        (A) LENGTH: 313 amino acids
        (B) TYPE: amino acid
        (D) TOPOLOGY: linear (ix) FEATURE:
        (A) NAME/KEY: Modified-site
        (B) LOCATION: 83
        (D) OTHER INFORMATION: /note= "Phosphorylation site"

(ix) FEATURE:
        (A) NAME/KEY: Modified-site
        (B) LOCATION: 105
        (D) OTHER INFORMATION: /note= "Phosphorylation site"

(ix) FEATURE:
        (A) NAME/KEY: Modified-site
        (B) LOCATION: 108
        (D) OTHER INFORMATION: /note= "Phosphorylation site"

(ix) FEATURE:
        (A) NAME/KEY: Modified-site
        (B) LOCATION: 146
        (D) OTHER INFORMATION: /note= "Phosphorylation site"

(ix) FEATURE:
        (A) NAME/KEY: Modified-site
        (B) LOCATION: 264
        (D) OTHER INFORMATION: /note= "Phosphorylation site"

(ix) FEATURE:
        (A) NAME/KEY: Modified-site
        (B) LOCATION: 117
        (D) OTHER INFORMATION: /note= "Potential N-glycosylation
            site"

(ix) FEATURE:
        (A) NAME/KEY: Active-site
        (B) LOCATION: 18..24
        (D) OTHER INFORMATION: /note= "Consensus sequence
            predicted to be involved in catalysis"

(ix) FEATURE:
        (A) NAME/KEY: Active-site
        (B) LOCATION: 275..278
        (D) OTHER INFORMATION: /note= "Consensus sequence
            predicted to be involved in catalysis"

(ix) FEATURE:

(A) NAME/KEY: Active-site
(B) LOCATION: 283..289
(D) OTHER INFORMATION: /note= "Consensus sequence
predicted to be involved in catalysis"

(xi) SEQUENCE DESCRIPTION: SEQ ID NO:2:

| Met | Thr | Ser | Cys | His | Ile | Ala | Glu | Glu | His | Ile | Gln | Lys | Val | Ala | Ile |
|---|---|---|---|---|---|---|---|---|---|---|---|---|---|---|---|
| 1 | | | | 5 | | | | | 10 | | | | | 15 | |
| Phe | Gly | Gly | Thr | His | Gly | Asn | Glu | Leu | Thr | Gly | Val | Phe | Leu | Val | Lys |
| | | | 20 | | | | | 25 | | | | | 30 | | |
| His | Trp | Leu | Glu | Asn | Gly | Ala | Glu | Ile | Gln | Arg | Thr | Gly | Leu | Glu | Val |
| | | | 35 | | | | 40 | | | | | 45 | | | |
| Lys | Pro | Phe | Ile | Thr | Asn | Pro | Arg | Ala | Val | Lys | Lys | Cys | Thr | Arg | Tyr |
| | 50 | | | | | 55 | | | | | 60 | | | | |
| Ile | Asp | Cys | Asp | Leu | Asn | Arg | Ile | Phe | Asp | Leu | Glu | Asn | Leu | Gly | Lys |
| 65 | | | | | 70 | | | | | 75 | | | | | 80 |
| Lys | Met | Ser | Glu | Asp | Leu | Pro | Tyr | Glu | Val | Arg | Arg | Ala | Gln | Glu | Ile |
| | | | | 85 | | | | | 90 | | | | | 95 | |
| Asn | His | Leu | Phe | Gly | Pro | Lys | Asp | Ser | Glu | Asp | Ser | Tyr | Asp | Ile | Ile |
| | | | 100 | | | | | 105 | | | | | 110 | | |
| Phe | Asp | Leu | His | Asn | Thr | Thr | Ser | Asn | Met | Gly | Cys | Thr | Leu | Ile | Leu |
| | | | 115 | | | | | 120 | | | | | 125 | | |
| Glu | Asp | Ser | Arg | Asn | Asn | Phe | Leu | Ile | Gln | Met | Phe | His | Tyr | Ile | Lys |
| | | 130 | | | | | 135 | | | | | 140 | | | |
| Thr | Ser | Leu | Ala | Pro | Leu | Pro | Cys | Tyr | Val | Tyr | Leu | Ile | Glu | His | Pro |
| 145 | | | | | 150 | | | | | 155 | | | | | 160 |
| Ser | Leu | Lys | Tyr | Ala | Thr | Thr | Arg | Ser | Ile | Ala | Lys | Tyr | Pro | Val | Gly |
| | | | | 165 | | | | | 170 | | | | | 175 | |
| Ile | Glu | Val | Gly | Pro | Gln | Pro | Gln | Gly | Val | Leu | Arg | Ala | Asp | Ile | Leu |
| | | | 180 | | | | | 185 | | | | | 190 | | |
| Asp | Gln | Met | Arg | Lys | Met | Ile | Lys | His | Ala | Leu | Asp | Phe | Ile | His | His |
| | | 195 | | | | | 200 | | | | | 205 | | | |
| Phe | Asn | Glu | Gly | Lys | Glu | Phe | Pro | Pro | Cys | Ala | Ile | Glu | Val | Tyr | Lys |
| | 210 | | | | | 215 | | | | | 220 | | | | |
| Ile | Ile | Glu | Lys | Val | Asp | Tyr | Pro | Arg | Asp | Glu | Asn | Gly | Glu | Ile | Ala |
| 225 | | | | | 230 | | | | | 235 | | | | | 240 |
| Ala | Ile | Ile | His | Pro | Asn | Leu | Gln | Asp | Gln | Asp | Trp | Lys | Pro | Leu | His |
| | | | | 245 | | | | | 250 | | | | | 255 | |
| Pro | Gly | Asp | Pro | Met | Phe | Leu | Thr | Leu | Asp | Gly | Lys | Thr | Ile | Pro | Leu |
| | | | 260 | | | | | 265 | | | | | 270 | | |
| Gly | Gly | Asp | Cys | Thr | Val | Tyr | Pro | Val | Phe | Val | Asn | Glu | Ala | Ala | Tyr |
| | | 275 | | | | | 280 | | | | | 285 | | | |
| Tyr | Glu | Lys | Lys | Glu | Ala | Phe | Ala | Lys | Thr | Thr | Lys | Leu | Thr | Leu | Asn |
| | 290 | | | | | 295 | | | | | 300 | | | | |
| Ala | Lys | Ser | Ile | Arg | Cys | Cys | Leu | His | | | | | | | |
| 305 | | | | | 310 | | | | | | | | | | |

(2) INFORMATION FOR SEQ ID NO:3:

(i) SEQUENCE CHARACTERISTICS:
(A) LENGTH: 313 amino acids
(B) TYPE: amino acid
(D) TOPOLOGY: linear (ix) FEATURE:
(A) NAME/KEY: Region
(B) LOCATION: 6
(D) OTHER INFORMATION: /note= "This is isoleucine in
human, valine in bovine. This is a very conservative substitution."

( i x ) FEATURE:
    ( A ) NAME/KEY: Region
    ( B ) LOCATION: 9
    ( D ) OTHER INFORMATION: /note= "This is glutamic acid in
        human, aspartic acid in bovine. This is a very
        conservative substitution."

( i x ) FEATURE:
    ( A ) NAME/KEY: Region
    ( B ) LOCATION: 10
    ( D ) OTHER INFORMATION: /note= "This is histidine in human,
        proline in bovine. This is a conservative
        substitution."

( i x ) FEATURE:
    ( A ) NAME/KEY: Region
    ( B ) LOCATION: 12
    ( D ) OTHER INFORMATION: /note= "This is glutamine in human,
        lysine in bovine. This is a very conservative
        substitution."

( i x ) FEATURE:
    ( A ) NAME/KEY: Region
    ( B ) LOCATION: 38
    ( D ) OTHER INFORMATION: /note= "This is glycine in human,
        serine in bovine. This is a very conservative
        substitution."

( i x ) FEATURE:
    ( A ) NAME/KEY: Region
    ( B ) LOCATION: 39
    ( D ) OTHER INFORMATION: /note= "This is alanine in human,
        threonine in bovine. This is a very conservative
        substitution."

( i x ) FEATURE:
    ( A ) NAME/KEY: Region
    ( B ) LOCATION: 72
    ( D ) OTHER INFORMATION: /note= "This is isoleucine in
        human, valine in bovine. This is a very
        conservative substitution."

( i x ) FEATURE:
    ( A ) NAME/KEY: Region
    ( B ) LOCATION: 75
    ( D ) OTHER INFORMATION: /note= "This is leucine in human,
        proline in bovine. This is not a conservative
        substitution."

( i x ) FEATURE:
    ( A ) NAME/KEY: Region
    ( B ) LOCATION: 82
    ( D ) OTHER INFORMATION: /note= "This is methionine in
        human, lysine in bovine. This is a conservative
        substitution."

( i x ) FEATURE:
    ( A ) NAME/KEY: Region
    ( B ) LOCATION: 134
    ( D ) OTHER INFORMATION: /note= "This is asparagine in
        human, aspartic acid in bovine. This is a very
        conservative substitution."

( i x ) FEATURE:
    ( A ) NAME/KEY: Region
    ( B ) LOCATION: 200
    ( D ) OTHER INFORMATION: /note= "This is lysine in human,
        glutamine in bovine. This is a very conservative
        substitution."

( i x ) FEATURE:
    ( A ) NAME/KEY: Region
    ( B ) LOCATION: 208
    ( D ) OTHER INFORMATION: /note= "This is histidine in human,
        asparagine in bovine. This is a very conservative
        substitution."

( i x ) FEATURE:

( A ) NAME/KEY: Region
( B ) LOCATION: 226
( D ) OTHER INFORMATION: /note= "This is isoleucine in
human, methionine in bovine. This is a very
conservative substitution."

( i x ) FEATURE:
( A ) NAME/KEY: Region
( B ) LOCATION: 227
( D ) OTHER INFORMATION: /note= "This is glutamic acid in
human, arginine in bovine. This is not a
conservative substitution."

( i x ) FEATURE:
( A ) NAME/KEY: Region
( B ) LOCATION: 234
( D ) OTHER INFORMATION: /note= "This is aspartic acid in
human, asparagine in bovine. This is a very
conservative substitution."

( i x ) FEATURE:
( A ) NAME/KEY: Region
( B ) LOCATION: 236
( D ) OTHER INFORMATION: /note= "This is asparagine in
human, serine in bovine. This is a very
conservative substitution."

( i x ) FEATURE:
( A ) NAME/KEY: Region
( B ) LOCATION: 240
( D ) OTHER INFORMATION: /note= "This is alanine in human,
serine in bovine. This is a very conservative
substitution."

( i x ) FEATURE:
( A ) NAME/KEY: Region
( B ) LOCATION: 246
( D ) OTHER INFORMATION: /note= "This is asparagine in
human, lysine in bovine. This is a very
conservative substitution."

( i x ) FEATURE:
( A ) NAME/KEY: Region
( B ) LOCATION: 258
( D ) OTHER INFORMATION: /note= "This is glycine in human,
glutamic acid in bovine. This is a conservative
substitution."

( i x ) FEATURE:
( A ) NAME/KEY: Region
( B ) LOCATION: 261
( D ) OTHER INFORMATION: /note= "This is methionine in
human, valine in bovine. This is a very
conservative substitution."

( i x ) FEATURE:
( A ) NAME/KEY: Region
( B ) LOCATION: 276
( D ) OTHER INFORMATION: /note= "This is cysteine in human,
glutamine in bovine. This is not a conservative
substitution."

( i x ) FEATURE:
( A ) NAME/KEY: Region
( B ) LOCATION: 306
( D ) OTHER INFORMATION: /note= "This is lysine in human,
asparagine in bovine. This is a very conservative
substitution."

( i x ) FEATURE:
( A ) NAME/KEY: Region
( B ) LOCATION: 310
( D ) OTHER INFORMATION: /note= "This is cysteine in human,
serine in bovine. This is a conservative substitution."

( i x ) FEATURE:
( A ) NAME/KEY: Region
( B ) LOCATION: 311
( D ) OTHER INFORMATION: /note= "This is cysteine in human,
serine in bovine. This is a conservative substitution."

( i x ) FEATURE:
    ( A ) NAME/KEY: Modified-site
    ( B ) LOCATION: 83
    ( D ) OTHER INFORMATION: /note= "Phosphorylation site"

( i x ) FEATURE:
    ( A ) NAME/KEY: Modified-site
    ( B ) LOCATION: 105
    ( D ) OTHER INFORMATION: /note= "Phosphorylation site"

( i x ) FEATURE:
    ( A ) NAME/KEY: Modified-site
    ( B ) LOCATION: 108
    ( D ) OTHER INFORMATION: /note= "Phosphorylation site"

( i x ) FEATURE:
    ( A ) NAME/KEY: Modified-site
    ( B ) LOCATION: 146
    ( D ) OTHER INFORMATION: /note= "Phosphorylation site"

( i x ) FEATURE:
    ( A ) NAME/KEY: Modified-site
    ( B ) LOCATION: 264
    ( D ) OTHER INFORMATION: /note= "Phosphorylation site"

( i x ) FEATURE:
    ( A ) NAME/KEY: Modified-site
    ( B ) LOCATION: 117
    ( D ) OTHER INFORMATION: /note= "Potential N-glycosylation site"

( i x ) FEATURE:
    ( A ) NAME/KEY: Active-site
    ( B ) LOCATION: 18..24
    ( D ) OTHER INFORMATION: /note= "Consensus sequence
        predicted to be involved in catalysis"

( i x ) FEATURE:
    ( A ) NAME/KEY: Active-site
    ( B ) LOCATION: 275..278
    ( D ) OTHER INFORMATION: /note= "Consensus sequence
        predicted to be involved in catalysis"

( i x ) FEATURE:
    ( A ) NAME/KEY: Active-site
    ( B ) LOCATION: 283..289
    ( D ) OTHER INFORMATION: /note= "Consensus sequence
        predicted to be involved in catalysis"

( x i ) SEQUENCE DESCRIPTION: SEQ ID NO:3:

```
Met Thr Ser Cys His Xaa Ala Glu Xaa Xaa Ile Xaa Lys Val Ala Ile
 1               5                  10                  15

Phe Gly Gly Thr His Gly Asn Glu Leu Thr Gly Val Phe Leu Val Lys
                20                  25                  30

His Trp Leu Glu Asn Xaa Xaa Glu Ile Gln Arg Thr Gly Leu Glu Val
            35                  40                  45

Lys Pro Phe Ile Thr Asn Pro Arg Ala Val Lys Lys Cys Thr Arg Tyr
        50                  55                  60

Ile Asp Cys Asp Leu Asn Arg Xaa Phe Asp Xaa Glu Asn Leu Gly Lys
65                  70                  75                  80

Lys Xaa Ser Glu Asp Leu Pro Tyr Glu Val Arg Arg Ala Gln Glu Ile
                85                  90                  95

Asn His Leu Phe Gly Pro Lys Asp Ser Glu Asp Ser Tyr Asp Ile Ile
                100                 105                 110

Phe Asp Leu His Asn Thr Thr Ser Asn Met Gly Cys Thr Leu Ile Leu
            115                 120                 125

Glu Asp Ser Arg Asn Xaa Phe Leu Ile Gln Met Phe His Tyr Ile Lys
        130                 135                 140

Thr Ser Leu Ala Pro Leu Pro Cys Tyr Val Tyr Leu Ile Glu His Pro
145                 150                 155                 160
```

```
Ser  Leu  Lys  Tyr  Ala  Thr  Thr  Arg  Ser  Ile  Ala  Lys  Tyr  Pro  Val  Gly
                    165                      170                    175

Ile  Glu  Val  Gly  Pro  Gln  Pro  Gln  Gly  Val  Leu  Arg  Ala  Asp  Ile  Leu
               180                      185                         190

Asp  Gln  Met  Arg  Lys  Met  Ile  Xaa  His  Ala  Leu  Asp  Phe  Ile  His  Xaa
          195                      200                         205

Phe  Asn  Glu  Gly  Lys  Glu  Phe  Pro  Pro  Cys  Ala  Ile  Glu  Val  Tyr  Lys
     210                      215                         220

Ile  Xaa  Xaa  Lys  Val  Asp  Tyr  Pro  Arg  Xaa  Glu  Xaa  Gly  Glu  Ile  Xaa
225                      230                      235                         240

Ala  Ile  Ile  His  Pro  Xaa  Leu  Gln  Asp  Gln  Asp  Trp  Lys  Pro  Leu  His
                    245                      250                         255

Pro  Xaa  Asp  Pro  Xaa  Phe  Leu  Thr  Leu  Asp  Gly  Lys  Thr  Ile  Pro  Leu
               260                      265                    270

Gly  Gly  Asp  Xaa  Thr  Val  Tyr  Pro  Val  Phe  Val  Asn  Glu  Ala  Ala  Tyr
               275                    280                    285

Tyr  Glu  Lys  Lys  Glu  Ala  Phe  Ala  Lys  Thr  Thr  Lys  Leu  Thr  Leu  Asn
     290                      295                    300

Ala  Xaa  Ser  Ile  Arg  Xaa  Xaa  Leu  His
305                      310
```

( 2 ) INFORMATION FOR SEQ ID NO:4:

( i ) SEQUENCE CHARACTERISTICS:
        ( A ) LENGTH: 313 amino acids
        ( B ) TYPE: amino acid
        ( D ) TOPOLOGY: linear ( i x ) FEATURE:
        ( A ) NAME/KEY: Modified-site
        ( B ) LOCATION: 83
        ( D ) OTHER INFORMATION: /note= "Phophorylation site"

( i x ) FEATURE:
        ( A ) NAME/KEY: Modified-site
        ( B ) LOCATION: 105
        ( D ) OTHER INFORMATION: /note= "Phosphorylation site"

( i x ) FEATURE:
        ( A ) NAME/KEY: Modified-site
        ( B ) LOCATION: 108
        ( D ) OTHER INFORMATION: /note= "Phosphorylation site"

( i x ) FEATURE:
        ( A ) NAME/KEY: Modified-site
        ( B ) LOCATION: 146
        ( D ) OTHER INFORMATION: /note= "Phosphorylation site"

( i x ) FEATURE:
        ( A ) NAME/KEY: Modified-site
        ( B ) LOCATION: 264
        ( D ) OTHER INFORMATION: /note= "Phosphorylation site"

( i x ) FEATURE:
        ( A ) NAME/KEY: Modified-site
        ( B ) LOCATION: 117
        ( D ) OTHER INFORMATION: /note= "Potential N-glycosylation
            site"

( i x ) FEATURE:
        ( A ) NAME/KEY: Active-site
        ( B ) LOCATION: 18..24
        ( D ) OTHER INFORMATION: /note= "Consensus sequence
            predicted to be involved in catalysis"

( i x ) FEATURE:
        ( A ) NAME/KEY: Active-site
        ( B ) LOCATION: 275..278
        ( D ) OTHER INFORMATION: /note= "Consensus sequence ( i x ) FEATURE:
  ( A ) NAME/KEY: Active-site
  ( B ) LOCATION: 283..289
  ( D ) OTHER INFORMATION: /note= "Consensus sequence predicted to be involved in catalysis"

( x i ) SEQUENCE DESCRIPTION: SEQ ID NO:4:

```
Met Thr Ser Cys His Val Ala Glu Asp Pro Ile Lys Lys Val Ala Ile
1               5                   10                  15

Phe Gly Gly Thr His Gly Asn Glu Leu Thr Gly Val Phe Leu Val Lys
            20                  25                  30

His Trp Leu Glu Asn Ser Thr Glu Ile Gln Arg Thr Gly Leu Glu Val
            35                  40                  45

Lys Pro Phe Ile Thr Asn Pro Arg Ala Val Lys Lys Cys Thr Arg Tyr
    50                  55                  60

Ile Asp Cys Asp Leu Asn Arg Val Phe Asp Pro Glu Asn Leu Gly Lys
65                  70                  75                  80

Lys Lys Ser Glu Asp Leu Pro Tyr Glu Val Arg Arg Ala Gln Glu Ile
            85                  90                  95

Asn His Leu Phe Gly Pro Lys Asp Ser Glu Asp Ser Tyr Asp Ile Ile
            100                 105                 110

Phe Asp Leu His Asn Thr Thr Ser Asn Met Gly Cys Thr Leu Ile Leu
            115                 120                 125

Glu Asp Ser Arg Asn Asp Phe Leu Ile Gln Met Phe His Tyr Ile Lys
    130                 135                 140

Thr Ser Leu Ala Pro Leu Pro Cys Tyr Val Tyr Leu Ile Glu His Pro
145                 150                 155                 160

Ser Leu Lys Tyr Ala Thr Thr Arg Ser Ile Ala Lys Tyr Pro Val Gly
                165                 170                 175

Ile Glu Val Gly Pro Gln Pro Gln Gly Val Leu Arg Ala Asp Ile Leu
            180                 185                 190

Asp Gln Met Arg Lys Met Ile Gln His Ala Leu Asp Phe Ile His Asn
        195                 200                 205

Phe Asn Glu Gly Lys Glu Phe Pro Pro Cys Ala Ile Glu Val Tyr Lys
    210                 215                 220

Ile Met Arg Lys Val Asp Tyr Pro Arg Asn Glu Ser Gly Glu Ile Ser
225                 230                 235                 240

Ala Ile Ile His Pro Lys Leu Gln Asp Gln Asp Trp Lys Pro Leu His
                245                 250                 255

Pro Glu Asp Pro Val Phe Leu Thr Leu Asp Gly Lys Thr Ile Pro Leu
            260                 265                 270

Gly Gly Asp Gln Thr Val Tyr Pro Val Phe Val Asn Glu Ala Ala Tyr
        275                 280                 285

Tyr Glu Lys Lys Glu Ala Phe Ala Lys Thr Thr Lys Leu Thr Leu Asn
    290                 295                 300

Ala Asn Ser Ile Arg Ser Ser Leu His
305                 310
```

( 2 ) INFORMATION FOR SEQ ID NO:5:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

AACCCTACTC TTAAGGAC                                                                18

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 1
        ( D ) OTHER INFORMATION: /mod_base= OTHER
            / note= "The M13 universal primer tag is attached
            to base number 1."

( x i ) SEQUENCE DESCRIPTION: SEQ ID NO:6:

CCGGGATGAA AATGGAGAA                                                               19

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 1
        ( D ) OTHER INFORMATION: /mod_base= OTHER
            / note= "The M13 reverse primer tag is attached to
            base 1."

( x i ) SEQUENCE DESCRIPTION: SEQ ID NO:7:

ACCGTGTAAG ATGTAAGC                                                                18

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

AGGATCAAGA CTGGAAACC                                                               19

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GTAAGACACC GTGTAAGATG                                                              20

( 2 ) INFORMATION FOR SEQ ID NO:10:

( i ) SEQUENCE CHARACTERISTICS:
        ( A ) LENGTH: 7 amino acids
        ( B ) TYPE: amino acid
        ( D ) TOPOLOGY: linear ( i i i ) HYPOTHETICAL: NO ( v ) FRAGMENT TYPE: internal ( x i ) SEQUENCE DESCRIPTION: SEQ ID NO:10:

Gly Gly Thr His Gly Asn Glu
1               5

( 2 ) INFORMATION FOR SEQ ID NO:11:

( i ) SEQUENCE CHARACTERISTICS:
( A ) LENGTH: 7 amino acids
( B ) TYPE: amino acid
( D ) TOPOLOGY: linear ( i i i ) HYPOTHETICAL: NO ( v ) FRAGMENT TYPE: internal ( x i ) SEQUENCE DESCRIPTION: SEQ ID NO:11:

Val Asn Glu Ala Ala Tyr Tyr
1               5

( 2 ) INFORMATION FOR SEQ ID NO:12:

( i ) SEQUENCE CHARACTERISTICS:
( A ) LENGTH: 7 amino acids
( B ) TYPE: amino acid
( D ) TOPOLOGY: linear ( v ) FRAGMENT TYPE: internal ( x i ) SEQUENCE DESCRIPTION: SEQ ID NO:12:

Val Xaa Glu Xaa Xaa Xaa Tyr
1               5

( 2 ) INFORMATION FOR SEQ ID NO:13:

( i ) SEQUENCE CHARACTERISTICS:
( A ) LENGTH: 26 amino acids
( B ) TYPE: amino acid
( D ) TOPOLOGY: linear ( i i i ) HYPOTHETICAL: NO ( v ) FRAGMENT TYPE: internal ( x i ) SEQUENCE DESCRIPTION: SEQ ID NO:13:

Leu Glu Asn Ser Thr Glu Ile Gln Arg Thr Gly Leu Glu Val Lys Pro
1               5                   10                  15

Phe Ile Thr Asn Pro Arg Ala Val Lys Lys
            20                  25

( 2 ) INFORMATION FOR SEQ ID NO:14:

( i ) SEQUENCE CHARACTERISTICS:
( A ) LENGTH: 37 amino acids
( B ) TYPE: amino acid
( D ) TOPOLOGY: linear ( i i i ) HYPOTHETICAL: NO ( v ) FRAGMENT TYPE: internal ( x i ) SEQUENCE DESCRIPTION: SEQ ID NO:14:

Lys Pro Leu Ile Pro Xaa Asp Pro Val Phe Leu Thr Leu Asp Gly Lys
1               5                   10                  15

Thr Ile Ser Leu Gly Gly Asp Gln Thr Xaa Tyr Pro Xaa Phe Xaa Asn
            20                  25                  30

Glu Ala Ala Tyr Tyr
            35

( 2 ) INFORMATION FOR SEQ ID NO:15:

( i ) SEQUENCE CHARACTERISTICS:
    ( A ) LENGTH: 24 amino acids
    ( B ) TYPE: amino acid
    ( D ) TOPOLOGY: linear ( i i i ) HYPOTHETICAL: NO ( v ) FRAGMENT TYPE: internal ( x i ) SEQUENCE DESCRIPTION: SEQ ID NO:15:

```
Xaa Lys Val Asp Tyr Pro Arg Asn Glu Ser Gly Glu Ile Ser Ala Ile
 1               5                  10                  15

Ile His Pro Lys Leu Gln Asp Gln
                20
```

( 2 ) INFORMATION FOR SEQ ID NO:16:

( i ) SEQUENCE CHARACTERISTICS:
    ( A ) LENGTH: 16 amino acids
    ( B ) TYPE: amino acid
    ( D ) TOPOLOGY: linear ( i i i ) HYPOTHETICAL: NO ( v ) FRAGMENT TYPE: internal ( x i ) SEQUENCE DESCRIPTION: SEQ ID NO:16:

```
Xaa Xaa Xaa Ala Leu Asp Phe Ile Xaa Asn Phe Xaa Glu Xaa Lys Glu
 1               5                  10                  15
```

( 2 ) INFORMATION FOR SEQ ID NO:17:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 6
    ( D ) OTHER INFORMATION: /mod_base= i ( i x ) FEATURE:
    ( A ) NAME/KEY: modified_base
    ( B ) LOCATION: 15
    ( D ) OTHER INFORMATION: /mod_base= i ( i x ) FEATURE:
    ( A ) NAME/KEY: modified_base
    ( B ) LOCATION: 16
    ( D ) OTHER INFORMATION: /mod_base= i ( i x ) FEATURE:
    ( A ) NAME/KEY: modified_base
    ( B ) LOCATION: 18
    ( D ) OTHER INFORMATION: /mod_base= i ( x i ) SEQUENCE DESCRIPTION: SEQ ID NO:17:

AARGTNGAYT AYCCNNGNAA    20

( 2 ) INFORMATION FOR SEQ ID NO:18:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i x ) FEATURE:
  ( A ) NAME/KEY: modified_base
  ( B ) LOCATION: 9
  ( D ) OTHER INFORMATION: /mod_base= i ( i x ) FEATURE:
  ( A ) NAME/KEY: modified_base
  ( B ) LOCATION: 11
  ( D ) OTHER INFORMATION: /mod_base= i ( i x ) FEATURE:
  ( A ) NAME/KEY: modified_base
  ( B ) LOCATION: 15
  ( D ) OTHER INFORMATION: /mod_base= i ( x i ) SEQUENCE DESCRIPTION: SEQ ID NO:18:

TGRTC Y TGNA N Y TTNGGRTG    20

( 2 ) INFORMATION FOR SEQ ID NO:19:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:19:

CCGTGTACCC AGTGTT    16

( 2 ) INFORMATION FOR SEQ ID NO:20:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:20:

CTTCTGAATT GCAGAAATCA    20

( 2 ) INFORMATION FOR SEQ ID NO:21:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:21:

GTAAGACACC GTGTAAGATG    20

( 2 ) INFORMATION FOR SEQ ID NO:22:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i x ) FEATURE:
  ( A ) NAME/KEY: modified_base
  ( B ) LOCATION: 6
  ( D ) OTHER INFORMATION: /mod_base= i ( i x ) FEATURE:
  ( A ) NAME/KEY: modified_base
  ( B ) LOCATION: 9
  ( D ) OTHER INFORMATION: /mod_base= i ( i x ) FEATURE:
  ( A ) NAME/KEY: modified_base
  ( B ) LOCATION: 18

( D ) OTHER INFORMATION: /mod_base= i ( i x ) FEATURE:
                    ( A ) NAME/KEY: modified_base
                    ( B ) LOCATION: 21
                    ( D ) OTHER INFORMATION: /mod_base= i ( x i ) SEQUENCE DESCRIPTION: SEQ ID NO:22:

GGRTANACNG T Y TGRTCNCC NCC                                                                                        23

( 2 ) INFORMATION FOR SEQ ID NO:23:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i x ) FEATURE:
                    ( A ) NAME/KEY: modified_base
                    ( B ) LOCATION: 3
                    ( D ) OTHER INFORMATION: /mod_base= i ( i x ) FEATURE:
                    ( A ) NAME/KEY: modified_base
                    ( B ) LOCATION: 6
                    ( D ) OTHER INFORMATION: /mod_base= i ( i x ) FEATURE:
                    ( A ) NAME/KEY: modified_base
                    ( B ) LOCATION: 9
                    ( D ) OTHER INFORMATION: /mod_base= i ( i x ) FEATURE:
                    ( A ) NAME/KEY: modified_base
                    ( B ) LOCATION: 12
                    ( D ) OTHER INFORMATION: /mod_base= i ( x i ) SEQUENCE DESCRIPTION: SEQ ID NO:23:

CCNMGNGCNG TNAARAARTG                                                                                              20

( 2 ) INFORMATION FOR SEQ ID NO:24:

( i ) SEQUENCE CHARACTERISTICS:
                    ( A ) LENGTH: 4 amino acids
                    ( B ) TYPE: amino acid
                    ( D ) TOPOLOGY: linear ( i i i ) HYPOTHETICAL: NO ( v ) FRAGMENT TYPE: internal ( x i ) SEQUENCE DESCRIPTION: SEQ ID NO:24:

Asp Cys Thr Val
    1

( 2 ) INFORMATION FOR SEQ ID NO:25:

( i ) SEQUENCE CHARACTERISTICS:
                    ( A ) LENGTH: 7 amino acids
                    ( B ) TYPE: amino acid
                    ( D ) TOPOLOGY: linear ( v ) FRAGMENT TYPE: internal ( i x ) FEATURE:
                    ( A ) NAME/KEY: Active-site
                    ( B ) LOCATION: 1..7
                    ( D ) OTHER INFORMATION: /note= "Consensus sequence of catalytic
                            center in esterases"

( i x ) FEATURE:
                    ( A ) NAME/KEY: Region
                    ( B ) LOCATION: 5

(D) OTHER INFORMATION: /note= "Amino acid 5 is glycine or alanine"

(ix) FEATURE:
  (A) NAME/KEY: Region
  (B) LOCATION: 7
  (D) OTHER INFORMATION: /note= "Amino acid 7 is glutamic acid or aspartic acid"

(xi) SEQUENCE DESCRIPTION: SEQ ID NO:25:

Gly Xaa Xaa His Xaa Xaa Xaa
1                5

(2) INFORMATION FOR SEQ ID NO:26:

(i) SEQUENCE CHARACTERISTICS:
    (A) LENGTH: 4 amino acids
    (B) TYPE: amino acid
    (D) TOPOLOGY: linear (v) FRAGMENT TYPE: internal (ix) FEATURE:
    (A) NAME/KEY: Active-site
    (B) LOCATION: 1..4
    (D) OTHER INFORMATION: /note= "Consensus sequence of catalytic center in esterases"

(ix) FEATURE:
    (A) NAME/KEY: Region
    (B) LOCATION: 4
    (D) OTHER INFORMATION: /note= "Amino acid 4 is phenylalanine or valine"

(xi) SEQUENCE DESCRIPTION: SEQ ID NO:26:

Asp Xaa Xaa Xaa
1

(2) INFORMATION FOR SEQ ID NO:27:

(i) SEQUENCE CHARACTERISTICS:
    (A) LENGTH: 7 amino acids
    (B) TYPE: amino acid
    (D) TOPOLOGY: linear (v) FRAGMENT TYPE: internal (ix) FEATURE:
    (A) NAME/KEY: Active-site
    (B) LOCATION: 1..7
    (D) OTHER INFORMATION: /note= "Consensus sequence of catalytic center in esterases"

(xi) SEQUENCE DESCRIPTION: SEQ ID NO:27:

Val Xaa Glu Xaa Xaa Xaa Tyr
1                5

(2) INFORMATION FOR SEQ ID NO:28:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:28:

CCACTTTCAC ACAACATCC          19

(2) INFORMATION FOR SEQ ID NO:29:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:29:

TGTAAAACGA CGGCCAGTTC TGAATTGCAG AAATCAGATA 40

( 2 ) INFORMATION FOR SEQ ID NO:30:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:30:

CAGGAAACAG CTATGACCCC ACTTTCACAC AACATCC 37

( 2 ) INFORMATION FOR SEQ ID NO:31:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:31:

AAGAACATAT ACAAAAGGTT GGTA 24

( 2 ) INFORMATION FOR SEQ ID NO:32:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:32:

TCTTCACTGC TCTGGGGTT 19

( 2 ) INFORMATION FOR SEQ ID NO:33:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:33:

TATTATCTCA GGCACAGATG 20

( 2 ) INFORMATION FOR SEQ ID NO:34:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:34:

CAAGTCCTTT GCTGACTTAT  20

( 2 ) INFORMATION FOR SEQ ID NO:35:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

TGTAAAACGA CGGCCAGTAT CTCAGGCACA GATGTTG  37

( 2 ) INFORMATION FOR SEQ ID NO:36:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

CAGGAAACAG CTATGACCGT CCTTTGCTGA CTTATAAA  38

( 2 ) INFORMATION FOR SEQ ID NO:37:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

GATTCCTATG ACATTATTTT CGA  23

( 2 ) INFORMATION FOR SEQ ID NO:38:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

CACAACACCA CCTCTAACAT CG  22

( 2 ) INFORMATION FOR SEQ ID NO:39:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

AACATACGGT TTTTACCTAA G                                                         21

( 2 ) INFORMATION FOR SEQ ID NO:40:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

TCTCTGAGTT TCAGCTAGG                                                            19

( 2 ) INFORMATION FOR SEQ ID NO:41:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:41:

TGTAAAACGA CGGCCAGTCA TACGGTTTTT ACCTAAGAA                                      39

( 2 ) INFORMATION FOR SEQ ID NO:42:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:42:

CAGGAAACAG CTATGACCCT GCGTTTCAGC TAGGACA                                        37

( 2 ) INFORMATION FOR SEQ ID NO:43:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

GCTCAATCAG ATAAACGTAC C                                                         21

( 2 ) INFORMATION FOR SEQ ID NO:44:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

TTCTCTGGCT CCACTACCGT                                                           20

( 2 ) INFORMATION FOR SEQ ID NO:45:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:45:

AGGATACTTG GCTATGGATC                    20

( 2 ) INFORMATION FOR SEQ ID NO:46:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:46:

GAAAGACGTT TTTGATTTTT TCC                23

( 2 ) INFORMATION FOR SEQ ID NO:47:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:47:

CATACTTATA TAAATGTGAC TAT                23

( 2 ) INFORMATION FOR SEQ ID NO:48:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:48:

TCTGACCCAG GTTCCAATT                     19

( 2 ) INFORMATION FOR SEQ ID NO:49:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:49:

TGTAAAACGA CGGCCAGTTA CTTATATAAA TGTGACTATC T    41

( 2 ) INFORMATION FOR SEQ ID NO:50:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear (i i) MOLECULE TYPE: DNA (genomic)

(x i) SEQUENCE DESCRIPTION: SEQ ID NO:50:

CAGGAAACAG CTATGACCGA CCCAGGTTCC AATTGTT 37

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:51:

CCAGAGATGT TTTAGTTGC 20

(2) INFORMATION FOR SEQ ID NO:52:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:52:

TGCTGTATGA GCTATAAACT T 21

(2) INFORMATION FOR SEQ ID NO:53:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:53:

TGTAAAACGA CGGCCAGTCC AGAGATGTTT TTAGTTG 37

(2) INFORMATION FOR SEQ ID NO:54:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:54:

CAGGAAACAG CTATGACCTG CTGTATGAGC TATAAACTT 39

(2) INFORMATION FOR SEQ ID NO:55:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:55:

```
GTCTAGAGTC TGACATAAAT T                                                21
```

( 2 ) INFORMATION FOR SEQ ID NO:56:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:56:

```
AACCCTACTC TTAAGGAGC                                                   19
```

( 2 ) INFORMATION FOR SEQ ID NO:57:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:57:

```
TTTGTAAGAC ACCGTGTAAG A                                                21
```

( 2 ) INFORMATION FOR SEQ ID NO:58:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:58:

```
CAGGAAACAG CTATGACCCA CCGTGTAAGA TGTAAGC                               37
```

( 2 ) INFORMATION FOR SEQ ID NO:59:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

```
CAGGAAACAG CTATGACCCA ACCCTACTCT TAAGGAGC                              38
```

( 2 ) INFORMATION FOR SEQ ID NO:60:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

```
TGTAAAACGA CGGCCAGTGT CTAGAGTCTG ACATAAATT                             39
```

( 2 ) INFORMATION FOR SEQ ID NO:61:

( i ) SEQUENCE CHARACTERISTICS:
   ( A ) LENGTH: 22 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:61:

TAAACAGCAG CGAATACTTT AT  22

( 2 ) INFORMATION FOR SEQ ID NO:62:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:62:

TTTTGCAAAG ACAACTAAAC TAACGCTGAA TG  32

( 2 ) INFORMATION FOR SEQ ID NO:63:

( i ) SEQUENCE CHARACTERISTICS:
      ( A ) LENGTH: 335 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: 5'UTR
      ( B ) LOCATION: 1..41

( i x ) FEATURE:
      ( A ) NAME/KEY: exon
      ( B ) LOCATION: 42..277

( i x ) FEATURE:
      ( A ) NAME/KEY: intron
      ( B ) LOCATION: 278..335

( x i ) SEQUENCE DESCRIPTION: SEQ ID NO:63:

TCTTCTGAAT TGCAGAAATC AGATAAAAAC TACTTGGTGA AATGACTTCT TGTCACATTG  60
CTGAAGAACA TATACAAAAG GTTGCTATCT TTGGAGGAAC CCATGGGAAT GAGCTAACCG  120
GAGTATTTCT GGTTAAGCAT TGGCTAGAGA ATGGCGCTGA GATTCAGAGA ACAGGGCTGG  180
AGGTAAAACC ATTTATTACT AACCCCAGAG CAGTGAAGAA GTGTACCAGA TATATTGACT  240
GTGACCTGAA TCGCATTTTT GACCTTGAAA ACCTTGGGTA AGACTATGCT TTGTATTGTA  300
TATGTATGGA TGTTGTGTGA AAGTGGTAGG TGTGT  335

( 2 ) INFORMATION FOR SEQ ID NO:64:

( i ) SEQUENCE CHARACTERISTICS:
      ( A ) LENGTH: 289 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: intron
      ( B ) LOCATION: 1..51

( i x ) FEATURE:

(A) NAME/KEY: exon
(B) LOCATION: 52..247

(ix) FEATURE:
(A) NAME/KEY: intron
(B) LOCATION: 248..289

(xi) SEQUENCE DESCRIPTION: SEQ ID NO:64:

```
TATTATCTCA GGCACAGATG TTGTTCATCT TTTTCTTTCT GCTTATAACA GCAAAAAAT      60
GTCAGAAGAT TTGCCATATG AAGTGAGAAG GGCTCAAGAA ATAAATCATT TATTTGGTCC    120
AAAAGACAGT GAAGATTCCT ATGACATTAT TTTTGACCTT CACAACACCA CCTCTAACAT    180
GGGGTGCACT CTTATTCTTG AGGATTCCAG GAATAACTTT TTAATTCAGA TGTTTCATTA    240
CATTAAGGTA ATGTTAATGT TATTAATTTA TAAGTCAGCA AAGGACTTG                289
```

(2) INFORMATION FOR SEQ ID NO:65:

(i) SEQUENCE CHARACTERISTICS:
(A) LENGTH: 200 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: intron
(B) LOCATION: 1..46

(ix) FEATURE:
(A) NAME/KEY: exon
(B) LOCATION: 47..140

(ix) FEATURE:
(A) NAME/KEY: intron
(B) LOCATION: 141..200

(xi) SEQUENCE DESCRIPTION: SEQ ID NO:65:

```
AACATACGGG TTTTTACCCA AGAAAGACGT TTTTGATTTT TTTCAGACTT CTCTGGCTCC     60
ACTACCCTGC TACGTTTATC TGATTGAGCA TCCTTCCCTC AAATATGCGA CCACTCGTTC    120
CATAGCCAAG TATCCTGTGG GTAAGTCATA GTTCCCACTG TCATAACTCA ATAAATATG     180
TCCTAGCTGA AACTCAGAGA                                                200
```

(2) INFORMATION FOR SEQ ID NO:66:

(i) SEQUENCE CHARACTERISTICS:
(A) LENGTH: 221 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: intron
(B) LOCATION: 1..39

(ix) FEATURE:
(A) NAME/KEY: exon
(B) LOCATION: 40..146

(ix) FEATURE:
(A) NAME/KEY: intron
(B) LOCATION: 148..221

(xi) SEQUENCE DESCRIPTION: SEQ ID NO:66:

```
TACTTATATA AATGTGACTA TCTCTCCTTC TGTACCTAGG TATAGAAGTT GGTCCTCAGC     60
CTCAAGGGGT TCTGAGAGCT GATATCTTGG ATCAAATGAG AAAAATGATT AAACATGCTC    120
```

| TTGATTTTAT | ACATCATTTC | AATGAAGGTA | AGTAATAATG | AAGGTAACGT | TATCAAACTT | 180 |
| AACCACCAAA | CATTTAAATA | ACAATTGGAA | CCTGGGTCAG | A | | 221 |

( 2 ) INFORMATION FOR SEQ ID NO:67:

( i ) SEQUENCE CHARACTERISTICS:
        ( A ) LENGTH: 235 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 1..47

( i x ) FEATURE:
        ( A ) NAME/KEY: exon
        ( B ) LOCATION: 48..157

( i x ) FEATURE:
        ( A ) NAME/KEY: intron
        ( B ) LOCATION: 158..235

( x i ) SEQUENCE DESCRIPTION: SEQ ID NO:67:

| CCAGAGATGT | TTTTAGTTGC | CATTGATACA | TATTGTTTTT | GTCATAGGAA | AAGAATTTCC | 60 |
| TCCCTGCGCC | ATTGAGGTCT | ATAAAATTAT | AGAGAAAGTT | GATTACCCCC | GGGATGAAAA | 120 |
| TGGAGAAATT | GCTGCTATCA | TCCATCCTAA | TCTGCAGGTA | ACATTGTTC | TTTCTTTAAA | 180 |
| ATGTTGAAAA | TAATAATGCT | GTACCTTTGA | ATAGAAGTTT | ATAGCTCATA | CAGCA | 235 |

( 2 ) INFORMATION FOR SEQ ID NO:68:

( i ) SEQUENCE CHARACTERISTICS:
        ( A ) LENGTH: 347 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 1..74

( i x ) FEATURE:
        ( A ) NAME/KEY: exon
        ( B ) LOCATION: 75..269

( i x ) FEATURE:
        ( A ) NAME/KEY: terminator
        ( B ) LOCATION: 270..272

( i x ) FEATURE:
        ( A ) NAME/KEY: 3'UTR
        ( B ) LOCATION: 273..347

( x i ) SEQUENCE DESCRIPTION: SEQ ID NO:68:

| GTCTAGAGTC | TGACATAAAT | TTTTAGAGGA | GAAAAACCAA | ATATAATATA | TTTATTTTGA | 60 |
| TTGTTTCCTG | AGAGGATCAA | GACTGGAAAC | CACTGCATCC | TGGGGATCCC | ATGTTTTAA | 120 |
| CTCTTGATGG | GAAGACGATC | CCACTGGGCG | GAGACTGTAC | CGTGTACCCC | GTGTTTGTGA | 180 |
| ATGAGGCCGC | ATATTACGAA | AAGAAAGAAG | CTTTTGCAAA | GACAACTAAA | CTAACGCTCA | 240 |
| ATGCAAAAAG | TATTCGCTGC | TGTTTACATT | AGAAATCACT | TCCAGCTTAC | ATCTTACACG | 300 |
| GTGTCTTACA | AATTCTGCTA | GTCTGTAAGC | TCCTTAAGAG | TAGGGTT | | 347 |

What is claimed is:

1. An isolated nucleic acid molecule comprising:
   (a) a nucleic acid sequence encoding a human aspartoacylase polypeptide;
   (b) a nucleic acid sequence fully complementary to nucleic acid sequence (a); or
   (c) a nucleic acid sequence at least 16 nucleotides in length capable of hybridizing specifically with one of said nucleic acid molecules (a) or (b).

2. A nucleic acid molecule of claim 1(a), comprising:
   (i) a DNA molecule having the DNA sequence of FIG. 1 from DNA position +1 to +891;
   (ii) a DNA molecule encoding a wild-type human aspartoacylase polypeptide having the amino acid sequence of FIG. 1 from amino acid position +1 to +313;
   (iii) a DNA molecule having a sequence of a fragment of the DNA sequence of FIG. 1, or a sequence fully complementary thereto, and including at least 16 sequential nucleotides; or
   (iv) a DNA molecule having a sequence of a fragment of the DNA sequence of FIG. 1 and including at least 16 sequential nucleotides, and which encodes a fragment of the amino acid sequence of FIG. 1.

3. A nucleic acid molecule of claim 1(a), comprising
   (i') a DNA molecule having the DNA sequence of FIG. 1 from DNA position +1 to +891;
   (ii') a DNA molecule encoding a human aspartoacylase polypeptide having the amino acid sequence of FIG. 1 from amino acid position +1 to +313;
   (iii') a DNA molecule having a sequence of a fragment of the DNA sequence of FIG. 1, or a sequence fully complementary thereto, and including at least 16 sequential nucleotides; or
   (iv') a DNA molecule having a sequence of a fragment of the DNA sequence of FIG. 1 and including at least 16 sequential nucleotides, and which encodes a fragment of the amino acid sequence of FIG. 1;
   wherein each of said DNA molecules (i'), (ii'), (iii') or (iv') differs by at least one nucleotide from the nucleotide sequence of FIG. 1, and is a naturally-occurring allele of human aspartoacylase having an altered biological activity.

4. An isolated DNA molecule of claim 1, comprising a DNA sequence encoding a human aspartoacylase polypeptide.

5. An isolated DNA molecule of claim 4, wherein the DNA codes for a wild-type human aspartoacylase polypeptide.

6. An isolated DNA molecule of claim 4, wherein the DNA codes for a naturally-occurring allele or a mutant of human aspartoacylase polypeptide having an altered biological activity as compared with a wild-type aspartoacylase polypeptide.

7. An isolated DNA molecule of claim 6, wherein the DNA codes for an aspartoacylase polypeptide which, if expressed in cells of the human body, is associated with altered cellular function which correlates with Canavan disease.

8. An isolated nucleic acid primer or probe molecule comprising a DNA sequence, or its RNA equivalent, of the sequence (iii) or (iv) of claim 2, or a sequence fully complementary thereto.

9. An isolated nucleic acid primer or probe molecule comprising a DNA sequence, or its RNA equivalent, of the sequence (iii') or (iv') of claim 3, or a sequence complementary thereto.

10. A nucleic acid molecule of claim 8, having the sequence
    5'-CTTCTGAATTGCAGAAATCA-3' (HASP9) (SEQ ID NO:20) or
    5'-GTAAGACACCGTGTAAGATG-3' (HASPC7) (SEQ ID NO:21).

11. A nucleic acid molecule of claim 9, having the sequence
    5'-F→CCGGGATGAAAATGGAGAA-3' (HASP14F) (SEQ ID NO:6) or
    5'-R→ACCGTGTAAGATGTAAGC-3' (HASPC7R) (SEQ ID NO:7),
    wherein F and R are M13 universal and/or reverse primer tags linked or ligated to said nucleic acid molecule.

12. A DNA molecule of claim 5, having the DNA sequence of FIG. 1 from DNA position +1 to +891.

13. A DNA molecule of claim 7, having the DNA sequence of FIG. 1 from DNA position +1 to +891, wherein the adenine nucleotide at position 854 is replaced by a cytosine nucleotide.

14. A recombinant vector comprising a DNA molecule of claim 1.

15. A vector of claim 14, wherein said DNA molecule is operably linked to an expression control sequence suitable for expression of said DNA sequence in a host cell.

16. A host cell transformed with a vector of claim 15.

17. A host cell of claim 16, selected from a strain of *E. coli*, Pseudomonas, *Bacillus subtilis*, *Bacillus stearothermophilus*, or other bacilli; other bacteria; yeast; other fungi; insect cells; plant cells; or murine, bovine, porcine, human or other mammalian cells.

18. A method of producing a wild-type aspartoacylase polypeptide, comprising
    (a) culturing a host cell transformed with a vector of claim 15 containing a DNA coding for a wild-type aspartoacylase polypeptide in a cell culture medium under conditions whereby the aspartoacylase polypeptide is expressed, and
    (b) isolating the thus-produced wild-type aspartoacylase polypeptide.

19. An isolated aspartoacylase gene, comprising a DNA sequence of claim 1 operably linked to a DNA sequence encoding a human aspartoacylase expression control sequence.

20. An isolated gene of claim 19, encoding and capable of expressing a wild-type aspartoacylase polypeptide.

21. An isolated gene of claim 19, which is not capable of expressing a wild-type aspartoacylase polypeptide.

22. An isolated gene of claim 21, encoding and capable of expressing a mutant aspartoacylase polypeptide having an altered ability of hydrolyze N-acetyl-aspartic acid to aspartate and acetate or incapable of hydrolyzing N-acetyl-aspartic acid to aspartate and acetate.

23. An isolated gene of claim 22, which, if expressed in cells of the human body, is associated with altered cellular function which correlates with Canavan disease.

24. An isolated gene of claim 21, wherein said expression control sequence is mutated and is not capable of expression of aspartoacylase.

25. A method of screening a subject to determine if said subject is a Canavan carrier or a Canavan patient, comprising
    (a) providing a biological sample of the subject to be screened; and
    (b) submitting the sample to an assay for detecting in the biological sample the presence of a wild-type aspartoacylase gene, a mutant aspartoacylase gene or a mixture thereof, wherein said gene has a DNA sequence of claim 1, and wherein detection of a mutant as aspartoacylase gene indicates that the subject is a Canavan carrier or a Canavan patient.

26. A method of claim 25, wherein the biological sample includes at least part of the genome of the subject and the assay comprises a hybridization assay.

27. A method of claim 25, wherein the assay comprises at least one labeled nucleotide probe.

28. A method of claim 27, wherein the assay comprises a labeled nucleotide probe comprising a DNA molecule having a sequence of a fragment of the DNA sequence of FIG. 1, or a sequence complementary thereto, and including at least 16 sequential nucleotides.

29. A method of claim 27, wherein the probe is selected from the sequences

5'-CTTCTGAATTGCAGAAATCA-3' (HASP9) (SEQ ID NO:20),

5'-GTAAGACACCGTGTAAGATG-3' (HASPC7) (SEQ ID NO:21),

5'-F→CCGGGATGAAAATGGAGAA-3' (HASP14F) (SEQ ID NO:6) or

5'-R→ACCGTGTAAGATGTAAGC-3' (HASPC7R) (SEQ ID NO:7), wherein F and R are M13 universal and/or reverse primer tags linked or ligated to said nucleic acid molecule.

30. A process for screening a potential Canavan disease carrier or patient for the presence of an identified mutation in an aspartoacylase gene, comprising (a) isolating genomic DNA from said potential Canavan disease carrier or patient, (b) hybridizing a DNA probe of claim 9 with said isolated genomic DNA, said DNA probe spanning said mutation in said aspartoacylase gene, wherein said DNA probe is capable of detecting said mutation, (c) determining the presence or absence of said DNA probe hybridized with said genomic DNA, said hybridization indicating the presence or absence of said aspartoacylase mutation.

31. A process for screening a potential Canavan disease carrier or patient for the presence of an identified mutation in an aspartoacylase gene having a nucleic acid sequence of claim 1a, comprising (a) isolating genomic DNA from said potential Canavan disease carrier or patient, (b) determining the presence or absence of a restriction endonuclease site in the gene, the presence or absence of which thereby indicates the presence or absence of said aspartoacylase mutation.

32. A process for screening a potential Caravan disease carrier or patient for the presence of an identified mutation in an aspartoacylase gene, comprising (a) isolating genomic DNA from said potential Canavan disease carrier or patient, (b) performing PCR on said genomic DNA, using a primer of claim 8, (c) adding PCR products produced from wild-type genomic DNA using the same primer, (d) forming heteroduplexes between said PCR products, and (e) determining the mobility of said heteroduplex PCR products in polyacrylamide gels as compared with the mobility of PCR products produced from wild-type genomic DNA using the same primer, wherein an altered mobility of said heteroduplex PCR products indicates the presence of said aspartoacylase mutation.

33. A kit for assaying for the presence of an aspartoacylase gene by hybridization assay, comprising:

(a) an oligonucleotide probe of claim 8 which specifically hybridizes to the aspartoacylase gene; and (b) a reagent means for detecting of the hybridization of the oligonucleotide probe to the gene;

wherein the probe and reagent means are each present in amounts effective to perform the hybridization assay.

34. A kit of claim 33, wherein said aspartoacylase gene is a wild-type aspartoacylase gene.

35. A kit of claim 33, wherein said aspartoacylase gene is a mutant aspartoacylase gene.

36. A kit of claim 33, further comprising an oligonucleotide probe which specifically hybridizes one or more additional mutant or wild-type genes, and, optionally, a corresponding additional reagent means for detecting hybridization of said oligonucleotide probe which specifically hybridizes to said additional gene, wherein said additional gene codes for a protein associated with an additional genetic disease.

37. A kit of claim 36, wherein the additional genetic disease is Tay-Sachs disease and/or Goucher disease.

38. A nucleic acid molecule of claim 1, selected from the sequences SEQ ID NO:28–SEQ ID NO:62 and nucleotides 119–139 of SEQ ID NO:1.

39. A method of producing a mutant aspartoacylase polypeptide having an altered biological activity as compared with a wild-type aspartoacylase polypeptide, comprising (a) culturing a host cell transformed with a vector of claim 15 containing a DNA coding for a mutant aspartoacylase polypeptide in a cell culture medium under conditions whereby the aspartoacylase polypeptide is expressed, and (b) isolating the thus-produced mutant aspartoacylase polypeptide.

40. A process for screening a potential Canavan disease carrier or patient for the presence of an identified mutation in an aspartoacylase gene, comprising (a) isolating genomic DNA from said potential Canavan disease carrier or patient, (b) hybridizing a DNA probe of claim 8 with said isolated genomic DNA, said DNA probe spanning said mutation in said aspartoacylase gene, (c) determining the presence or absence of said DNA probe hybridized with said genomic DNA, said hybridization indicating the presence or absence of said aspartoacylase mutation.

41. A process for screening a potential Canavan disease carrier or patient for the presence of an identified mutation in an aspartoacylase gene, comprising (a) isolating genomic DNA from said potential Canavan disease carrier or patient, (b) performing PCR on said genomic DNA, using a primer of claim 9, (c) optionally, adding PCR products produced from wild-type genomic DNA, and (d) determining the mobility of heteroduplex PCR products in polyacrylamide gels as compared with the mobility of PCR products produced from wild-type genomic DNA using the same primer or primers, the mobility of which thereby indicates the presence or absence of said aspartoacylase mutation.

42. A kit for assaying for the presence of an aspartoacylase gene by hybridization assay, comprising:
 (a) an oligonucleotide probe of claim 9 which specifically hybridizes to the aspartoacylase gene; and
 (b) a reagent means for detecting the hybridization of the oligonucleotide probe to the gene;
wherein the probe and reagent means are each present in amounts effective to perform the hybridization assay.

43. A kit of claim 42, further comprising an additional oligonucleotide probe which specifically hybridizes to one or more additional mutant or wild-type genes, and, optionally, a corresponding additional reagent means for detecting hybridization of said oligonucleotide probe which specifically hybridizes to said additional gene, wherein said additional gene codes for a protein associated with an additional genetic disease.

44. A kit of claim 42, wherein the additional genetic disease is Tay-Sachs disease and/or Goucher disease.

* * * * *